US007973057B2

(12) United States Patent
Greig et al.

(10) Patent No.: US 7,973,057 B2
(45) Date of Patent: Jul. 5, 2011

(54) THALIDOMIDE ANALOGS

(75) Inventors: Nigel H. Greig, Phoenix, MD (US); Harold Holloway, Middle River, MD (US); Arnold Brossi, Bethesda, MD (US); Xiaoxiang Zhu, North Brunswick, NJ (US); Tony Giordano, Shreveport, LA (US); Qian-sheng Yu, Lutherville, MD (US); William D. Figg, Fairfax, VA (US)

(73) Assignees: The United States of America as represented by the Department of Health and Human Services, Washington, DC (US); P2D Inc., Cincinnati, OH (US)

( * ) Notice: Subject to any disclaimer, the term of this patent is extended or adjusted under 35 U.S.C. 154(b) by 1132 days.

(21) Appl. No.: 10/572,485

(22) PCT Filed: Sep. 17, 2004

(86) PCT No.: PCT/US2004/030506
§ 371 (c)(1),
(2), (4) Date: Mar. 17, 2006

(87) PCT Pub. No.: WO2005/028436
PCT Pub. Date: Mar. 31, 2005

(65) Prior Publication Data
US 2006/0211728 A1  Sep. 21, 2006

Related U.S. Application Data

(60) Provisional application No. 60/504,724, filed on Sep. 17, 2003.

(51) Int. Cl.
*A01N 43/40* (2006.01)
*A61K 31/445* (2006.01)
(52) U.S. Cl. ......... 514/323; 546/201; 546/221; 514/183
(58) Field of Classification Search .................. 514/183
See application file for complete search history.

(56) References Cited

U.S. PATENT DOCUMENTS

| 2,830,991 | A | | 4/1958 | Keller et al. |
| 3,314,953 | A | | 4/1967 | Aristotle et al. |
| 3,320,270 | A | | 5/1967 | Grogan et al. |
| 3,560,495 | A | | 2/1971 | Frankus et al. |
| 3,794,641 | A | | 2/1974 | Görög et al. |
| 4,092,147 | A | | 5/1978 | Ashkar et al. |
| 4,291,048 | A | | 9/1981 | Gold et al. |
| 5,434,170 | A | | 7/1995 | Andrulis, Jr. |
| 5,593,900 | A | | 1/1997 | D'Amato |
| 5,593,990 | A | * | 1/1997 | D'Amato ............. 514/235.2 |
| 5,605,684 | A | | 2/1997 | Piacquadio |
| 5,629,327 | A | | 5/1997 | D'Amato |
| 5,712,291 | A | | 1/1998 | D'Amato |
| 5,783,605 | A | | 7/1998 | Kuo et al. |
| 5,789,434 | A | | 8/1998 | Kluender et al. |
| 5,840,724 | A | | 11/1998 | Fenton et al. |
| 6,071,948 | A | | 6/2000 | D'Amato |
| 6,080,742 | A | | 6/2000 | Germann et al. |
| 6,096,768 | A | | 8/2000 | Ashton et al. |
| 6,110,941 | A | | 8/2000 | Zimmer et al. |
| 6,124,322 | A | | 9/2000 | Bjoerkman et al. |
| 6,235,756 | B1 | | 5/2001 | D'Amato |
| 6,306,879 | B1 | | 10/2001 | Germann et al. |
| 6,417,197 | B1 | | 7/2002 | Schneider et al. |
| 6,420,414 | B1 | | 7/2002 | D'Amato |
| 6,458,810 | B1 | | 10/2002 | Muller et al. |
| 6,469,045 | B1 | | 10/2002 | D'Amato |
| 6,500,845 | B1 | | 12/2002 | Boehlke et al. |
| 6,518,298 | B2 | | 2/2003 | Green et al. |
| 6,555,554 | B2 | | 4/2003 | Muller et al. |
| 6,762,195 | B2 | | 7/2004 | Muller et al. |
| 2001/0041716 | A1 | | 11/2001 | Laing et al. |
| 2002/0161023 | A1 | | 10/2002 | D'Amato |
| 2003/0013739 | A1 | | 1/2003 | Masferrer |
| 2003/0045552 | A1 | * | 3/2003 | Robarge et al. ............. 514/323 |
| 2003/0181428 | A1 | | 9/2003 | Green et al. |
| 2005/0004087 | A1 | | 1/2005 | D'Amato et al. |

FOREIGN PATENT DOCUMENTS

| CA | 2104776 | 8/1992 |
| CA | 2251060 | 3/1997 |
| CA | 2228385 | 1/1998 |
| CA | 2248838 | 10/1998 |
| CA | 2302886 | 3/2000 |
| EP | 1 336 602 A1 | 8/2003 |
| GB | 962857 | 7/1964 |
| GB | 1049283 | 11/1966 |
| GB | 1075420 | 7/1967 |
| WO | WO 92/18496 | 10/1992 |
| WO | WO 94/20085 | 9/1994 |
| WO | WO 95/17154 | 6/1995 |
| WO | WO 96/20705 | 7/1996 |

(Continued)

OTHER PUBLICATIONS

Voss, Juergen, 2,4-Bis(4-methoxyphenyl)-1,3,2,4-dithiaphosphetane, 2001, Encyclopedia of Reagents for Organic Synthesis (e-EROS). Abstract only.*
Patani et al., Bioisosterism: A Rational Approach in Drug Design, 1996, Chem. Rev., vol. 96, pp. 3147-3176.*
Bray et al., "Improved Procedures for the Preparation of (+)—(1R, 2S, 4R)-4-Amino-2-Hydroxy-1-Hydroxymethyl Cyclopentane," *Tetrahedron Letters* 36(25):4483-4486, 1995.
Cava et al., "Thionation Reactions of Lawesson's Reagents," *Tethrahedron* 41(22):5061-5087, 1985.
Corral et al., "Differential Cytokine Modulation and T Cell Activation by Two Distinct Classes of Thalidomide Analogues that are Potent Inhibitors of TNF-α," *The Journal of Immunology* 163:380-386, 1999.

(Continued)

*Primary Examiner* — Leslie A. Royds Draper
*Assistant Examiner* — Meghan Finn
(74) *Attorney, Agent, or Firm* — Klarquist Sparkman, LLP

(57) ABSTRACT

Thalidomide analogs that modulate tumor necrosis factor alpha (TNF-α) activity and angiogenesis are disclosed. In particularly disclosed embodiments, the thalidomide analogs are isosteric sulfur-containing analogs. Also disclosed are methods of treating a subject with the analogs.

11 Claims, 11 Drawing Sheets

FOREIGN PATENT DOCUMENTS

| WO | WO 96/20926 | 7/1996 |
|---|---|---|
| WO | WO 97/12625 | 4/1997 |
| WO | WO 97/23457 | 7/1997 |
| WO | WO 97/37988 | 10/1997 |
| WO | WO 97/45117 | 12/1997 |
| WO | WO 98/03502 | 1/1998 |
| WO | WO 98/19649 | 5/1998 |
| WO | WO 98/25895 | 6/1998 |
| WO | WO 99/13873 | 3/1999 |
| WO | WO 99/58096 | 11/1999 |
| WO | WO 99/59960 | 11/1999 |
| WO | WO 02/064083 | 8/2002 |
| WO | WO 02/068414 A2 | 9/2002 |
| WO | WO 03/014315 | 2/2003 |
| WO | WO 03/097052 | 11/2003 |
| WO | WO 2004/085422 | 10/2004 |
| WO | WO 2005/016326 A2 | 2/2005 |

OTHER PUBLICATIONS

Deckers et al., "Effect of Angiogenic and Antiangiogenic Compounds on the Outgrowth of Capillary Structures from Fetal Mouse Bone Explants," *Laboratory Investigation* 81(1):5-15, 2001.

Dredge et al., "Protective Antitumor Immunity Induced by a Costimulatory Thalidomide Analog in Conjunction with Whole Tumor Cell Vaccination is Mediated by Increased Th1-Type Immunity," *The Journal of Immunology* 168:4914-4919, 2002.

Greig et al., "Thalidomide-based TNF-α inhibitors for neurodegenerative diseases," *Acta Neurobiol Exp* 64:1-9, 2004.

Hashimoto et al., "Novel Biological Response Modifiers Derived from Thalidomide," *Current Medicinal Chemistry* 5:163-178, 1998.

Hashimoto et al., "Structural Development of Biological Response Modifiers Based on Thalidomide," *Bioorganic & Medicinal Chemistry* 10:461-479, 2002.

Lentzsch et al., "S-3-Amino-phthalimido-glutarimide Inhibits Angiogenesis and Growth of B-Cell Neoplasias in Mice," *Cancer Research* 62:2300-2305, 2002.

Luzzio et al., "Thalidomide metabolites and analogs. Part 2: Cyclic derivatives of 2-N-phthalimido-2S,3S (3-hydroxy) ornithine," *Tetrahedron Letters* 41:7151-7155, 2000.

Luzzio et al., "Thalidomide Metabolites and Analogues. 3. Synthesis and Antiangiogenic Activity of the Teratogenic and TNF-α-Modulatory Thalidomide Analogue 2-(2,6-Dioxopiperidine-3-yl)phthalimidine," *Journal of Medicinal Chemistry* 46(18):3793-3799, 2003.

Marriott et al., "CC-3052: A Water-Soluble Analog of Thalidomide and Potent Inhibitor of Activation-Induced TNF-α Production," *The Journal of Immunology* 161:4239-4243, 1998.

Meierhofer et al., "New Insights into the pharmacological and toxicological effects of thalidomide," *Current Opinion in Drug Discovery & Development* 6(1):92-99, 2003.

Miyachi et al., "Inducer-Specific Regulators of Tumor Necrosis Factor Alpha Production," *Chem. Pharm. Bull* 44(10):1980-1982, 1996.

Miyachi et al., "Novel Biological Response Modifiers: Phthalimides with Tumor Necrosis Factor-α Production-Regulating Activity," *J. Med. Chem.* 40(18):2858-2865, 1997.

Orzeszko et al., "Tumor necrosis factor-alpha production-regulating activity of phthalimide derivatives in genetically modified murine melanoma cells B78H1," *Il Farmaco* 58:371-376, 2003.

Shah et al., "Synthesis and Enantiomeric Separation of 2-Phthalimidino-glutaric Acid Analogues: Potent Inhibitors of Tumor Metastasis," *J. Med. Chem.* 42(16):3014-3017, 1999.

Shimazawa et al., "Nonpeptide Small-Molecular Inhibitors of Dipeptidyl Peptidase IV: N-Phenylphthalimide Analogs," *Bioorganic & Medicinal Chemistry Letters* 9:559-562, 1999.

Shimazawa et al., "Antiangiogenic Activity of Tumor Necrosis Factor-α Production Regulator Derived from Thalidomide," *Biol. Pham. Bull.* 22(2):224-226, 1999.

Shimazawa et al., "Novel Small Molecule Nonpeptide Aminopeptidase N Inhibitors with Cyclic Imide Skeleton," *J. Enzyme Inhibition* 14:259-275, 1999.

Teubert et al., "5'-Substituted Thalidomide Analogs as Modulators of TNF-α," *Arch. Pharm. Pharm. Med. Chem.* 331:7-12, 1998.

Tsenova et al., "Use of IMiD3, a Thalidomide Analog, as an Adjunct to Therapy for Experimental Tuberculous Meningitis," *Antimicrobial Agents and Chemotherapy* 46(6):1887-1895, 2002.

Weinz et al., "Investigation of the in vitro biotransformation and simultaneous enantioselective separation of thalidomide and its neutral metabolites by capillary electrophoresis," *Journal of Chromatography B* 674:287-292, 1995.

Zhu et al., "Thiothalidomides: Novel Isosteric Analogues of Thalidomide with Enhanced TNF-α Inhibitory Activity," *J. Med. Chem.* 26(24):5222-5229, 2003.

Bartlett et al., "Phase I study to determine the safety, tolerability and immunostimulatory activity of thalidomide analogue CC-5013 in patents with metastatic malignant melanoma and other advanced cancers," *British Journal of Cancer* 90:955-961, 2004.

Bauer et al., "Inhibition of Angiogenesis by Thalidomide Requires Metabolic Activation, Which is Species-dependent," *Biochemical Pharmacology* 55:1827-1834, 1998.

Ching et al., "Interaction of thalidomide, phthalimide analogues of thalidomide and pentoxifylline with the anti-tumour agent 5,6-dimethylxanthenone-4-acetic acid: concomitant reduction of serum tumour necrosis factor-alpha and enhancement of anti-tumour activity," *British Journal of Cancer* 78(3):336-343, 1998.

D'Amato et al., "Thalidomide is an inhibitor of angiogenesis," *Proc. Natl. Acad. Sci. USA* 91:4082-4085, 1994.

Dalgleish et al., "Thalidomide Analogues CC-5013 and CC-4047 Induce T cell Activation and IL-12 Production in Patients with Both Solid Tumours and Relapsed and Refractory Multiple Myeloma," *British Journal of Cancer* 88(Suppl. 1)S25-S54 (Abstract P14), 2003.

Davies et al., "Thalidomide (Thal) and Immunomodulatory Derivatives (IMiDs) Augment Natural Killer (NK) Cell Cytotoxicity in Multiple Myeloma (MM)," American Society of Hematology, 42nd Annual Meeting, San Francisco, CA, Dec. 1-5, 2000 (Abstract No. 3617).

Davies et al., "Thalidomide (Thal) and Immunomodulatory Derivatives (IMiDs) Augment Natural Killer (NK) Cell Cytotoxicity in Multiple Myeloma (MM)," VIIIth International Myeloma Workshop, Banff, Canada, May 4-8, 2001 (Abstract No. P222).

Davies et al., "Thalidomide and immunomodulatory derivatives augment natural killer cell cytotoxicity in multiple myeloma," *Blood* 98(1):210-216, 2001.

De et al., "Possible Antineoplastic Agents: III Synthesis of 6-Alkyl-2-U4'Methoxyphalimido and 6-Alkyl-3-U3'-4'-Dimethoxyphenyl Glutarimides," *J. Indian Chem. Soc.* 53:1122-1125, 1976.

De et al., "Possible Antineoplastic Agents: Part IV—Synthesis & Antineoplastic Potency of N-Substituted α-(4,5-Dimethoxyphthalimido)gludarimides & N-Substituted β-(4-Bromophenyl)glutarimides," *Indian J. of Chem.* 16B:510-512, 1978.

Dibbs et al., "Thalidomide and Thalidomide Analogs Suppress TNFα Secretion by Myocytes," *Circulation* 98(17(Suppl), Abstract No. 1284):I247, 1998.

Dredge et al., "A costimulatory thalidomide analog enhances the partial anti-tumor immunity of an autologous vaccination in a model of colorectal cancer," American Association for Cancer Research, 93rd Annual Meeting, San Francisco, CA, Apr. 6-10, 2002 (Abstract No. 491).

Dredge et al., "Novel thalidomide analogues display anti-angiogenic activity independently of immunomodulatory effects," *British Journal of Cancer* 87:1166-1172, 2002.

Dredge et al., "Recent developments in antiangiogenic therapy," *Expert Opin. Biol. Ther.* 2(8):953-966, 2002.

Dredge et al., "Immunological Effects of Thalidomide and Its Chemical and Functional Analogs," *Critical Reviews in Immunology* 22(5&6):425-437, 2002.

Dredge et al., "Thalidomide analogs as emerging anti-cancer drugs," *Anti-Cancer Drugs* 14:331-335, 2003.

Dredge et al., "Angiogenesis inhibitors in cancer therapy," *Current Opinion in Investigational Drugs* 4(6):667-674, 2003.

Eisen et al., "Continuous low dose Thalidomide: a phase II study in advanced melanoma, renal cell, ovarian and breast cancer," *British Journal of Cancer* 82(4):812-817, 2000.

Fine et al., "Phase II Trial of the Antiangiogenic Agent Thalidomide in Patients with Recurrent High-Grade Gliomas," *Journal of Clinical Oncology* 18(4):708-715, 2000.

Folkes et al., "Oxidative activation of indole-3-acetic acids to cytotoxic species—a potential new role for plant auxins in cancer therapy," *Biochemical Pharmacology* 61(2):129-136, 2001.

Greig et al., "New Therapeutic Strategies and Drug Candidates for Neurodegenerative Diseases. p53 and TNF-α Inhibitors, and GLP-1 Receptor Agonists," *Ann. N.Y. Acad. Sci.* 1035:290-315, 2004.

Gupta et al., "Adherence of multiple myeloma cells to bone morrow stromal cells upregulates vascular endothelial growth factor secretion: therapeutic applications," *Leukemia* 15:1950-1961, 2001.

Gütschow et al., "Aza Analogues of Thalidomide: Synthesis and Evaluation as Inhibitors of Tumor Necrosis Factor-α Production In Vitro," *Bioorganic & Medicinal Chemistry* 9:1059-1065, 2001.

Haslett et al., "Thalidomide and a Thalidomide Analogue Drug Costimulate Virus-Specific CD8$^+$ T Cells In Vitro," *The Journal of Infectious Diseases* 187:946-955, 2003.

Hayashi et al., "Mechanisms Whereby Immunomodulatory Analogs of Thalidomide Augment Autologous NK Cell Anti-Myeloma Immunity," American Society of Hematology, 44$^{th}$ Annual Meeting, Philadelphia, PA, Dec. 6-10, 2002 (Abstract No. 3219).

He et al., "Synthesis of Thalidomide Analogs and Their Biological Potential For Treatment of Graft Versus Host Disease (GVHD)," American Chemical Society (Abstract No. 216), 1993.

Hernandez-Ilizaliturri et al., "Addition of Immunomodulatory Drugs CC5013 or CC4047 to Rituximab Enhances Anti-Tumor Activity in a Severe Combined Immunodeficiency (SCID) Mouse Lymphoma Model," American Society of Hematology, 45$^{th}$ Annual Meeting, San Diego, CA, Dec. 6-9, 2003 (Abstract No. 235).

Hess et al., "Synthesis and immunological activity of water-soluble thalidomide prodrugs," *Bioorganic and Medicinal Chem.* 9(5):1279-1291, 2001.

Hideshima et al., "Thalidomide (Thal) and Its Analogs Overcome Drug Resistance of Human Multiple Myeloma (MM) Cells to Conventional Therapy," American Society of Hematology, 42$^{nd}$ Annual Meeting, San Francisco, CA, Dec. 1-5, 2000 (Abstract No. 1313).

Jönsson, "Chemical structure and teratogenic properties," *Acta Pharm. Suecica* 9:521:542, 1972.

Karbownik et al., "Indole-3-propionic acid, a melatonin-related molecule, protects hepatic microsomal membranes from iron-induced oxidative damage: relevance to cancer reduction," *Journal of Cellular Biochemistry* 81(3):507-513, 2001.

Kim et al., "Inhibition of vascular endothelial growth factor-induced angiogenesis suppresses tumour growth in vivo," *Nature* 362:841-844, 1993.

Kumar et al., "Antimyeloma activity of two novel N-substituted and tetraflourinated thalidomide analogs," *Leukemia* 19:1253-1561, 2005.

Lentzsch et al., "Immunomodulatory Derivatives of Thalidomide (IMiD CC-4047) Down Regulates CAAT/Enhancer-Binding Protein β(C/EBPβ) in Multiple Myeloma (MM)", American Society of Hematology, 45$^{th}$ Annual Meeting, San Diego, CA, Dec. 6-9, 2003 (Abstract No. 3456).

Lentzsch et al., "Immunomodulatory Derivatives of Thalidomide (IMiD CC-4047) Determine the Lineage Commitment of Hematopoietic Progenitors by Down Regulation of GATA-1 and Modulation of Cytokine Secretion," American Society of Hematology, 45$^{th}$ Annual Meeting, San Diego, CA, Dec. 6-9, 2003 (Abstract No. 3073).

Lepper et al., "Comparative Molecular Field Analysis and Comparative Molecular Similarity Indices Analysis of Thalidomide Analogues as Angiogenesis Inhibitors," *J. Med. Chem.* 47:2219-2227, 2004.

Little et al., "Activity of Thalidomide in AIDS-Related Kaposi's Sarcoma," *Journal of Clinical Oncology* 18(13):2593-2602, 2000.

Man et al., "α-Fluoro-Substituted Thalidomide Analogues," *Bioorganic & Medicinal Chemistry Letters* 13:3415-3417, 2003.

Marriott et al., "Immunotherapeutic and antitumour potential of thalidomide analogues," *Expert Opin. Biol. Ther.* 1(4):1-8, 2001.

Marriott et al., "Thalidomide and its analogues have distinct and opposing effects on TNF-α and TNFR2 during co-stimulation of both CD4$^+$ and CD8$^+$ T cells," *Clin Exp Immunol* 130:75-84, 2002.

Marriott et al., "A Novel Subclass of Thalidomide Analogue with Anti-Solid Tumor Activity in Which Caspase-dependent Apoptosis is Associated with Altered Expression of bcl-2 Family Proteins," *Cancer Research* 63:593-599, 2003.

Marriott et al., "Thalidomide Derived Immunomodulatory Drugs (IMiDs) as Potential Therapeutic Agents," *Current Drug Targets—Immune, Endocrine & Metabolic Disorders* 3:181-186, 2003.

Mitsiades et al., "Apoptotic signaling induced by immunomodulatory thalidomide analogs in human multiple myeloma cells: therapeutic implications," *Blood* 99(12):4525-4530, 2002.

Moutouh de Parseval et al., "Novel immunomodulatory drugs (IMiDs®): A potential, new therapy for β-hemoglobinopathies," American Society of Hematology, 46$^{th}$ Annual Meeting, San Diego, CA, Dec. 4-7, 2004 (Abstract No. 3740).

Muller et al., "Amino-Substituted Thalidomide Analogs: Potent Inhibitors of TNF-α Production," *Bioorganic & Medicinal Chemistry Letters* 9:1625-1630, 1999.

Neumann et al., "N-(Sulfonyloxy)phthalimides and Analogues Are Potent Inactivators of Serine Proteases," *The Journal of Biological Chemistry* 269(34):21561-21567, 1994.

Ng et al., "Antiangiogenic Activity of N-substituted and Tetrafluorinated Thalidomide Analogues," *Cancer Research* 63(12):3189-3194, 2003.

Ng et al., "Antitumor Effects of Thalidomide Analogs in Human Prostate Cancer Xenografts Implanted in Immunodeficient Mice," *Clinical Cancer Research* 10:4192-4197, 2004.

Ni et al., "Experimental study on activity of human recombinant adenovirus vector expressing human endostatin in vitro," *Dier Junyi Daxue Xuebao Bianjibu* 23(3):261-263, 2002 (Abstract only).

Niwayama et al., "Enhanced Potency of Perfluorinated Thalidomide Derivatives for Inhibition of LPS-Induced Tumor Necrosis Factor-α Production is Associated with a Change of Mechanism of Action," *Bioorganic & Medicinal Chemistry Letters* 8:1071-1076, 1998.

Niwayama et al., "Potent Inhibition of Tumor Necrosis Factor-α Production by Tetrafluorothalidomide and Tetrafluorophthalimides," *J. Med. Chem.* 39:3044-3045, 1996.

Pagani et al., "Effetto Sul Geotropism Radicale di Semi di Lens Esculenta Moench s.l. di una Serie di Sostanze Correlate All'Acido N-α-Naftilftalamico," *Farmaco Ed. Sci.* 25:203-225, 1970.

Patten et al., "The Early Use of the Serum Free Light Chain Assay in Patients with Relapsed Refractory Myeloma Receiving Treatment with a Thalidomide Analogue (CC-4047)," American Society of Hematology, 45$^{th}$ Annual Meeting, San Diego, CA, Dec. 6-9, 2003 (Abstract No. 1640).

Payvandi et al., "The thalidomide analogs IMiDs enhance expression of CD69 stimulatory receptor on natural killer cells," American Association of Cancer Research, 92$^{nd}$ Annual Meeting, New Orleans, LA, Mar. 24-28, 2001 (Abstract No. 1793).

Payvandi et al., "Thalidomide analogs IMiDs inhibit expression of cyclooxygenase-2 in multiple myeloma cell line and LPS stimulated PBMCs," American Society of Hematology, 43$^{rd}$ Annual Meeting, Orlando, FL, Dec. 7-11, 2001 (Abstract No. 2689).

Payvandi et al., "Thalidomide and IMiDs Inhibit Microvessel Formation from Human Arterial Rings in the Absence of Human Liver Microsomes," American Society of Hematology, 44$^{th}$ Annual Meeting, Philadelphia, PA, Dec. 6-10, 2002 (Abstract No. 5046).

Payvandi et al., "CC-5013 inhibits the expression of adhesion molecules ICAM-1 and CD44 and prevents metastasis of B16 F10 mouse melanoma cells in an animal model," American Society of Clinical Oncology, 39$^{th}$ Annual Meeting, Chicago, IL, May 31-Jun. 3, 2003 (Abstract No. 992).

Payvandi et al., "Immunomodulatory drugs inhibit expression of cyclooxygenase-2 from TNF-α, IL-1β, and LPS-stimulated human PBMC in a partially IL-10-dependent manner," *Cellular Immunology* 230:81-88, 2004.

Pratt et al., "Phthalic Acid Derivatives : Constitution and Color, XIV. Some Derivatives of Tetra-Bromophthalimide," *J. Amer. Chem. Soc.* 40:1415-1425, 1918.

Schafer et al., "Enhancement of Cytokine Production and AP-1 Transcriptional Activity in T Cells by Thalidomide-Related Immunomodulatory Drugs," *The Journal of Pharmacology and Experimental Therapeutics* 305(3):1222-1232, 2003.

Schey et al., "Phase I Study of an Immunomodulatory Thalidomide Analog, CC-4047, in Relapsed or Refractory Multiple Myeloma," *Journal of Clinical Oncology* 22(16):1-8, 2004.

Sedlak et al., "Preparation, 1H and 13C NMR spectra of substituted 2-benzoylaminocarboxamides," *Collection of Czechoslovak Chemical Communications, Academic Press* 60:150-160, 1995.

Shaughnessy et al., "Global Gene Expression Analysis Shows Loss of C-MYC and IL-6 Receptor Gene mRNA After Exposure of Myeloma to Thalidomide and IMiD," The American Society of Hematology, 42nd Annual Meeting, San Francisco, CA, Dec. 1-5, 2000 (Abstract No. 2485).

Shire et al., "TNF-α inhibitors and rheumatoid arthritis," *Exp. Opin. Ther. Patents* 8(5):531-544, 1998.

Singhal et al., "Antitumor Activity of Thalidomide in Refractory Multiple Myeloma," *The New England Journal of Medicine* 341(21):1565-1571, 1999.

Singhal et al., "Thalidomide in Cancer. Potential Uses and Limitations," *BioDrugs* 15(3):163-172, 2001.

Streetly et al., "Thalidomide analogue CC-4047 is effective in the treatment of patients with relapsed and refractory multiple myeloma (MM) and induces T-cell activation and IL-12 production," International Multiple Myeloma Workshop, IXth International Conference, Salamanca, Spain, May 23-27, 2003 (Abstract No. 367).

Streetly et al., "An Update of the Use and Outcomes of the New Immunomodulatory Agent CC-4047 (Actimid) in Patients with Relapsed/Refractory Myeloma," American Society of Hematology, 45th Annual Meeting, San Diego, CA, Dec. 6-9, 2003 (Abstract No. 829).

Streetly et al., "Changes in Neutrophil Phenotype Following the Administration of CC-4047 (Actimid) to Patients with Multiple Myeloma," American Society of Hematology, 45th Annual Meeting, San Diego, CA, Dec. 6-9, 2003 (Abstract No. 2543).

Suzuki, et al., "Use of a new protecting group in an attempted synthesis of cyclopropyldihydroxyphenylalanine," *Journal of Organic Chemistry* 48(24):4769-4771, 1983.

Teo et al., "Chiral Inversion of the Second Generation IMiD™ CC-4047 (ACTIMID™) in Human Plasma and Phosphate-Buffered Saline," *Chirality* 15:348-351, 2003.

Teubert et al., "5'-Substituted Thalidomide Analogs as Modulators of TNF-α," *Arch. Pharm. Med. Chem.* 331:7-12, 1998.

"The Merck Index," Merck & Co. 2001.

Tweedie et al., "TNF-α Synthesis Inhibitors on the 3-Phthalimidoglutarimide Backbone as Therapeutic Candidates for Neurodegenerative Diseases," 7th *International Conference on Alzheimer's and Parkinson's Disease*, pp. 77-86, Sorrento, Italy, Mar. 9-13, 2005.

Ye et al., "Novel IMiD Drugs Enhance Expansion and Regulate Differentiation of Human Cord Blood CD34+ Cells with Cytokines," American Society of Hematology, 44th Annual Meeting, Philadelphia, PA, Dec. 6-10, 2002 (Abstract No. 4099).

Zeldis et al., "Potential New Therapeutics for Waldenstrom's Macroglobulinemia," *Seminars in Oncology* 30(2):275-281, 2003.

Zeldis et al., "Update on the evolution of the IMiD™," International Society for Biological Therapy of Cancer, 18th Annual Meeting, Bethesda, MD, Oct. 30-Nov. 2, 2003 (Oral Abstract).

Zhang et al., "CC-5079, a novel microtubule and TNF-a inhibitor with anti-angiogenic and antimetastasis activity," American Association for Cancer Research, National Cancer Institute, and European Organization for Research and Treatment of Cancer, International Conference on Molecular Targets and Cancer Therapeutics, Boston, MA, Nov. 17-21, 2003 (Abstract No. B012).

Zhang et al., "Preparation of water-soluble thalidomide derivatives," Database CA Online Chemical Abstracts Service, Database Accession No. 2004:817880, 2004 (Abstract).

Voss, "2,4-Bis(4-methoxyphenyl)-1,3,2,4-dithiadiphosphetane 2,4-Disulfide," *e-EROS Encyclopedia of Reagents for Organic Synthesis*, Sep. 15, 2006.

Park et al., "Synthesis and Structure-Activity Relationships of Novel Compounds for the Inhibition of TNF-α Production," *Arch Pharm Res* 23(4): 332-337, 2000.

* cited by examiner

THALIDOMIDE ANALOGS

CROSS-REFERENCE TO RELATED APPLICATIONS

This is the §371 U.S. National Stage of International Application No. PCT/US2004/030506, filed Sep. 17, 2004, which was published in English under PCT Article 21(2), which in turn claims the benefit of U.S. Provisional Patent Application No. 60/504,724, filed Sep. 17, 2003, which is incorporated by reference herein.

FIELD

The present invention relates to thalidomide analogs, methods of synthesizing the analogs, and methods for using the analogs to modulate angiogenesis and tumor necrosis factor alpha activities in a subject. More particularly, the invention relates to sulfur-containing thalidomide analogs and methods of making and using the same.

BACKGROUND

Thalidomide (N-α-phthalimidoglutarimide) is a glutamic acid derivative that was introduced onto the market as a sedative hypnotic in 1956, but was withdrawn in 1961 due to the development of severe congenital abnormalities in babies born to mothers using it for morning sickness. Interest in the agent was reawakened after thalidomide was found clinically effective in the treatment of erythema nodosum leprosum (ENL) and in the treatment of HIV wasting syndrome and various cancers. Mechanistic studies of its ENL activity demonstrated an anti-tumor necrosis factor alpha (anti-TNF-α) action. Specifically, thalidomide enhances the degradation of TNF-α RNA, and thereby lowers its synthesis and secretion. Further studies have defined it to be a co-stimulator of both CD8+ and CD4+ T cells, an inhibitor of angiogenesis via its inhibitory actions on basic fibroblast growth factor (bFGF) and vascular endothelial growth factor (VEGF), and an inhibitor of the transcription factor, NFκB.

TNF-α and family members play pivotal roles in a variety of physiological and pathological processes, which include cell proliferation and differentiation, apoptosis, the modulation of immune responses and induction of inflammation TNF-α acts via two receptors, TNFR1 and 2. The former is expressed in all tissues and is the predominant signaling receptor for TNF-α. The latter is primarily expressed on immune cells and mediates more limited biological responses. The exposure of cells to TNF-α can result in activation of a caspase cascade leading to cell death via apoptosis. Indeed, major cell surface molecules capable of initiating apoptosis are members of the TNF family of ligands and receptors. For example, death-inducing members of the TNF receptor family each contain a cytoplasmic 'death domain' (DD), which is a protein-protein interaction motif critical for engaging downstream components of the signal transduction machinery.

Recently, TRAIL, the tumor necrosis factor-related apoptosis-inducing ligand, has been shown to selectively induce apoptosis of tumor cells, but not most normal cells. It is indicated that TRAIL mediates thymocyte apoptosis and is important in the induction of autoimmune diseases. More often, however, TNF-α receptor binding induces the activation of transcription factors, AP-1 and NFκB, that thereafter induce genes involved in acute and chronic inflammatory responses. Overproduction of TNF-α has thus been implicated in many inflammatory diseases, such as rheumatoid arthritis, graft-versus-host disease and Crohn's disease, and it additionally exacerbates ENL, septic shock, AIDS and dementia associated with Alzheimer's disease (AD).

A number of thalidomide analogs optimized to reduce TNF-α synthesis have been designed and synthesized. Primarily, these analogs include structural modifications of the phthaloyl ring or glutarimide ring of thalidomide. In addition, following the demonstration that the anti-angiogenic property of thalidomide is associated with its hydroxylated, open-ring metabolites, syntheses of the hydroxylated and hydrolysis metabolites as inhibitors of angiogenesis or tumor metastasis have been reported. Although extensive studies exist regarding the structure-activity relationships between thalidomide and TNF-α, very little is known about the contribution of the four amide carbonyl groups of thalidomide to its biological activity.

SUMMARY

Thalidomide analogs having angiogenesis modulating activity and TNF-α modulating activity are disclosed. In some embodiments, the disclosed thalidomide analogs are sulfur-analogs of thalidomide, its open-ring metabolites and its derivatives (such as its hydroxylated derivatives) in which one or more carbonyl groups are replaced by thiocarbonyl groups. For example, in some embodiments, thalidomide analogs wherein at least one carbonyl group on the pthaloyl moiety or on the glutaramide moiety (or its open ring form) of a thalidomide or a thalidomide analog is replaced by a thiocarbonyl group. In particular embodiments, successive replacement of the carbonyl groups in thalidomide with thiocarbonyl groups provides thiothalidomide analogs having increased TNF-α inhibitory activity. Surprisingly, the increase in TNF-α inhibition due to replacement of the carbonyl groups of thalidomide with thiocarbonyl groups is not associated with toxicity.

Improved methods for making thalidomide and thalidomide analogs are also disclosed, as are methods of converting thalidomide analogs into thiothalidomides. Due to their angiogenesis and TNF-α modulating activity, the disclosed thalidomide analogs, especially the disclosed thiothalidomides, can be used to treat a subject having a disease or condition related to angiogenesis or TNF-α activity, such as a tumor or unwanted neovascularization. Furthermore, the physical and toxicological properties of the disclosed thio-thalidomide analogs make them suitable for potently and safely modulating angiogenesis and TNF-α activity without injection, for example, by oral administration. This is in contrast to many currently available agents used for such purposes.

DETAILED DESCRIPTION OF PARTICULARLY DISCLOSED EMBODIMENTS

Figure 1:
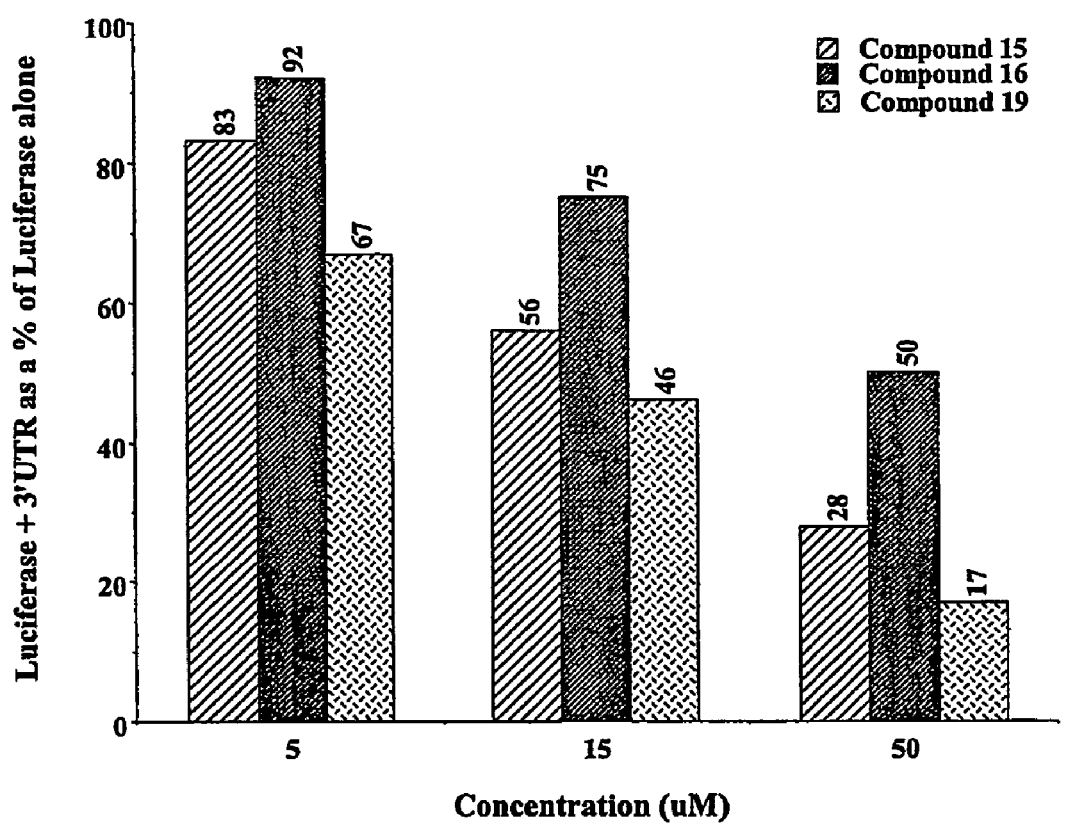
FIG. 1 is a bar graph showing the TNF-α inhibitory action of several disclosed thalidomide analogs in murine cells having a luciferase reporter element plus the 3'-UTR of human TNF-α relative to their action in cells lacking the 3'UTR.

I. Abbreviations
TNF-α—tumor necrosis factor alpha
CDI— carboxyamidotriazole
ARE—adenylate/uridylate (AU)-rich element
UTR—untranslated region
THF—tetrahydrofuran
NMR—nuclear magnetic resonance
LR—Lawesson's Reagent
II. Terms In order to facilitate an understanding of the embodiments presented, the following explanations are provided.

The singular terms "a," "an," and "the" include plural referents unless context clearly indicates otherwise. Similarly, the word "or" is intended to include "and" unless the context clearly indicates otherwise. The term "comprises" means "includes." Also, "comprising A or B" means including A or B, or A and B, unless the context clearly indicates otherwise. It is to be further understood that all molecular weight or molecular mass values given for compounds are approximate, and are provided for description. Although methods and materials similar or equivalent to those described herein can be used in the practice or testing of this disclosure, suitable methods and materials are described below. In addition, the materials, methods, and examples are illustrative only and not intended to be limiting.

The term "subject" refers to animals, including mammals (for example, humans and veterinary animals such as dogs, cats, pigs, horses, sheep, and cattle).

An "R-group" or "substituent" refers to a single atom (for example, a halogen atom) or a group of two or more atoms that are covalently bonded to each other, which are covalently bonded to an atom or atoms in a molecule to satisfy the valency requirements of the atom or atoms of the molecule, typically in place of a hydrogen atom. Examples of R-groups/substituents include alkyl groups, hydroxyl groups, alkoxy groups, acyloxy groups, mercapto groups, and aryl groups.

"Substituted" or "substitution" refer to replacement of a hydrogen atom of a molecule or an R-group with one or more additional R-groups such as halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, nitro, sulfato or other R-groups.

"Alkyl" refers to a cyclic, branched, or straight chain group containing only carbon and hydrogen, and unless otherwise mentioned typically contains one to twelve carbon atoms. This term is further exemplified by groups such as methyl, ethyl, n-propyl, isobutyl, t-butyl, pentyl, pivalyl, heptyl, adamantyl, and cyclopentyl. Alkyl groups can either be unsubstituted or substituted. "Lower alkyl" groups are those that contain one to six carbon atoms.

"Acyl" refers to a group having the structure RCO—, where R may be alkyl, or substituted alkyl. "Lower acyl" groups are those that contain one to six carbon atoms.

"Acyloxy refers to a group having the structure RCOO—, where R may be alkyl or substituted alkyl. "Lower acyloxy" groups contain one to six carbon atoms.

"Alkenyl" refers to a cyclic, branched or straight chain group containing only carbon and hydrogen, and unless otherwise mentioned typically contains one to twelve carbon atoms, and contains one or more double bonds that may or may not be conjugated. Alkenyl groups may be unsubstituted or substituted. "Lower alkenyl" groups contain one to six carbon atoms.

"Alkynyl" refers to a cyclic, branched or straight chain group containing only carbon and hydrogen, and unless otherwise mentioned typically contains one to twelve carbon atoms, and contains one or more triple bonds. Alkynyl groups may be unsubstituted or substituted. "Lower alkynyl" groups are those that contain one to six carbon atoms.

"Alkoxy" refers to a group having the structure R—O—, where R may be alkyl or substituted alkyl. Examples of alkoxy groups include methoxy, ethoxy, propoxy and butoxy groups. "Lower alkoxy" groups are those that contain one to six carbon atoms.

The term "halogen" refers to fluoro, bromo, chloro and iodo substituents.

"Aryl" refers to a monovalent unsaturated aromatic carbocyclic group having a single ring (e.g., phenyl) or multiple condensed rings (e.g., naphthyl or anthryl), which can optionally be unsubstituted or substituted.

The term "amino" refers to an R-group having the structure —$NH_2$, which can be optionally substituted with, for example, lower alkyl groups, to yield an amino group having the general structure —NHR or —$NR_2$.

"Nitro" refers to an R-group having the structure —$NO_2$.

The term "aliphatic" as applied to cyclic groups refers to ring structures in which any double bonds that are present in the ring are not conjugated around the entire ring structure.

The term "aromatic" as applied to cyclic groups refers to ring structures which contain double bonds that are conjugated around the entire ring structure, possibly through a heteroatom such as an oxygen atom or a nitrogen atom. Aryl groups, pyridyl groups and furan groups are examples of aromatic groups. The conjugated system of an aromatic group contains a characteristic number of electrons, for example, 6 or 10 electrons that occupy the electronic orbitals making up the conjugated system, which are typically un-hybridized p-orbitals.

"Pharmaceutical compositions" are compositions that include an amount (for example, a unit dosage) of one or more of the disclosed compounds together with one or more non-toxic pharmaceutically-acceptable excipients, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

A "therapeutically effective amount" of the disclosed compounds is a dosage of the compound that is sufficient to achieve a desired therapeutic effect, such as inhibition of angiogenesis or an anti-tumor or anti-metastatic effect, or inhibition of TNF-α activity. In some examples, a therapeutically effective amount is an amount sufficient to achieve tissue concentrations at the site of action that are similar to those that are shown to modulate angiogenesis or TNF-α activity in tissue culture, in vitro, or in vivo. For example, a therapeutically effective amount of a compound may be such that the subject receives a dosage of about 0.1 µg/kg body weight/day to about 1000 mg/kg body weight/day, for example, a dosage of about 1 µg/kg body weight/day to about 1000 µg/kg body weight/day, such as a dosage of about 5 µg/kg body weight/day to about 500 µg/kg body weight/day.

The term "stereoisomer" refers to a molecule that is an enatiomer, diasteromer or geometric isomer of a molecule. Stereoisomers, unlike structural isomers, do not differ with respect to the number and types of atoms in the molecule's structure but with respect to the spatial arrangement of the molecule's atoms. Examples of stereoisomers include the (+) and (−) forms of optically active molecules.

The term "modulate" refers to the ability of a disclosed compound to alter the amount, degree, or rate of a biological function, the progression of a disease, or amelioration of a condition. For example, modulating can refer to the ability of a compound to elicit an increase or decrease in angiogenesis, to inhibit TNF-α activity, or to inhibit tumor metastasis or tumorigenesis.

The term "angiogenic activity" refers to the ability of a disclosed compound or a particular concentration of a disclosed compound to stimulate angiogenesis. Angiogenic activity may be detected in vivo or in vitro. Angiogenic compounds or angiogenic concentrations of disclosed compounds stimulate angiogenesis, and such compounds and/or concentrations may be readily identified by those of ordinary skill in the art, using, for example, the methods described in the Examples that follow.

The term "anti-angiogenic activity" refers to the ability of a compound or a particular concentration of a disclosed compound to inhibit angiogenesis. Anti-angiogenic activity may be detected in vivo or in vitro. Anti-angiogenic or anti-angiogenic concentrations of disclosed compounds inhibit angiogenesis, and such compounds and/or concentrations may be readily identified by those of ordinary skill in the art, using, for example, the methods described in the Examples that follow.

III. Overview of Particularly Disclosed Embodiments

Disclosed are thalidomide analogs that modulate TNF-α activity and/or angiogenesis, and as such can be used to treat a wide variety of pathological conditions that are linked to angiogenesis and/or TNF-α activity. Pharmaceutically acceptable salts, stereoisomers, and metabolites of all of the disclosed compounds also are contemplated. In some embodiments, the thalidomide analogs are thiothalidomide derivatives in which carbonyl groups in corresponding non-sulfur-containing thalidomide derivatives are replaced by one or more thiocarbonyl groups.

In the structures that follow, all valency requirements are understood to be satisfied. Thus, for example, carbon atoms have four bonds to other atoms, even if all such bonds are not shown. As is understood by those of ordinary skill in the art, where all four bonds to a carbon atom are not shown, additional bonds to hydrogen atoms are implied. Further substitution of such implied hydrogen atoms is possible.

In other embodiments, the disclosed compounds include compounds having the chemical formula:

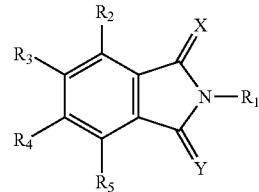

wherein X and Y are independently $CH_2$, oxygen or sulfur, and at least one of X and Y is sulfur if $R_1$ does not include a sulfur atom; each of $R_2$-$R_5$ are independently hydrogen, hydroxyl, acyl, substituted acyl, acyloxy, substituted acyloxy, alkyl, substituted alkyl, alkenyl, substituted alkenyl, alkynyl, substituted alkynyl, alkoxy, substituted alkoxy, aryl, substituted aryl, amino, substituted amino, halogen, nitro or linked to form a five- or six-membered, unsubstituted or substituted, aliphatic, aromatic or heterocyclic ring, for example, hydrogen, lower alkyl, acyloxy, halogen, hydroxyl, amino or nitro such as hydrogen, acyloxy or hydroxyl; and $R_1$ is an unsubstituted or substituted, aliphatic or aromatic heterocyclic ring, an unsubstituted or substituted cycloalkenyl ring, or

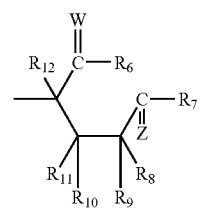

wherein W and Z are each independently oxygen or sulfur, $R_6$ and $R_7$ are each independently hydroxyl, alkoxy or substituted alkoxy, and each of $R_8$-$R_{12}$ are independently hydrogen, hydroxyl, acyl, substituted acyl, acyloxy, substituted acyloxy, alkyl, substituted alkyl, alkenyl, substituted alkenyl, alkynyl, substituted alkynyl, alkoxy, substituted ally, aryl, substituted aryl, amino, substituted amino, halogen or nitro, for example, hydrogen, lower alkyl, acyloxy, halogen, hydroxyl, amino or nitro such as hydrogen, acyloxy or hydroxyl.

In particular embodiments, $R_1$ is

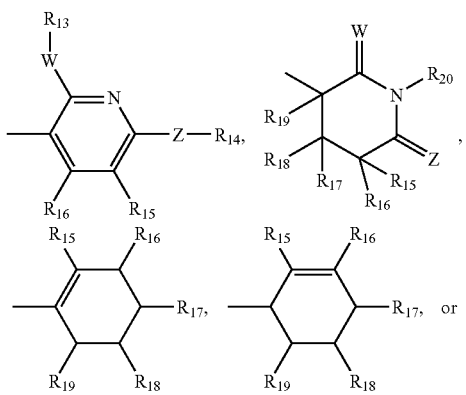

wherein W and Z are each independently oxygen or sulfur, R$_{13}$ and R$_{14}$ are each independently hydrogen, alkyl or substituted alkyl; R$_{20}$ is hydrogen, hydroxyl, alkyl or substituted alkyl such as aryl substituted alkyl; and R$_{15}$-R$_{19}$ are each independently hydrogen, hydroxyl, acyl, substituted acyl, acyloxy, substituted acyloxy, alkyl, substituted alkyl, alkenyl, substituted alkenyl, alkynyl, substituted alkynyl, alkoxy, substituted alkoxy, aryl, substituted aryl, amino, substituted amino, halogen or nitro, for example, hydrogen, lower alkyl, acyloxy, halogen, hydroxyl, amino or nitro such as hydrogen, acyloxy or hydroxyl. In some embodiments, at least one of R$_2$, R$_3$, R$_4$, R$_5$, R$_8$, R$_9$, R$_{10}$, R$_{11}$, R$_{15}$, R$_{16}$, R$_{17}$, R$_{18}$ and R$_{19}$ is hydroxyl. In other embodiments, at least one of X, Y, W and Z is sulfur, at least two of X, Y, W and Z are sulfur, or at least three of X, Y, W and Z are sulfur. For example, in more particular embodiments, X or Y is sulfur, and both W and Z are oxygen if present; both X and Y are sulfur and both W and Z are oxygen if present; X and Y are both oxygen and W or Z is sulfur if present; both X and Y are sulfur and W or Z is sulfur if present; or X or Y are sulfur and both W and Z are sulfur if present. Alternatively, where W and Z are present the following are possible: X=S, Y=O, W=O, Z=O; X=O, Y=S, W=O, Z=O; X=O, Y=O, W=S, Z=O; X=O, Y=O, W=O, Z=S; X=S, Y=S, W=O, Z=O; X=S, Y=O, W=S, Z=O; X=S, Y=O, W=O, Z=S; X=O, Y=O, W=S, Z=S; X=O, Y=S, W=O, Z=S; X=O, Y=S, W=S, Z=O; X=S, Y=S, W=S, Z=O; X=O, Y=S, W=S, Z=S; X=S, Y=O, W=S, Z=S; X=S, Y=S, W=O, Z=S; X=S, Y=S, W=S, Z=S; or X=S, Y=S, W=S, Z=S. In other particular embodiments X=S and Y=CH$_2$.

In more particular embodiments, the disclosed compounds have the formula wherein X, Y, W and Z are independently sulfur or oxygen and at least one of X, Y, W and Z is sulfur, and R$_2$-R$_{12}$ are as before. For example, in more particular embodiments, X or Y is sulfur, and both W and Z are oxygen if present; both X and Y are sulfur and both W and Z are oxygen if present; X and Y are both oxygen and W or Z is sulfur if present; both X and Y are sulfur and W or Z is sulfur if present; or X or Y are sulfur and both W and Z are sulfur if present. Alternatively, where W and Z are present the following are possible: X=S, Y=O, W=O, Z=O; X=O, Y=S, W=O, Z=O; X=O, Y=O, W=S, Z=O; X=O, Y=O, W=O, Z=S; X=S, Y=S, W=O, Z=O; X=S, Y=O, W=S, Z=O; X=S, Y=O, W=O, Z=S; X=O, Y=O, W=S, Z=S; X=O, Y=S, W=O, Z=S; X=O, Y=S, W=S, Z=O; X=S, Y=S, W=S, Z=O; X=O, Y=S, W=S, Z=S; X=S, Y=O, W=S, Z=S; X=S, Y=S, W=O, Z=S; X=S, Y=S, W=S, Z=S; or X=S, Y=S, W=S, Z=S. In more particular embodiments, at least one of R$_2$-R$_5$ and R$_8$-R$_{11}$ is hydroxyl. Specific examples of such compounds include:

In other more particular embodiments, the disclosed compounds have the chemical formula:

wherein W, X, Y and Z each are independently sulfur or oxygen and at least one of W, X, Y and Z is sulfur; and R$_2$-R$_5$ and R$_{15}$-R$_{20}$ are as before. For example, in more particular embodiments, X or Y is sulfur, and both W and Z are oxygen; both X and Y are sulfur and both W and Z are oxygen; X and Y are both oxygen and W or Z is sulfur; both X and Y are sulfur and W or Z is sulfur; or X or Y are sulfur and both W and Z are sulfur. Alternatively, the following are possible: X=S, Y=O, W=O, Z=O; X=O, Y=S, W=O, Z=O; X=O, Y=O, W=S, Z=O; X=O, Y=O, W=O, Z=S; X=S, Y=S, W=O, Z=O; X=S, Y=O, W=S, Z=O; X=S, Y=O, W=O, Z=S; X=O, Y=O, W=S, Z=S; X=O, Y=S, W=O, Z=S; X=O, Y=S, W=S, Z=O; X=S, Y=S, W=S, Z=O; X=O, Y=S, W=S, Z=S; X=S, Y=O, W=S, Z=S; X=S, Y=S, W=O, Z=S; X=S, Y=S, W=S, Z=S; or X=S, Y=S, W=S, Z=S. In more particular embodiments, at least one of R$_2$-R$_5$ and R$_{15}$-R$_{19}$ is hydroxyl. Specific examples of such compounds include:

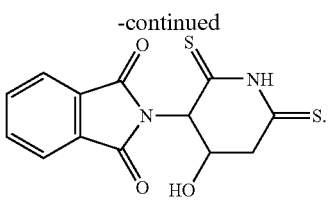

The disclosed compounds also include compounds having the formula

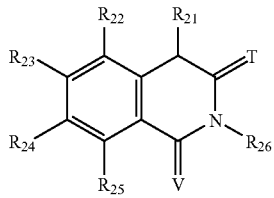

wherein T and V are independently oxygen or sulfur, $R_{21}$-$R_{25}$ are independently hydrogen, hydroxyl, acyl, substituted acyl, acyloxy, substituted acyloxy, alkyl, substituted alkyl, alkenyl, substituted alkenyl, alkynyl, substituted alkynyl, alkoxy, substituted alkoxy, aryl, substituted aryl, amino, substituted amino, halogen or nitro, for example, hydrogen, lower alkyl, acyloxy, halogen, hydroxyl, amino or nitro such as hydrogen, acyloxy or hydroxyl; and $R_{26}$ is

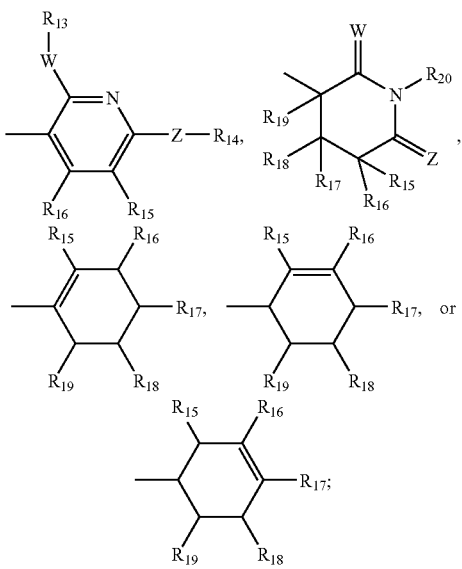

wherein W, Z and $R_{13}$-$R_{20}$ are as before. For example, in more particular embodiments, T or V is sulfur, and both W and Z are oxygen if present; both T and V are sulfur and both W and Z are oxygen if present; T and V are both oxygen and W or Z is sulfur if present; both T and V are sulfur and W or Z is sulfur if present; or T or V are sulfur and both W and Z are sulfur if present. Alternatively, where W and Z are present the following are possible: T=O, V=O, W=O, Z=O; T=S, V=O, W=O, Z=O; T=O, V=S, W=O, Z=O; T=O, V=O, W=S, Z=O; T=O, V=O, W=O, Z=S; T=S, V=S, W=O, Z=O; T=S, V=O, W=S, Z=O; T=S, V=O, W=O, Z=S; T=O, V=S, W=S, Z=O; T=O, V=S, W=O, Z=S; T=O, V=O, W=S, Z=S; T=S, V=S, W=O, Z=S; T=O, V=S, W=S, Z=S; T=S, V=O, W=S, Z=S; T=S, V=S, W=S, Z=O; T=S, V=S, W=S, Z=S; T=S, V=O, W=O, Z=S; T=S, V=O, W=S, Z=S; T=O, V=S, W=S, Z=S; T=O, V=S, W=S, Z=S; or T=S, V=S, W=S, Z=S. In some embodiments, at least one of $R_{15}$-$R_{19}$ and $R_{22}$-$R_{26}$ is hydroxyl.

Still further, the disclosed compounds include compounds having the formula

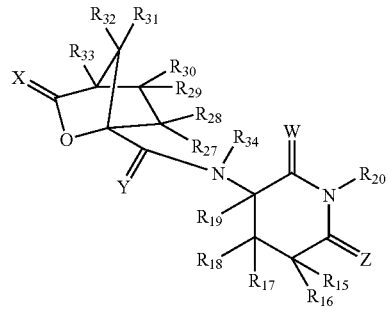

wherein X, Y are each independently oxygen or sulfur, W, X and $R_{15}$-$R_{20}$ are as before; $R_{27}$-$R_{33}$ are each independently hydrogen, hydroxyl, acyl, substituted acyl, acyloxy, substituted acyloxy, alkyl, substituted alkyl, alkenyl, substituted alkenyl, alkynyl, substituted alkynyl, alkoxy, substituted alkoxy, aryl, substituted aryl, amino, substituted amino, halogen or nitro, for example, hydrogen, lower alkyl, acyloxy, halogen, hydroxyl, amino or nitro such as hydrogen, acyloxy or hydroxyl; and $R_{34}$ is hydrogen, alkyl or substituted alkyl. For example, in more particular embodiments, X or Y is sulfur, and both W and Z are oxygen; both X and Y are sulfur and both W and Z are oxygen; X and Y are both oxygen and W or Z is sulfur; both X and Y are sulfur and W or Z is sulfur; or X or Y are sulfur and both W and Z are sulfur. Alternatively, the following are possible: X=O, Y=O, W=O, Z=O; X=S, Y=O, W=O, Z=O; X=O, Y=S, W=O, Z=; X=O, Y=O, W=S, Z=O; X=O, Y=O, W=O, Z=S; X=S, Y=S, W=O, Z=O; X=S, Y=O, W=S, Z=O; X=S, Y=O, W=O, Z=S; X=O, Y=S, W=S, Z=S; X=O, Y=O, W=S, Z=S; X=O, Y=S, W=O, Z=S; X=O, Y=S, W=S, Z=O; X=S, Y=S, W=S, Z=O; X=S, Y=S, W=O, Z=S; X=S, Y=O, W=S, Z=S; X=O, Y=S, W=S, Z=S; or X=S, Y=S, W=S, Z=S.

In addition, the disclosed compounds include compounds having the formula

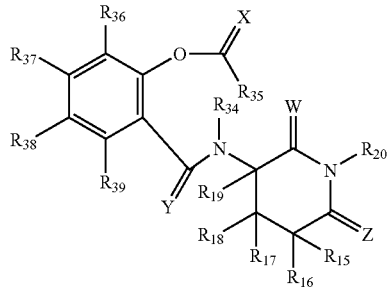

wherein X and Y are each independently oxygen or sulfur; W, Z, $R_{15}$-$R_{20}$ and $R_{34}$ are as before, $R_{35}$ is alkyl or substituted alkyl, and $R_{36}$-$R_{39}$ are each independently hydrogen, hydroxyl, acyl, substituted acyl, acyloxy, substituted acyloxy, alkyl, substituted alkyl, alkenyl, substituted alkenyl, alkynyl, substituted alkynyl, alkoxy, substituted alkoxy, aryl, substituted aryl, amino, substituted amino, halogen or nitro, for example, hydrogen, lower alkyl, acyloxy, halogen, hydroxyl, amino or nitro such as hydrogen, acyloxy or hydroxyl. For example, in more particular embodiments, X or Y is sulfur, and both W and Z are oxygen; both X and Y are sulfur and both W and Z are oxygen; X and Y are both oxygen and W or Z is sulfur; both X and Y are sulfur and W or Z is sulfur; or X or Y are sulfur and both W and Z are sulfur. Alternatively, the following are possible: X=O, Y=O, W=O, Z=O; X=S, Y=O, W=O, Z=O; X=O, Y=S, W=O, Z=O; X=O, Y=O, W=S, Z=O; X=O, Y=O, W=O, Z=S; X=S, Y=S, W=O, Z=O; X=S, Y=O, W=S, Z=O; X=S, Y=O, W=O, Z=S; X=O, Y=S, W=S, Z=O; X=O, Y=S, W=O, Z=S; X=O, Y=O, W=S, Z=S; X=S, Y=S, W=S, Z=O; X=S, Y=S, W=O, Z=S; X=S, Y=O, W=S, Z=S; X=O, Y=S, W=S, Z=S; or X=S, Y=S, W=S, Z=S.

Other embodiments include compounds having the formula

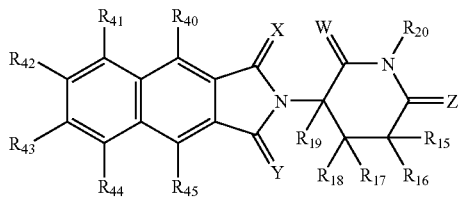

wherein X and Y each are independently oxygen or sulfur; W, Z and $R_{15}$-$R_{20}$ are as before; and $R_{40}$-$R_{45}$ are each independently hydrogen, hydroxyl, acyl, substituted acyl, acyloxy, substituted acyloxy, alkyl, substituted alkyl, alkenyl, substituted alkenyl, alkynyl, substituted alkynyl, alkoxy, substituted alkoxy, aryl, substituted aryl, amino, substituted amino, halogen or nitro, for example, hydrogen, lower alkyl, acyloxy, halogen, hydroxyl, amino or nitro such as hydrogen, acyloxy or hydroxyl. For example, in more particular embodiments, X or Y is sulfur, and both W and Z are oxygen; both X and Y are sulfur and both W and Z are oxygen; X and Y are both oxygen and W or Z is sulfur; both X and Y are sulfur and W or Z is sulfur; or X or Y are sulfur and both W and Z are sulfur. Alternatively, the following are possible: X=O, Y=O, W=O, Z=O; X=S, Y=O, W=O, Z=O; X=O, Y=S, W=O, Z=O; X=O, Y=O, W=S, Z=O; X=O, Y=O, W=O, Z=S; X=S, Y=S, W=O, Z=O; X=S, Y=O, W=S, Z=O; X=S, Y=O, W=O, Z=S; X=O, Y=S, W=S, Z=O; X=O, Y=S, W=O, Z=S; X=O, Y=O, W=S, Z=S; X=S, Y=S, W=S, Z=O; X=S, Y=S, W=O, Z=S; X=S, Y=O, W=S, Z=S; X=O, Y=S, W=S, Z=S; or X=S, Y=S, W=S, Z=S.

The disclosed compounds further include compounds having the formula

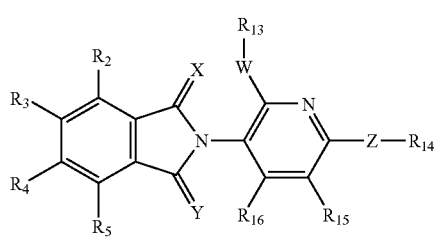

wherein X Y, W and Z are independently oxygen or sulfur, and $R_2$-$R_5$ and $R_{13}$-$R_{16}$ are as before. For example, in more particular embodiments, X or Y is sulfur, and both W and Z are oxygen; both X and Y are sulfur and both W and Z are oxygen; X and Y are both oxygen and W or Z is sulfur; both X and Y are sulfur and W or Z is sulfur; or X or Y are sulfa and both W and Z are sulfur. Alternatively, the following are possible: X=O, Y=O, W=O, Z=O; X=S, Y=O, W=O, Z=O; X=O, Y=S, W=O, Z=O; X=O, Y=O, W=S, Z=O; X=O, Y=O, W=O, Z=S; X=S, Y=S, W=O, Z=O; X=S, Y=O, W=S, Z=O; X=S, Y=O, W=O, Z=S; X=O, Y=S, W=S, Z=O; X=O, Y=S, W=O, Z=S; X=O, Y=O, W=S, Z=S; X=S, Y=S, W=S, Z=O; X=S, Y=S, W=O, Z=S; X=S, Y=O, W=S, Z=S; X=O, Y=S, W=S, Z=S; or X=S, Y=S, W=S, Z=S.

Also disclosed is a thalidomide analog compound having the formula

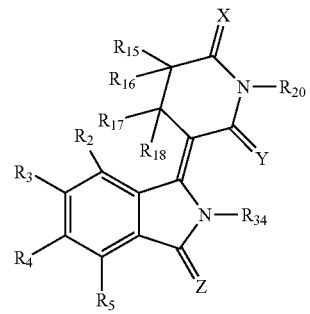

wherein X, Y and Z are independently oxygen or sulfur, and $R_2$-$R_5$, $R_{15}$-$R_{20}$ and $R_{34}$ are as before. For example, in more particular embodiments, X or Y is sulfur, and Z is oxygen; both X and Y are sulfur and Z is oxygen; X and Y are both oxygen and Z is sulfur. Alternatively, the following are possible: X=O, Y=O, Z=O; X=S, Y=O, Z=O; X=O, Y=S, Z=O; X=O, Y=O, Z=S; X=S, Y=S, Z=O; X=S, Y=O, Z=S; X=O, Y=S, Z=S; or X=S, Y=S, Z=S.

Also disclosed is a thalidomide analog compound having the formula

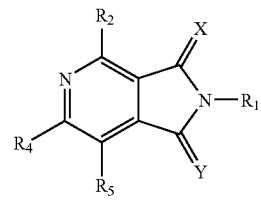

wherein X and Y are independently oxygen or sulfur, and $R_1$, $R_2$, $R_4$ and $R_5$ are as before. For example, in particular embodiments, $R_1$ is

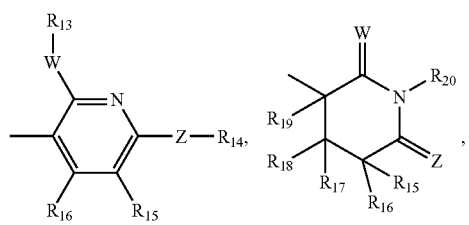

-continued

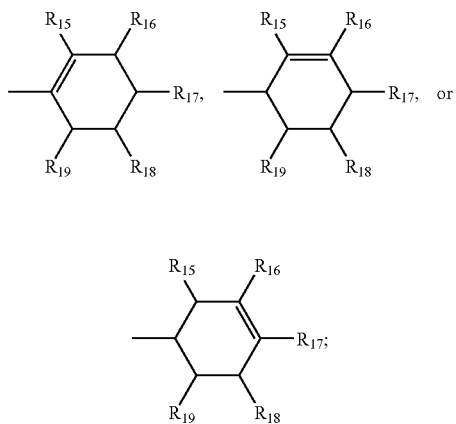

wherein W, Z, and $R_{13}$-$R_{20}$ are as before. For example, in more particular embodiments, X or Y is sulfur, and both W and Z are oxygen if present; both X and Y are sulfur and both W and Z are oxygen if present; X and Y are both oxygen and W or Z is sulfur if present; both X and Y are sulfur and W or Z is sulfur if present; or X or Y are sulfur and both W and Z are sulfur if present. Alternatively, where W and Z are present the following are possible: X=O, Y=O, W=O, Z=O; X=S, Y=O, W=O, Z=O; X=O, Y=S, W=O, Z=O; X=O, Y=O, W=S, Z=O; X=O, Y=O, W=O, Z=S; X=S, Y=S, W=O, Z=O; X=S, Y=O, W=S, Z=O; X=S, Y=O, W=O, Z=S; X=O, Y=O, W=S, Z=S; X=O, Y=S, W=S, Z=O; X=S, Y=S, W=O, Z=S; X=S, Y=S, W=S, Z=O; X=S, Y=S, W=O, Z=S; Y=O, W=S, Z=S; X=O, Y=S, W=S, Z=S; or X=S, Y=S, W=S, Z=S. In more particular embodiments, the compound has the formula:

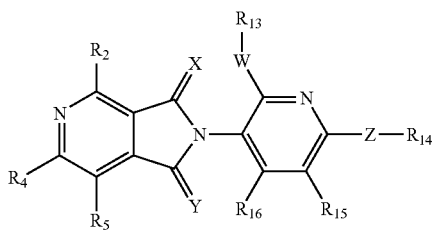

wherein X, Y are independently oxygen or sulfur, and W, Z, $R_2$, $R_4$, $R_5$, and $R_{13}$-$R_{16}$ are as before. For example, in more particular embodiments, X or Y is sulfur, and both W and Z are oxygen; both X and Y are sulfur and both W and Z are oxygen; X and Y are both oxygen and W or Z is sulfur; both X and Y are sulfur and W or Z is sulfur; or X or Y are sulfur and both W and Z are sulfur. Alternatively, the following are possible: X=O, Y=O, W=O, Z=O; X=S, Y=O, W=O, Z=O; X=O, Y=S, W=O, Z=O; X=O, Y=O, W=S, Z=O; X=O, Y=O, W=O, Z=S; X=S, Y=S, W=O, Z=O; X=S, Y=O, W=S, Z=O; X=S, Y=O, W=O, Z=S; X=O, Y=O, W=S, Z=S; X=O, Y=S, W=S, Z=O; X=O, Y=S, W=O, Z=S; X=S, Y=S, W=S, Z=O; X=S, Y=S, W=O, Z=S; X=S, Y=O, W=S, Z=S; X=O, Y=S, W=S, Z=S; or X=S, Y=S, W=S, Z=S. In even more particular embodiments, at least one of $R_2$, $R_4$, $R_5$, $R_{15}$ and $R_{16}$ is hydroxyl.

Also disclosed is a compound having the formula:

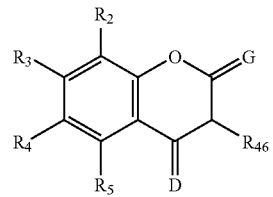

wherein G and D are each independently oxygen or sulfur, $R_2$-$R_5$ are as before, and $R_{46}$ is

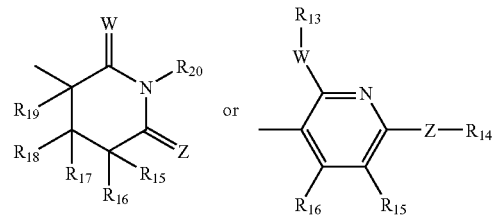

wherein W, Z and $R_{13}$-$R_{20}$ are as before. For example, in particular embodiments, G or D is sulfur, and both W and Z are oxygen; both G and D are sulfur and both W and Z are oxygen; G and D are both oxygen and W or Z is sulfur; both G and D are sulfur and W or Z is sulfur; or G or D are sulfur and both W and Z are sulfur. Alternatively, the following are possible: G=O, D=O, W=O, Z=O; G=S, D=O, W=O, Z=O; G=O, D=S, W=O, Z=O; G=O, D=O, W=S, Z=O; G=O, D=O, W=O, Z=S; G=S, D=S, W=O, Z=O; G=S, D=O, W=S, Z=O; G=S, D=O, W=O, Z=S; G=O, D=O, W=S, Z=S; G=O, D=S, W=S, Z=O; G=O, D=S, W=O, Z=S; G=S, D=S, W=S, Z=O; G=S, D=S, W=O, Z=S; G=S, D=O, W=S, Z=S; G=O, D=S, W=S, Z=S; or G=S, D=S, W=S, Z=S.

A method for modulating TNF-α activity in a subject also is disclosed. The method includes administering to the subject a therapeutically effective amount of one or more of any of the compounds disclosed above, or a compound having the formula:

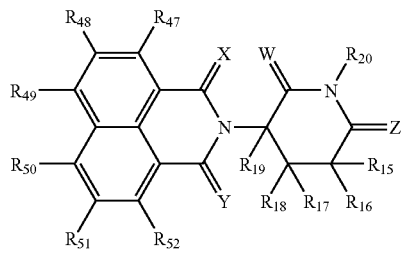

where X and Y are independently oxygen or sulfur; W, Z, $R_{15}$-$R_{20}$ are as before; and $R_{47}$-$R_{52}$ are each independently hydrogen, hydroxyl, acyl, substituted acyl, acyloxy, substituted acyloxy, alkyl, substituted alkyl, alkenyl, substituted alkenyl, alkynyl, substituted alkynyl, alkoxy, substituted alkoxy, aryl, substituted aryl, amino, substituted amino, halogen or nitro, for example, hydrogen, lower alkyl, acyloxy, halogen, hydroxyl, amino or nitro such as hydrogen, acyloxy or hydroxyl;

or a compound having the formula

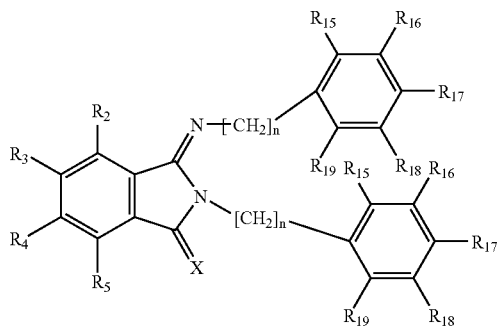

wherein n=1-5; X is oxygen or sulfur, and $R_2$-$R_5$ and $R_{15}$-$R_{19}$ are as before;
or a compound having the formula:

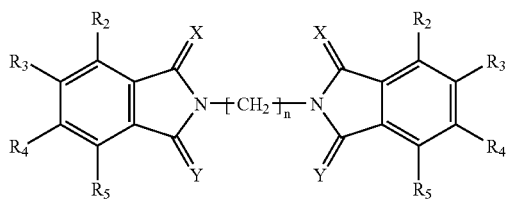

wherein each of X and Y are independently oxygen or sulfur, n=1-5, and $R_2$-$R_5$ are as before;
or a compound having the formula:

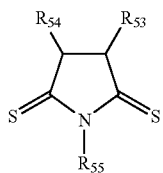

wherein $R_{53}$ and $R_{54}$ are independently hydrogen, hydroxyl, acyl, substituted acyl, acyloxy, substituted acyloxy, alkyl, substituted alkyl, alkenyl, substituted alkenyl, alkynyl, substituted alkynyl, alkoxy, substituted alkoxy, aryl, substituted aryl, amino, substituted amino, halogen or nitro, for example, hydrogen, lower alkyl, acyloxy, halogen, hydroxyl, amino or nitro such as hydrogen, acyloxy or hydroxyl; and $R_{55}$ is hydrogen, alkyl, or substituted alkyl; or a compound having the formula:

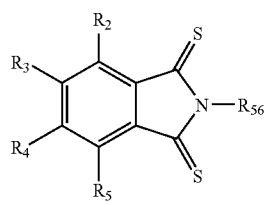

wherein $R_2$-$R_5$ are as before and $R_{56}$ is hydrogen, alkyl or substituted alkyl;
or pharmaceutically acceptable salts or stereoisomers thereof.

Novel thio-substituted analogs having the structures described with respect to the method above also are contemplated. For example, in more particular embodiments, X or Y is sulfur, and both W and Z are oxygen if present; both X and Y are sulfur and both W and Z are oxygen if present; X and Y are both oxygen and W or Z is sulfur if present; both X and Y are sulfur and W or Z is sulfur if present; or X or Y are sulfur and both W and Z are sulfur if present. Alternatively, if W and Z are present, the following are possible: X=O, Y=O, W=O, Z=O; X=S, Y=O, W=O, Z=O; X=O, Y=S, W=O, Z=O; X=O, Y=O, W=S, Z=O; X=O, Y=O, W=O, Z=S; X=S, Y=S, W=O, Z=O; X=S, Y=O, W=S, Z=O; X=S, Y=O, W=O, Z=S; X=O, Y=S, W=O, Z=S; X=O, Y=S, W=S, Z=O; X=O, Y=S, W=S, Z=O; X=S, Y=S, W=O, Z=S; X=S, Y=S, W=S, Z=O; X=S, Y=S, W=O, Z=S; X=O, Y=S, W=S, Z=S; X=S, Y=O, W=S, Z=S; X=O, Y=S, W=S, Z=S; W=S, Z=S; or X=S, Y=S, W=S, Z=S.

Particularly disclosed compounds and compounds that can be used in the disclosed methods include one or more compounds having the following structures:

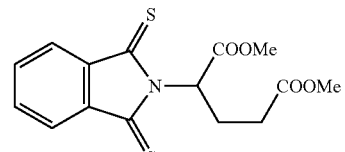

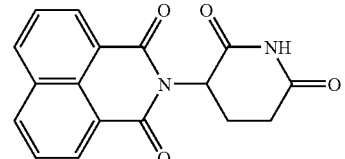

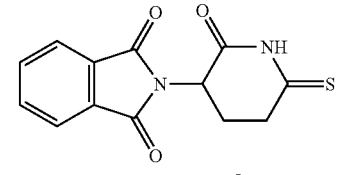

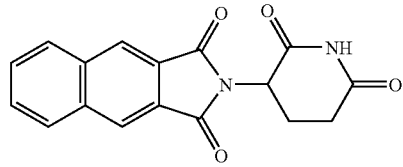

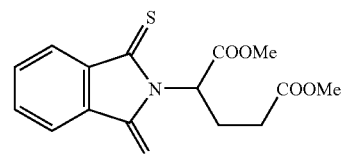

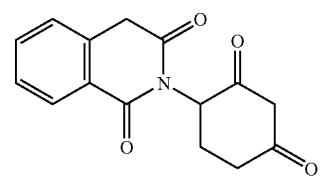

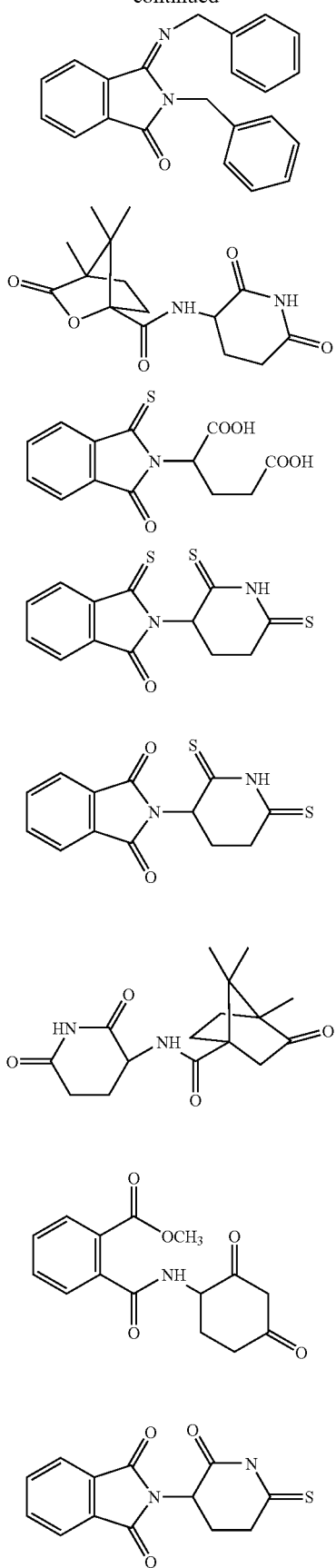
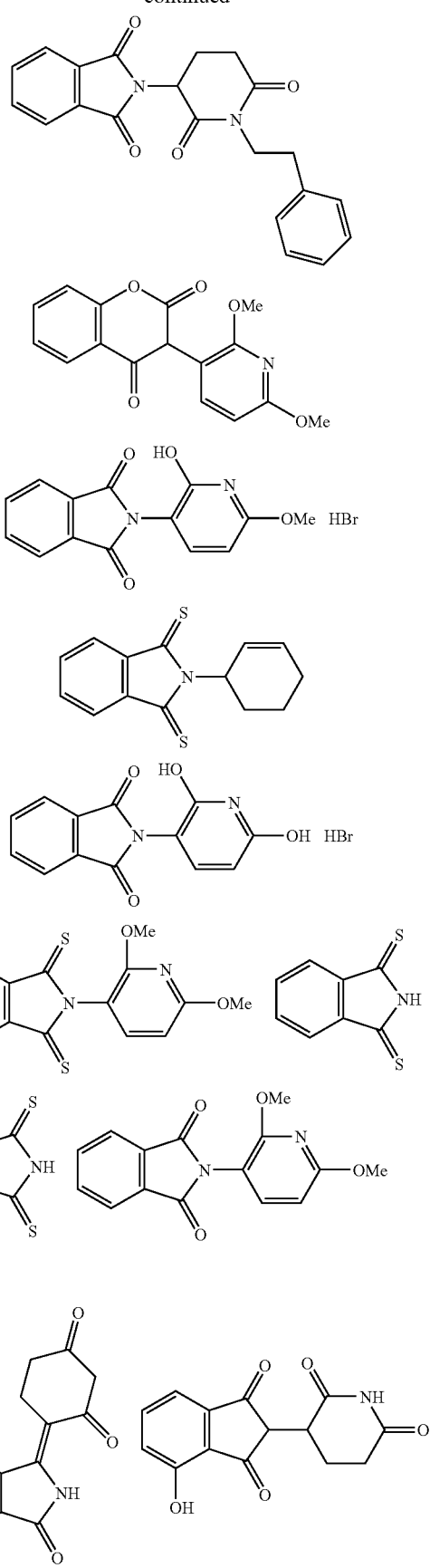

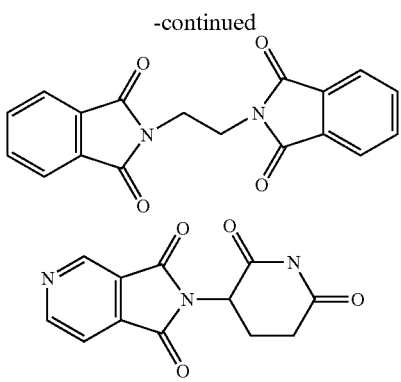

Still further, a method for modulating angiogenesis in a subject is disclosed. The method includes administering to the subject a therapeutically effective amount of one or more of any of the disclosed compounds. Examples of compounds useful for the method are shown above. In some embodiments, where an anti-angiogenic compound or an anti-angiogenic concentration of a compound is utilized, the therapeutically effective amount of the compound can be administered to a subject with a tumor to achieve an anti-tumor effect, such as inhibition of tumorigenesis or tumor metastasis. In other embodiments, the therapeutically effective amount of the compound is administered to a subject with a pathological angiogenesis. Alternatively, where stimulation of angiogenesis is desired an angiogenic compound or an angiogenic concentration of a compound is administered to a subject to stimulate angiogenesis.

As angiogenesis inhibitors, the disclosed compounds are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, these compounds may be useful in the prevention of metastases from the tumors described above either when used alone or in combination with radiotherapy and/or other chemotherapeutic agents.

Further uses of disclosed anti-angiogenic compounds/concentrations include the treatment and prophylaxis of autoimmune diseases such as rheumatoid, immune and degenerative arthritis. Such compounds can also be used to treat a pathological (i.e. abnormal, harmful or undesired) angiogenesis, for example, various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemagiomas, and capillary proliferation within atherosclerotic plaques; Osler-Webber Syndrome; myocardial angiogenesis; plaque neovascularization; telangiectasia; hemophiliac joints; angiofibroma; and wound granulation. Other uses include the treatment of diseases characterized by excessive or abnormal stimulation of endothelial cells, including but not limited to intestinal adhesions, Crohn's disease, atherosclerosis, scleroderma, and hypertrophic scars, such as keloids. Another use is as a birth control agent, by inhibiting ovulation and establishment of the placenta. The disclosed compounds are also useful in the treatment of diseases that have angiogenesis as a pathologic consequence such as cat scratch disease (Rochele minalia quintosa) and ulcers (*Helicobacter pylori*). The disclosed compounds are also useful to reduce bleeding by administration prior to surgery, especially for the treatment of resectable tumors.

Angiogenic compounds or angiogenic concentrations of disclosed compound can be used can be used to treat a variety of conditions that would benefit from stimulation of angiogenesis, stimulation of vasculogenesis, increased blood flow, and/or increased vascularity. Particular examples of conditions and diseases amenable to treatment using disclosed angiogenic compounds, or angiogenic concentrations of disclosed compounds, include any condition associated with an obstruction of a blood vessel, such as obstruction of an artery, vein, or of a capillary system. Specific examples of such conditions or disease include, but are not necessarily limited to, coronary occlusive disease, carotid occlusive disease, arterial occlusive disease, peripheral arterial disease, atherosclerosis, myointimal hyperplasia (such as due to vascular surgery or balloon angioplasty or vascular stenting), thromboangiitis obliterans, thrombotic disorders, vasculitis, and the like. Examples of conditions or diseases that may be prevented using the disclosed angiogenic compounds/concentrations include, but are not limited to, heart attack (myocardial infarction) or other vascular death, stroke, death or loss of limbs associated with decreased blood flow, and the like. Other therapeutic uses for angiogenesis stimulation according to the disclosure include, but are not necessarily limited to accelerating healing of wounds or ulcers; improving the vascularization of skin grafts or reattached limbs so as to preserve their function and viability; improving the healing of surgical anastomoses (such as in reconnecting portions of the bowel after gastrointestinal surgery); and improving the growth of skin or hair.

Yet further, a method for inhibiting TNF-α activity in a subject using the disclosed compounds is provided. The method includes administering a therapeutically effective amount of a disclosed compound to a subject to achieve a TNF-α inhibitory effect. The disclosed compounds having TNF-α inhibitory effects are useful for treating many inflammatory, infectious, immunological, and malignant diseases. These include but are not limited to septic shock, sepsis, endotoxic shock, hemodynamic shock and sepsis syndrome, post ischemic reperfusion injury, malaria, mycobacterial infection, meningitis, psoriasis and other dermal diseases, congestive heart failure, fibrotic disease, cachexia, graft rejection, cancer, tumor growth, undesirable angiogenesis, autoimmune disease, opportunistic infections in ADS, rheumatoid arthritis, rheumatoid spondylitis, osteoarthritis, other arthritic conditions, inflammatory bowel disease, Crohn's disease, ulcerative colitis, multiple sclerosis, systemic lupus erythrematosis, ENL in leprosy, radiation damage, and hyperoxic alveolar injury. In addition, the compounds can be used to treat other neurodegenerative diseases as exemplified by Alzheimer's disease, Parkinson's disease, head trauma, stroke and ALS.

The disclosed compounds can be used in combination with other compositions and procedures for the treatment of diseases. For example, a tumor can be treated conventionally with surgery, radiation or chemotherapy in combination with an anti-angiogenic compound/concentration and then, optionally the compound/concentration can be further administered to the subject to extend the dormancy of micrometastases and to stabilize and inhibit the growth of any residual primary tumor. Alternatively, an angiogenic compound or angiogenic concentration of a compound can be used in combination with other angiogenesis stimulating agents. For example, thermal energy (in the form of resistive heating, laser energy or both) to create thermally treated stimulation zones or pockets (optionally interconnected, at least initially, by small channels) in the tissue for the introduction of blood born growth and healing factors, along with stimulated capillary growth surrounding the thermally treated zone. Such simulation zones allow increased blood flow to previously ischemic and/or nonfunctional tissue (such as cardiac tissue) with a concomitant increased supply of oxygen and nutrients ultimately resulting in a revitalization of the treated sections the tissue when used in combination with the angiogenic compositions/concentrations. In other embodiments, disclosed compounds exhibiting TNF-α inhibitory activity can be combined with other TNF-α inhibitory agents, for example, steroids such as dexamethasone and prednisolone. When used for treatment of a cancer, the compounds can be used in combination with chemotherapeutic agents and/or radiation and/or surgery.

Examples of other chemotherapeutic agents that can be used in combination with the disclosed compounds include alkylating agents, antimetabolites, natural products, kinase inhibitors, hormones and their antagonists, and miscellaneous other agents. Examples of alkylating agents include nitrogen mustards (such as mechlorethamine, cyclophosphamide, melphalan, uracil mustard or chlorambucil), alkyl sulfonates (such as busulfan), and nitrosoureas (such as carmustine, lomustine, semustine, streptozocin, or dacarbazine). Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of kinase inhibitors include small molecule inhibitors (such as Iressa, Tarceva, PKI-166, CI-1033, CGP-5923A, EKB-569, TAK165, GE-572016, CI-1033, SU5416, ZD4190, PTK787/ZK222584, CGP41251, CEP-5214, ZD6474, BIBF1000, VGA1102, SU6668, SU11248, CGP-57148, tricyclic quinoxalines, SU4984, SU5406, Gleevec, NSC680410, PD166326, PD1173952, CT53518, GTP14564, PKC412, PP1, PD116285, CGP77675, CGP76030, CEP-701, and CEP2583), ligand modulators (such as Bevacizumanb, MV833, Soluble Flt-1 and Flk-1, VEGF Trap, GFB 116, NM3, VEGF 121-diptheria toxin conjugate and Interfereon-α), and monoclonal antibodies against receptors (such as Cetuximab, ABX-EGF, Y10, MDX-447, h-R3, EMD 72000, herceptin, MDX-H210, pertuzumab, IMC-1C11, and MF1). Examples of hormones and antagonists include adrenocorticosteroids (such as prednisone), progestins (such as hydrox-yprogesterone caproate, medroxyprogesterone acdtate, and magestrol acetate), estrogens (such as diethylstilbestrol and ethinyl estradiol), antiestrogens (such as tamoxifen), and androgens (such as testerone proprionate and fluoxymesterone). Examples of miscellaneous agents include platinum coordination complexes (such as cis-diamine-dichloroplatinum II, which is also known as cisplatin), substituted ureas (such as hydroxyurea), methyl hydrazine derivatives (such as procarbazine), vaccines (such as APC8024), AP22408, B43-genistein conjugate, paclitaxel, AG538, and adrenocrotical suppressants (such as mitotane and aminoglutethimide). In addition, the disclosed compounds can be combined with gene therapy approaches, such as those targeting VEGF/VEGFR (including antisense oligonucleotide therapy, Adenovirus-based Flt-1 gene therapy, Retrovirus-base Flk-1 gene therapy, Retrovirus-based VHL gene therapy, and angiozyme) and IGF-1R (including INX-4437). Examples of the most commonly used chemotherapy drugs that can be used in combination with the disclosed tricyclic compounds agent include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol, Velban, Vincristine, VP-16, Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

The disclosed compounds also can be combined with radiotherapy employing radioisotopes (such as $^{32}P$, $^{90}Y$, $^{125}I$, $^{131}I$, and $^{177}Lu$), particle beams (such as proton, neutron and electron beams) and electromagnetic radiation (such as gamma rays, x-rays and photodynamic therapy using photosensitizers and visible or ultraviolet rays).

Additionally, the disclosed compounds can be combined with pharmaceutically acceptable excipients, and optionally sustained-release matrices, such as biodegradable polymers, to form therapeutic compositions. Therefore, also disclosed are pharmaceutical compositions including one or more of any of the compounds disclosed above and a pharmaceutically acceptable carrier. The composition may comprise a unit dosage form of the composition, and may further comprise instructions for administering the composition to a subject to inhibit angiogenesis, for example, instructions for administering the composition to achieve an anti-tumor effect or to inhibit a pathological angiogenesis. In particular embodiments, the pharmaceutical composition may comprise one or more of 1-Thioxo-3-oxo-2-(2-oxo-6-thioxopiperidin-3-yl)isoindoline, 1,3-Dioxo-2-(2,6-dithioxopiperidin-3-yl)isoindoline, 1-Thioxo-3-oxo-2-(2,6-dithioxopiperidin-3-yl)isoindoline, N-(2,6-dioxopiperidin-3-yl)-2,3-naphthalenedicarboxamide, 1,3-Dioxo-2-(2,6-dioxopiperidin-3-yl)-5-azaisoindoline, 1,3-Dioxo-2-(1-phenethyl-2,6-dioxopiperidin-3-yl)isoindoline, 2-Acetoxy-N-(2,6-dioxopiperidin-3-yl)benzamide, 2-(2-Oxo-6-thioxo-3-piperidinyl)-1H-isoindole-1,3(2H)-dione, Dimethyl 2-(1,3-dihydro-1-oxo-3-thioxo-2H-isoindol-2-yl)-pentanedioate, Dimethyl 2-(1,3-dihydro-1,3-dithioxo-2H-isoindol-2-yl)-pentanedioate, 2-(1,3-Dihydro-1-oxo-3-thioxo-2H-isoindol-2-yl)-pentanedioic acid, 2,3-Dihydro-3-thioxo-2-(2,6-dioxo-3-piperidinyl)-1H-isoindol-1-one, 2-(2,6-Dithioxo-3-piperidinyl)-1H-isoindole-1,3(2H)-dione, 2,3-Dihydro-3-thioxo-2-(2-oxo-6-thioxo-3-piperidinyl)-1H-isoindol-1-one, 2,3-Dihydro-3-thioxo-2-(2,6-dithioxo-3-piperidinyl)-1H-isoindol-1-one, 2-(3-Cyclohexenyl)-1H-isoindol-1,3(2H)-dithione, 2-(3-Cyclohexenyl)-1H-isoindole-1,3(2H)-dione, 2-(3-Cyclohexenyl)-1H-isoindol-1,3(2H)-dithione, 2,3-Dihydro-3-thioxo-2-(3-cyclohexenyl)-1H-isoindol-1-one, 3-(2,6-Dioxopiperidin-3-yl)benzoxazine-2,4-dione, 1-(2,6-Dioxo-3-piperidinylidene)-3-oxoisoindoline, 6-Thioxo-2-piperidinone, 2,6-Piperidinedithione, monothiophthalimide, dithiophthalimide, N-phenethylphthalimide, 3-Benzylimino-2-benzyl-2,3-dihydroisoindol-1-one, 3-Camphanic amino-2,6-piperdinedione and 3-[2',6'-piperidinedion-3'-yl]-7-amino-2H-1,3-benzoxazine-2,4(3H)-dione; and a pharmaceutically acceptable carrier. In more particular embodiments, the disclosed compositions are compounded for oral administration, and such oral dosage forms can include one or more of any of the disclosed compounds including those compounds particularly disclosed by their IUPAC names above. Such pharmaceutical compositions may be used in methods for modulating angiogenesis or TNF-α activity in a subject by administering to the subject a therapeutically effective amount of the composition.

As is demonstrated in the Examples that follow, thionation of thalidomide analogs to replace carbonyl groups with thiocarbonyl groups can provide thalidomide analogs with increased TNF-α activity, increased angiogenic activity or increased anti-angiogenic activity. Thus, although in certain structures the compounds are shown with carbonyl groups, it is to be understood that thionated derivatives of such compounds are also part of the disclosure.

4. EXAMPLES

Example 1

Improved Synthesis of Thalidomide

With reference to Scheme 1 below, t-Butoxycarbamate 2, on reaction with carbodiimide in THF, gave imide 3. Imide 3 was deprotected with trifluoroacetic acid in $CH_2Cl_2$ at room temperature to yield aminoglutarimide trifluoroacetate 4. Without further purification, compound 4 was reacted with phthalic anhydride in refluxing THF in the presence of triethylamine to afford thalidomide 1 in the total yield of 24% from 2. This procedure is much more practical and efficient than several prior reported synthetic routes for the preparation of thalidomide.

2,6-Dioxo-3-(t-butoxycarbonylamino)piperidine (3) was prepared and isolated as follows. A solution of N-(t-butoxycarbonyl)-L-glutamine (4.92 g) and carbonyl diimidazole (1.70 g) in THF (100 mL) was refluxed for 9 h. The solvent was removed and the crude product was recrystallized from hot EtOAc to give compound 3 (2.04 g, 45%) as white crystals: mp 214-215° C.; $^1$H NMR (DMSO-$d_6$) δ 4.22 (dd, J=6.2 Hz, J=11.0 Hz, 1H), 2.77-2.65 (m, 1H), 2.45 (m, 1 H), 1.96-1.87 (m, 2H), 1.40 (s, 9H); MS (Cl/$CH_4$) 227 [M−1]$^+$.

2,6-Dioxo-3-aminopiperidine trifluoroacetate (4) was prepared and isolated as follows. Compound 3 (59 mg) was suspended in $CH_2Cl_2$ (5 mL). $CF_3COOH$ (0.5 mL) was added. The reaction solution was stirred at room temperature for 4 h. The solvent was removed to give 4 (62 mg, 99%): $^1$H NMR (DMSO-$d_6$) δ 11.42 (s, 1H), 8.70 (br, 2H), 4.31 (dd, J=5.4 Hz, J=13 Hz), 2.88-2.72 (m, 2H), 2.25-2.09 (m, 2H).

Thalidomide (1) was prepared and isolated as follows. A mixture of 4, phthalic anhydride and $Et_3N$ in THF was refluxed for two days. The reaction mixture was concentrated and purification by column chromatography (eluent $CH_2Cl_2$/EtOAc=6:1) gave thalidomide (104 mg, 54%) as white crystals.

Example 2

Synthesis of Aromatic Thalidomide Analogs

With reference to Scheme 2 below, dimethylether 5 was obtained by condensation of aminopyridine with phthalic anhydride in refluxing AcOH in the presence of sodium acetate. On standing with HBr in glacial AcOH solution (30%) at room temperature for 18 h, selective ether cleavage of 5 was accomplished to give compound 6. The structure of compound 6 was determined by mass spectroscopy, 1D NMR and 2D NMR. The molecular ion for compound 6 is 270 amu, demonstrating that only one methyl ether was cleaved. 2D NOESY showed that protons on the methoxy group correlated with H-5, indicating that the 2-methoxy was selectively cleaved and that the 6-methoxy remained. When the reaction temperature elevated to 70° C., both methyl ethers were cleaved with HBr/HOAc solution (30%) to give diol 7.

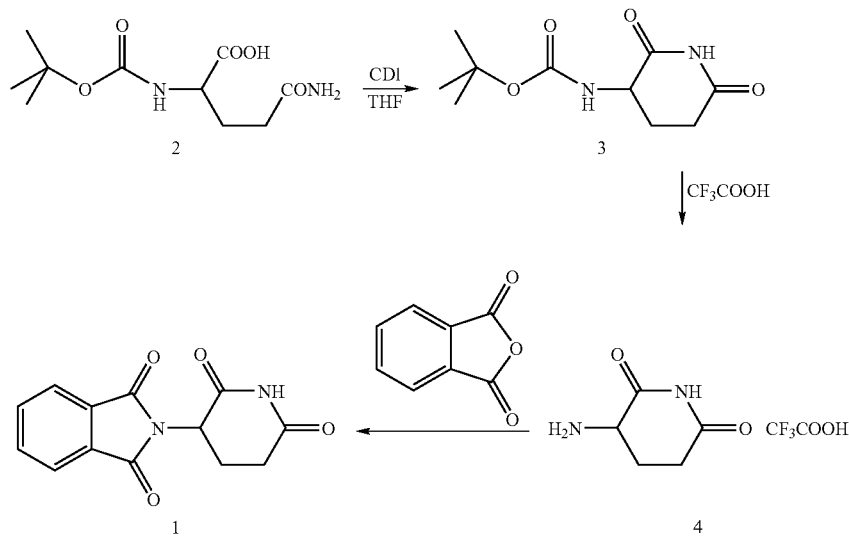

Scheme 1

Scheme 2

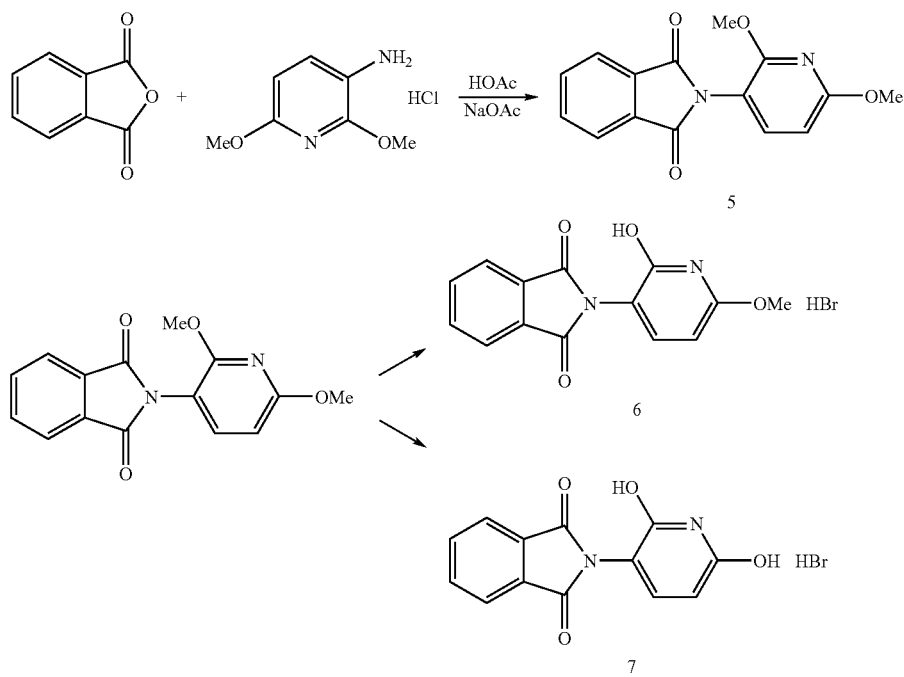

1,3-Dioxo-2-(2,6-dimethoxypyridin-3-yl)-isoindoline (5) was prepared and isolated as follows. A mixture of phthalic anhydride (0.89 g, 6 mmol), 3-amino-2,6-dimethoxypyridine monohydrochloride (95%, 1 g, 5 mmol) and sodium acetate (0.49 g, 6 mmol) in glacial acetic acid (50 ml) was refluxed for 3 h. The solvent was removed under vacuum. The residue was dissolved in dichloromethane (200 ml) and washed with water (100 ml×3), dried over $Na_2SO_4$ and concentrated to give the crude product. The crude product was recrystallized with ethyl acetate to give 5 (1.345 g, 90%) as a pale pink crystals: mp 182-183° C.; $^1$H NMR (CDCl$_3$) δ 7.96-7.90 (m, 2H), 7.80-7.76 (m, 2H), 7.44 (d, J=8.1 Hz, 1H), 6.42 (d, J=8.1 Hz, 1H, 3.95 (s, 3 H), 3.91 (s, 3 H); $^{13}$C NMR (DMSO-d$_6$) δ 166.5, 160.6, 156.1, 140.1, 132.8, 129.4, 121.4, 104.6, 99.3, 51.7, 51.5; MS (CI/CH$_4$) 285 [M+1]$^+$. Anal. Calcd for $C_{15}H_{12}N_2O_4$: C, 63.38; H, 4.25; N, 9.85. Found: C, 63.57; H, 4.18; N, 9.65.

1,3-Dioxo-2-(2-hydroxy-6-methoxypyridin-3-yl)-isoindoline hydrobromide (6) was prepared and isolated as follows. To a flask were added 2,6-dimethoxy-3-phthalimidopyridine (155 mg, 0.546 mmol) and hydrogen bromide solution in acetic acid (30%, 6 ml). The mixture was stirred at room temperature under $N_2$ for 18 h. Dry ether was added slowly until the solution became cloudy. White crystals were precipitated, filtered and washed with ether and ethyl acetate to afford 6 (127 mg, 67%) as white powdery crystals: mp 250° C.; $^1$H NMR (DMSO-d$_6$) δ 7.97-7.94 (m, 2H), 7.91-7.88 (m, 2H), 7.64 (d, J=8.2 Hz, 1H), 6.25 (d, J=8.2 Hz, 1H), 3.86 (s, 3H); $^{13}$C NMR (DMSO-d$_6$) δ 167.5, 162.1, 159.1, 142.8, 135.4, 132.1, 123.7, 108.2, 96.4, 54.8; MS (CI/CH$_4$) 270 [M]$^+$.

1,3-Dioxo-2-(2,6-dihydroxypyridin-3-yl)-isoindoline hydrobromide (7) was prepared and isolated as follows. To a flask were added 2,6-dimethoxy-3-phthalimidopyridine (150 mg, 0.528 mmol) and hydrogen bromide solution in acetic acid (30%, 6 ml). The mixture was stirred at an 70° C. oil bath under $N_2$ for 54 h. The mixture was cooled to room temperature, dry ether was added, and the supernatant liquid was decanted. Then ethyl acetate was added, solid precipitated, filtered and washed with ethyl acetate to afford 7 (126 mg, 71%) as a white solid: $^1$H NMR (CD$_3$OD) δ 7.83-7.77 (m, 4H), 6.37 (d, J=8.1 Hz, 1H), 6.37 (d, J=8.1 Hz, 1H); MS (CI/CH$_4$) 256 [M]$^+$; HRMS (DEI) m/z calcd for $C_{13}H_8N_2O_4$ 256.0484. found 256.0483.

Example 3

Synthesis of N-Substituted Thalidomide Analogs

With reference to Scheme 3 below, a mixture of N-phthaloyl-DL-glutamic anhydride and phenethylamine was heated in a 177° C. oil bath. The reaction mixture was purified by chromatography on a silica gel column to afford N-phenethylthalidomide (8) and N-phenethylphthalimide (9).

Scheme 3

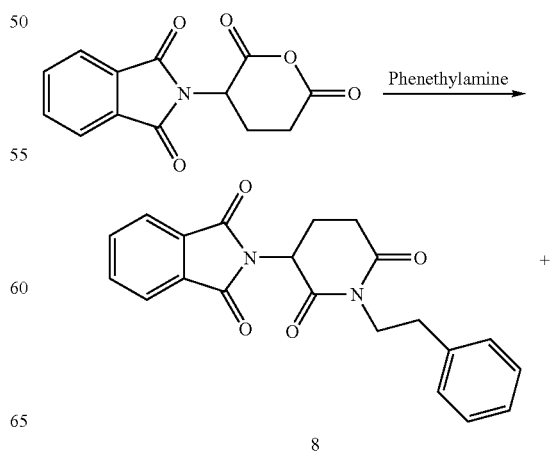

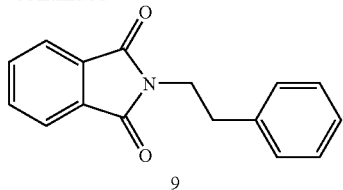

9

1,3-Dioxo-2-(1-phenethyl-2,6-dioxopiperidin-3-yl)isoindoline (8) was specifically prepared and isolated as follows. A mixture of N-phthaloyl-DL-glutamic anhydride (300 mg, 1.13 mmol) and phenethylamine (139 mg, 1.13 mmol) was stirred in a 177° C. oil bath for two hours. The reaction mixture was cooled down and purified by column chromatography, first using petroleum ether/dichloromethane (1:5) as an eluent to afford N-phenethyl phthalimide as a pale yellow solid [$^1$H NMR (CDCl$_3$) δ 7.78-7.77 (m, 2 H), 7.65-7.62 (m 2H), 7.22-7.16 (m, 5 H), 3.83 (t, 2 H), 2.92 (t, 2H)], and then using dichloromethane as an eluent to afford N-phenethyl thalidomide as a syrup that was then recrystallized from ether to provide white crystals [(139 mg, 34%): mp 122-123° C.; $^1$H NMR (CDCl$_3$) δ 7.84-7.81 (dd, J=3.1 Hz, J=5.4 Hz, 2H), 7.72-7.69 (dd, J=3.1 Hz, J=5.4 Hz, 2 H), 7.20-7.14 (m, 5 H), 4.89 (dd, J=5.4 Hz, J=12.5 Hz, 1 H), 4.01-3.92 (m, 2 H), 2.90-2.63 (m, 5 H), 2.06-2.02 (m, 1 H); Anal. Calcd for C$_{21}$H$_{18}$N$_2$O$_4$: C, 69.60; H, 5.01; N, 7.73. Found: C, 69.40; H, 5.13; N, 7.74].

Example 4

Synthesis of Azathalidomides

With reference to Scheme 4 below, azathalidomide was prepared from aminoglutarimide and commercial pyridine-3,4-dicarboxylic anhydride. Cbz-aminoglutarimide was deprotected by hydrogenolysis with catalyst palladium hydroxide on carbon (10%) to form aminoglutarimide. Pyridine-3,4-dicarboxyic anhydride was refluxed with aminoglutarimide in the presence of triethylamine to yield azathalidomide 11 in the total yield of 17% from Cbz-aminoglutarimide.

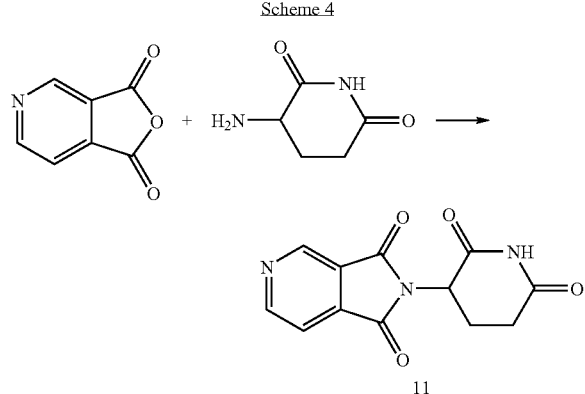

1,3-Dioxo-2-(2,6-dioxopiperidin-3-yl)-5-azaisoindoline (11) was prepared specifically as follows. A mixture of Cbz-aminoglutarimide (302 mg) and palladium hydroxide on carbon (20%) in 2-propanol (20 ml) was stirred under H$_2$ for one day. The reaction mixture was filtered through celite and washed with 2-propanol and methanol. The combined filtrate was concentrated to afford crude 3-amino-1,6-dioxopiperidine as syrup. To the flask containing 3-amino-1,6-dioxopiperidine was added 3,4-pyridinedicarboxylic anhydride (205 mg), triethylamine (0.16 ml) and THF (10 ml). The mixture was refluxed for one and a half days. The solvent was removed under vacuum. The residue was purified by column chromatography using CH$_2$Cl$_2$:MeOH (10:1) as eluent to afford azathalidomide (52 mg) in the yield of 17% from Cbz-aminoglutarimide as a pale purple solid: mp 233-235° C., $^1$H NMR (DMSO) δ 11.18 (s, 1H), 9.21 (s, 1H), 9.17 (d, J=4.8 Hz, 1 H), 7.98 (d, J=4.8 Hz, 1 H), 5.23 (dd, J=5.4 Hz, J=12.8 Hz, 1 H), 2.96-2.85 (m, 2 H), 2.60-2.51 (m, 1 H), 2.12-2.07 (m, 1 H); MS (CI/CH$_4$) m/z 259 [M]$^+$; Anal. Calcd for C$_{12}$H$_9$N$_2$O$_4$: C, 55.60; H, 3.50; N, 16.21. Found: C, 55.36; H, 3.44; N, 15.94.

Example 5

Synthesis of Acetoxythalidomide Analogs

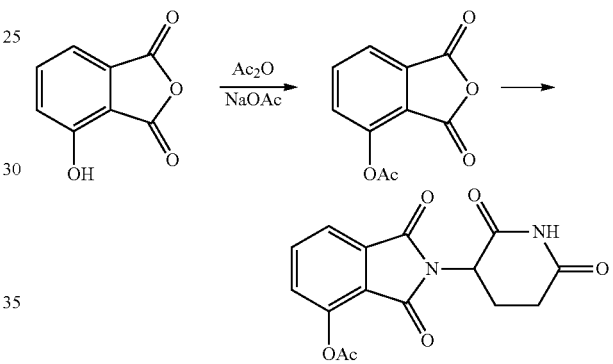

With reference to scheme 5 above, acetoxythalidomide was prepared and isolated as follows. First, 3-Acetoxyphathalic anhydride was prepared by refluxing a mixture of 3-hydroxyphthalic anhydride (150 mg), acetic anhydride (2 mL), and NaOAc (150 mg) for 8 h. The reaction mixture was filtered. The filtrate was concentrated and washed with dry ether to give a pale yellow solid (127 mg, 68%). $^1$H NMR (DMSO) δ 8.25 (d, J=7.9 Hz, 1H), 8.18 (dd, J=0.9 Hz, J=7.5 Hz, 1H), 7.97 (dd, J=0.9 Hz, J=7.9 Hz, 1H), 2.59 (s, 3H).

1,3-Dioxo-2-(2,6-dioxopiperidin-3-yl)-4-acetoxyisoindoline was prepared and isolated as follows. A mixture of 3-acetoxyphthalic anhydride (40 mg), aminoglutarimide trifluoroacetate (47 mg), and NaOAc (32 mg) in acetic acid (2 mL) was refluxed for 5 h. The solvent was evaporated, water (10 mL) was added, and the resulting solution was stirred for several minutes. The solid was filtered out and recrystallized from ethyl acetate to give 1,3-dioxo-2-(2,6-dioxopiperidin-3-yl)-4-acetoxyisoindoline as pale yellow crystals (35 mg, 66%): $^1$H NMR (DMSO) δ 11.16 (s, 1H), 11.07 (s, 1H), 7.64 (t, J=7.2 Hz, 1H), 7.22-7.31 (m, 2H), 5.05 (dd, J=5.4 Hz, J=12.5 Hz, 1H), 2.87-2.92 (m, 2H), 2.48 (s, 3H), 2.08-2.00 (m, 2H).

Example 6

Synthesis of Benzothaldomides

With reference to Scheme 6 below, 1,8-Naphthalic anhydride on heating with amine 4 in the presence of triethylamine in THF gave 12. Naphthalene-2,3-dicarboxylic acid was converted to the anhydride 13 which was reacted with aminoglutarimide trifluoroacetate 4 to afford benzothalidomide 14. Spectral data, including mass spectra and NMR, as well as combustion analyses were in accord with the structures assigned to these products.

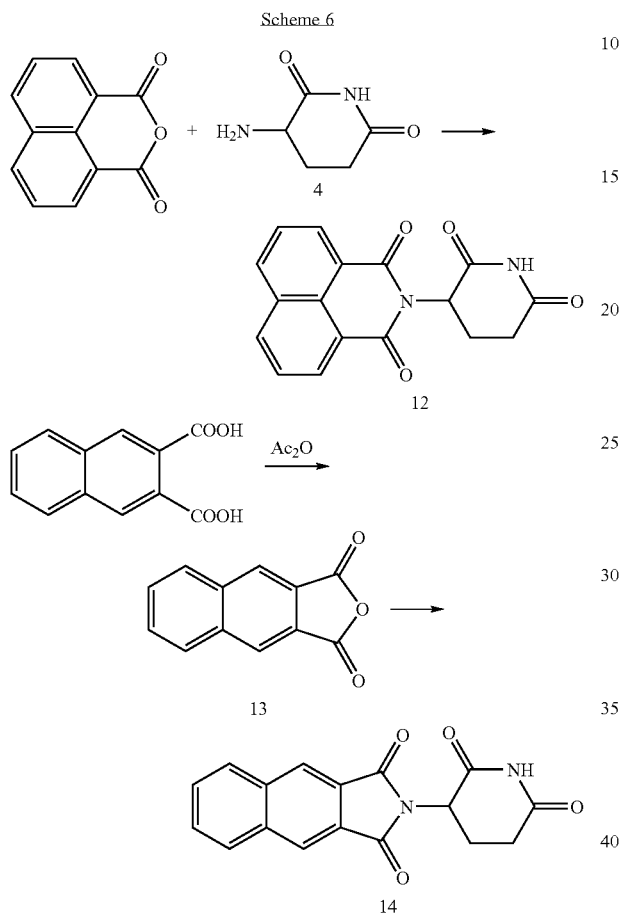

Specifically, N-(2,6-dioxopiperidin-3-yl)-1,8-naphthalimide (12) was prepared and isolated as follows. A mixture of amine 4 (0.877 mmol), 1,8-naphthalic anhydride (174 mg, 0.879) and triethylamine (1.22 ml) in THF (10 ml) was refluxed for 20 h. The solvent was removed and the residue was suspended in acetic anhydride and refluxed for 20 minutes. Ethanol (5 ml) was added at 80° C. and stirred for 30 min. On cooling the product was collected by filtration, and washed with EtOAc to give compound 12 (227 mg, 84%) as a pale green solid: mp>300° C.; $^1$H NMR (DMSO-$d_6$) δ 11.03 (s, 1H), 8.61-8.47 (m, 4H), 7.92 (dd, J=7.3 Hz, J=13.5 Hz, 2H), 5.85 (dd, J=5.4 Hz, J=11.3 Hz, 1H), 3.01-2.88 (m, 1H), 2.73-2.61 (m, 2H), 2.08-1.99 (m, 1H). MS (DEI) m/z 309 [M+1]$^+$; HRMS (DEI) m/z calcd for $C_{17}H_{13}N_2O_4$ 309.0875. found 309.0874; Anal. Calcd for $C_{17}H_{12}N_2O_4$: C, 66.23; H, 3.92; N, 9.09. Found: C, 65.97; H, 3.99; N, 8.91.

N-2,6-dioxopiperidin-3-yl)-2,3-naphthalenedicarboxamide (14) was prepared and isolated as follows. A mixture of 2,3-naphthalenedicarboxylic acid (199 mg, 0.875 mmol) and acetic anhydride (2 mL) was refluxed for 30 min. The reaction mixture was cooled down, and the solid was collected by filter to afford anhydride 13 (0.133 g, 77%) as a white solid. To a solution of aminoglutarimide trifluoroacetate (163 mg) and triethylamine (1 mL) in THF (10 mL) was added anhydride 13 (133 mg). The mixture was refluxed for 16 h. The solvent was removed under vacuum, and the residue was dissolved in EtOAc, washed with saturated aqueous NaHCO$_3$ solution and H$_2$O, dried and concentrated. The residue was purified by flash chromatography to give compound 14 as a white solid (146 mg, 70%). mp>300° C.; $^1$H NMR (DMSO-$d_6$) δ 11.3 (s, 1H), 8.60 (s, 2H), 8.30 (dd, J=3.3 Hz, J=6.1 Hz, 2H), 7.82 (dd, J=3.2 Hz, J=6.2 Hz, 2H), 5.24 (dd, J=5.6 Hz, J=13.0 Hz, 1H), 2.99-2.86 (m, 2H), 2.66-2.57 (m, 2H), 2.12-1.99 (m, 1H). MS (DEI) m/z 308 [M]$^+$; HRMS (DEI) m/z calcd for $C_{17}H_{12}N_2O_4$ 308.0797. found 308.0798; Anal. Calcd for $C_{17}H_{12}N_2O_4$·0.25H$_2$O: C, 65.28; H, 4.03; N, 8.96. Found: C, 65.42; H, 3.93; N, 8.94.

Example 7

Synthesis of Sulfur Analogs of Thalidomide

With reference to Scheme 7 below, reaction of thalidomide 1 with Lawesson's reagent, when stirred in benzene at 80° C. for 48 h, yielded thionamide 15 in a yield of 38%. In addition to monothiothalidomide, a trace of dithionimide 16 (1.6%) was also obtained. However, for the preparation of dithionimide, the yield proved to be very low (less than 2%) when the reaction of monothiothalidomide with Lawesson's reagent was performed between 80° C. to 120° C. The situation changed greatly when organic base was added to the reaction mixture. Thus, thionation of monothiothalidomide 15 with Lawesson's reagent in toluene was carried out at 110° C. in the presence of pyridine to give dithionimide 16 (45%) and dithionimide 17 (31%). The structures of these sulfur-substituted thalidomides were identified by mass spectra, 1DNMR and 2DNMR. Thalidomide was heated with Lawesson's reagent at 110° C. in the presence of morpholine to afford dithionimide 16 and trithionimide 18.

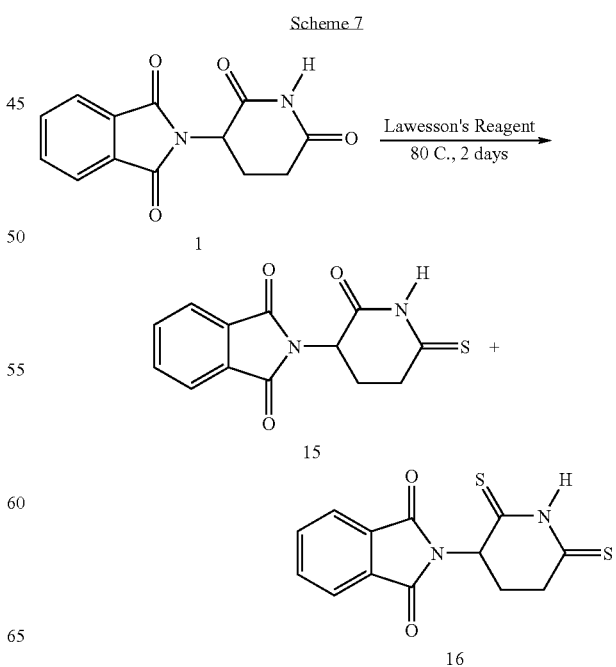

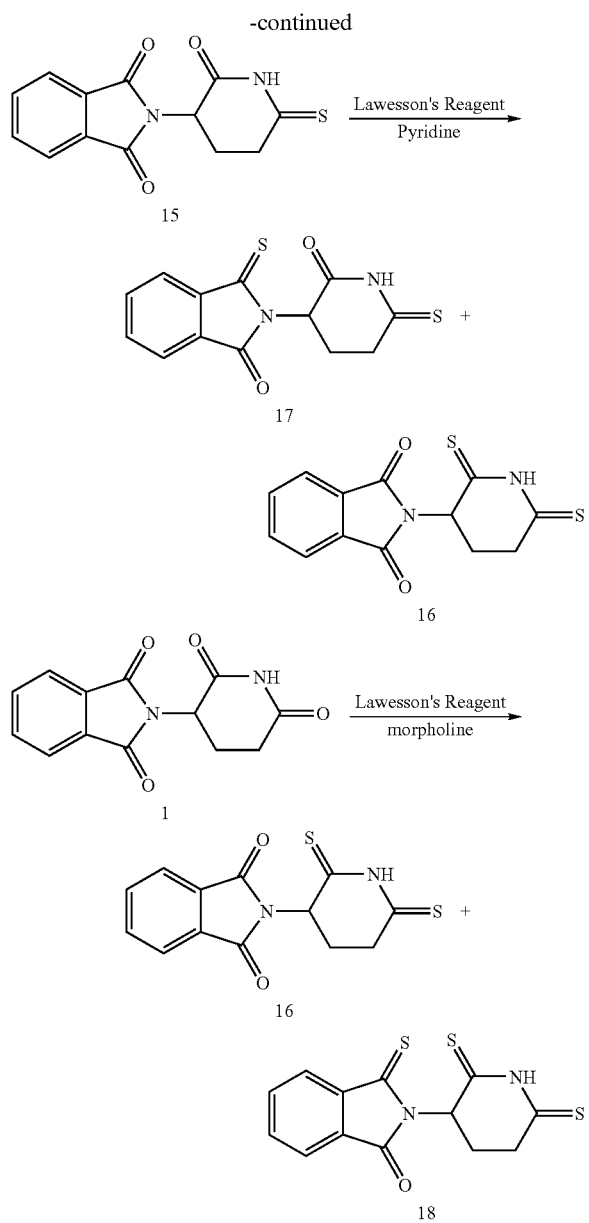

1,3-Dioxo-2-(2-oxo-6-thioxopiperidin-3-yl)isoindoline (15) was synthesized and isolated as follows. A mixture of thalidomide (170 mg, 0.658 mmol) and Lawesson's reagent (293 mg, 0.724 mmol) in benzene (50 ml) was stirred in a 80° C. oil bath for 2 days. The solvent was removed under vacuum. The residue was purified by column chromatography using $CH_2Cl_2$/petroluem ether (5:1) as eluent to afford compound 16 (3 mg, 1.6%) as a red solid and then, using $CH_2Cl_2$ as eluent, to afford compound 15 (68 mg, 38%) as a yellow solid: mp 225-226° C.; $^1$H NMR (DMSO-$d_6$) δ 12.83 (s, 1H), 8.00-7.92 (m, 4H), 5.32 (dd, J=5.6 Hz, J=12.9 Hz, 1H), 3.28-3.25 (m, 1H), 2.60-2.54 (m, 2H), 2.17-2.10 (m, 1H); $^{13}$C NMR (DMSO-$d_6$) δ 208.7(C-6'), 165.3(C-2'), 165.2 (C-1 & C-3), 133.1(C-5 & C-6), 129.3 (C-3a, C-7a), 121.7 (C-4 & C-7), 46.9 (C-3'), 38.9 (C-5'), 21.79 (C-4'); MS (CI/$CH_4$) m/z 274 [M]$^+$; Anal. Calcd for $C_{13}H_{10}N_2O_3S$: C, 56.92; H, 3.67; N, 10.21. Found: C, 56.89; H, 3.78; N, 10.15.

1-Thioxo-3-oxo-2-(2-oxo-6-thioxopiperidin-3-yl)isoindoline (16) and 1,3-dioxo-2-(2,6-dithioxopiperidin-3-yl) isoindoline (17) were synthesized as follows. A mixture of 15 (146 mg, 0.533 mmol), Lawesson's reagent (108 mg, 0.267 mmol) and pyridine (21 μl) in toluene was stirred at 110° C. under an atmosphere of $N_2$ for 12 h. Thereafter, more Lawesson's Reagent (108 mg, 0.267 mmol) and pyridine (21 μl) were added. The reaction mixture was stirred for a further 12 h. The solvent was removed under vacuum and the residue was purified by column chromatography (eluent $CH_2Cl_2$/petroleum ether=2:1, 10:1, then $CH_2Cl_2$/EtOAc=10:1) to afford 16 (30 mg, 45%) and 17 (21 mg, 31.5%). Starting material 15 (83 mg) was also recovered.

Compound 16: (yellow solid): mp 263-265° C.; $^1$H NMR (CDCl$_3$) δ 7.78-7.74 (m, 2 H), 7.66-7.63 (m, 2 H), 5.00 (dd, J=4.9 Hz, 11.9 Hz, 1 H), 3.43-3.35 (m, 1H), 2.95-2.84 (m, 2 H), 2.08-2.06 (m, 1 H); MS (DEI) m/z 290 [M]+; HRMS (DEI) m/z calcd for $C_{13}H_{10}N_2O_2S_2$ 290.0184. found 290.0185; Anal. Calcd for $C_{13}H_{10}N_2O_2S_2$: C, 53.77; H, 3.47; N, 9.65. Found: C, 53.38; H, 3.29; N, 9.50.

Compound 17: (red solid): mp 240-242° C.; $^1$H NMR (CDCl$_3$) δ 9.44 (s, 1 H), 8.05-8.02 (m, 1 H), 7.86-7.76 (m, 3 H), 5.75-5.64 (m, 1 H), 3.57-3.52 (m, 1 H), 3.09-2.99 (m, 2 H), 2.19-2.12 (m, 1 H). $^{13}$C NMR (DMSO): 208.16, 207.98, 166.10, 165.39, 134.32, 133.11, 132.42, 124.30, 122.15, 121.11, 49.64, 21.29; MS(DEI) m/z 291 [M+1]$^+$; HRMS (DEI) m/z calcd for $C_{13}H_{11}N_2O_2S_2$ 291.0262. found 291.0264; Anal. Calcd for $C_{13}H_{10}N_2O_2S_2$.0.5H$_2$O: C, 52.15; H, 3.70; N, 9.36. Found: C, 52.25; H, 3.44; N, 9.07.

1-Thioxo-3-oxo-2-(2,6-dithioxopiperidin-3-yl)isoindoline (18) was prepared and isolated as follows. A mixture of thalidomide (100 mg), Lawesson's reagent (157 mg) and morpholine (35 μl) in toluene (10 mL) was stirred at 105° C. under the atmosphere of $N_2$ for 24 h. The solvent was removed under vacuum and the residue was purified by column chromatography, using $CH_2Cl_2$:petroleum ether (1:1) as eluent, to afford compound 18 (13 mg, 11%) as red crystals: mp 244° C.; $^1$H NMR (CDCl$_3$) δ 10.81 (s, 1H), 8.05-8.01 (m, 1H), 7.91-7.75 (m, 3H), 5.92 (m, 1H), 3.57-3.52 (m, 1H), 3.13-2.97 (m, 2H), 2.18-2.15 (m, 1H); MS(DEI) m/z 306 [M]$^+$; HRMS (DEI) m/z calcd for $C_{13}H_{10}N_2OS_3$ 305.9955. found 305.9951; Anal. Calcd for $C_{13}H_{10}N_2OS_2$.0.5H$_2$O: C, 49.49; H, 3.51; N, 8.88. Found: C, 49.85; H, 3.24; N, 8.88. Then, $CH_2Cl_2$ was used as eluent to provide compound 16 (31 mg, 28%) as yellow crystals.

Example 8

Synthesis of Benzoxazine-2,4-diones

With reference to Scheme 8 below, salicylic acid was treated with ethyl chloroformate, and then this reaction mixture was evaporated at reduced pressure to remove any unreacted ethyl chloroformate. Stirring the resulting residue with amine in the presence of triethylamine afforded substituted benzoxazine-2,4-diones Scheme 8

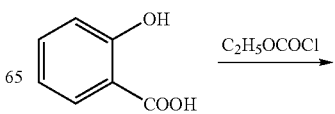

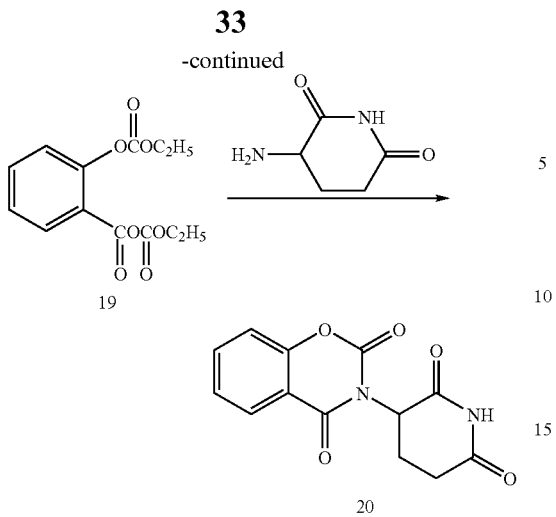

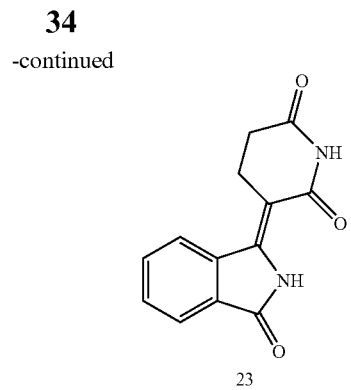

3-(2,6-Dioxopiperidin-3-yl)benzoxazine-2,4-dione (20) was prepared and isolated as follows. To a cold ice/salt solution of salicylic acid (100 mg) and triethylamine (303 ml) in chloroform (10 mL) was added ethyl chloroformate (157 ml). The reaction mixture was allowed to warm to room temperature, and, thereafter, stirring was continued for 3 h. The solvent was removed under vacuum to give crude 19. Without further purification, crude compound 19 was dissolved in CHCl$_3$ and cooled with ice. To the ice cold solution was added amine (95 mg). The reaction mixture was allowed to warm to ambient temperature and stirred at room temperature overnight. The white solid precipitated, collected by filtration and washed with chloroform to give compound 20 (79 mg, 74%) as a white crystals: mp 264° C.; $^1$H NMR (DMSO-d$_6$) δ 11.18 (s, 1H), 8.07-7.85 (m, 2H), 7.50 (d, J=8.5 Hz), 5.78-5.75 (m, 0.6H), 5.49-5.47 (m, 0.4H), 2.90-2.87 (m, 1H), 2.05 (m, 1H); $^{13}$C NMR (DMSO-d$_6$) δ 173.0 (0.6C), 172.9 (0.4C), 169.9 (0.6C), 169.6 (0.4C), 160.8 (0.6C), 159.8 (0.4C), 152.5 (1C), 148.4 (0.4C), 146.5 (0.6C), 137.2 (1C), 128.1 (0.6C), 127.6 (0.4C), 126.1 (1C), 116.8 (1C), 114.5 (0.4C), 113.9 (0.6C), 54.1 (0.4C), 51.4 (0.6C), 31.0 (1C), 21.2 (1C). MS(DEI) m/z 274 [M]$^+$; HRMS (DEI) m/z calcd for C$_{13}$H$_{10}$N$_2$O$_5$ 274.0590. found 274.0582; Anal. Calcd for C$_{13}$H$_{10}$N$_2$O$_5$: C, 56.94; H, 3.68; N, 10.22. Found: C, 56.51; H, 3.77; N, 9.95.

Example 9

Synthesis of 1-(2,6-Dioxo-3-piperidinylidene)-3-oxoisoindoline

With reference to Scheme 9 below, monothiophthalimide (21) was stirred with 3-bromoglutarimide (22) in the presence of Na$_2$CO$_3$ in an Eschenmoser coupling reaction. Thus, compound 23 was formed by alkylation of monothiophthalimide with 3-bromoglutarimide, followed by elimination of sulfur.

Scheme 9

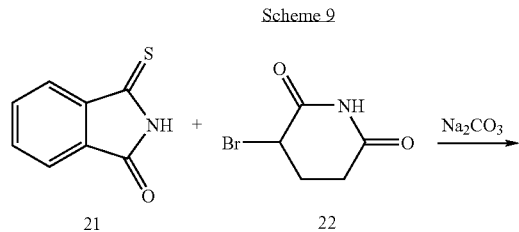

1-(2,6-Dioxo-3-piperidinylidene)-3-oxoisoindoline (23) was specifically prepared and isolated as follows. A mixture of 21 (16 mg, 0.1 mmol), 22 (19 mg, 0.1 mmol), and potassium carbonate (100 mg) in anhydrous THF was refluxed for 7 h. Thin-layer chromatography (TLC) showed that the starting materials had disappeared. Ethyl acetate (20 ml) and water (10 ml) were added. The organic layer was separated, dried over Na$_2$SO$_4$ and concentrated under vacuum. The residue was purified by chromatography using petroleum ether/ethyl acetate (first 2:1 then 1:2) to give 23 (14 mg, 58%) as yellow crystals: mp 295° C.; $^1$HNMR (DMSO-d$_6$): 11.05 (s, 1 H), 10.29 (s, 1 H), 8.13 (d, J=7.6 Hz, 1 H), 7.89 (d, J=7.2 Hz, 1H), 7.80 (m, 1 H), 7.73 (m, 1H), 3.20 (t, J=7.0 Hz, 2 H), 2.67 (t, J=7.0 Hz, 2 H). $^{13}$C NMR (DMSO-d$_6$): 172.6, 169.0, 167.3, 142.7, 136.1, 134.3, 131.7, 130.1, 126.4, 124.1, 104.6, 21.2, 11.7. MS(DEI) m/z 242 [M]$^+$; HRMS (DEI) m/z calcd for C$_{13}$H$_{10}$N$_2$O$_3$ 242.0691. found 242.0687.

Example 10

Salicylamide Analogs

Reaction of commercial acetylsalicyloyl with aminoglutarimide trifluoroacetate was carried out to give acetylsalicylamide 24 according to Scheme 10 below.

Scheme 10

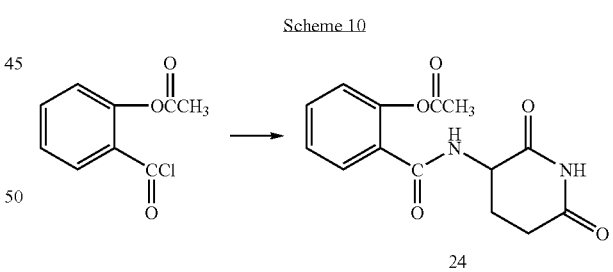

More specifically, 2-acetoxy-N-(2,6-dioxopiperidin-3-yl)benzamide (24) was prepared as follows. To an ice cold solution of acetylsalicyloylchloride (252 mg) and triethylamine (0.58 mL) in chloroform (30 mL) was added 3-aminoglutaride trifluoroacetate (207 mg). The reaction temperature was allowed to warm to room temperature and stirring was continued overnight. The solvent was removed and recrystallization from ethyl acetate gave compound 24 as white crystals (0.36 g, 98%): $^1$H NMR (DMSO-d$_6$) δ 11.00 (s, 1H), 8.73 (d, J=8.3 Hz, 1H), 7.81 (dd, J=1.6 Hz, J=7.7 Hz, 1H), 7.72 (m, 1H), 7.54 (m, 1H), 7.38 (dd, J=0.9 Hz, J=8.1 Hz, 1H), 4.95-4.82 (m, 1H), 2.96-2.90 (m, 1H), 2.43 (s, 3H), 2.18-2.15 (m, 2H).

Example 11

Synthesis of Thiothalidomides and Determination of Their TNF-α Inhibitory Activity A series of thiothalidomides and analogs were designed to explore their action on inhibition of TNF-α. Monothiothalidomide 205 (same as compound 15 in Example 7) was prepared as shown in Scheme 11. tert-Butoxycarbonyl-L-glutamine 202 was refluxed with carbonyl diimidazole (CDI) in THF, and cyclized to afford imide 203 (Muller et al., "Amino-substituted thalidomide analogs: potent inhibitors of TNF-α production," *Bioorg Med. Chem, Lett.* 9, 1625-1630, 1999).

Imide 203 then was treated with trifluoroacetic acid in $CH_2Cl_2$ to remove the protective group to generate aminoglutarimide trifluoroacetate 204. Without further purification, compound 204 was reacted with phthalic anhydride in refluxing THF in the presence of triethylamine to produce thalidomide 201 (same as compound 1 in Example 7) in the total yield of 31% from compound 202. Thalidomide 201 was thionated with Lawesson's reagent (LR, Cava et al., "Thionation reaction of Lawesson's Reagents," *Tetrahedron*, 41, 5061-5087, 1985, the entirety of which is incorporated herein by reference) to generate a single new product that had a structure identified as 6'-thiothalidomide 205 by mass spectrometry and 1D & 2D nuclear magnetic resonance spectroscopy. The position of the thiocarbonyl group was established from the heteronuclear multiple bond correlation (HMBC) cross peak of H-5'/C-6'.

Scheme 11

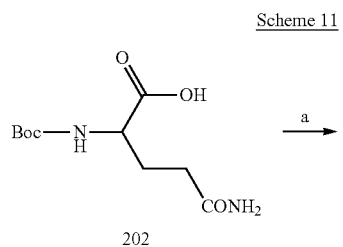

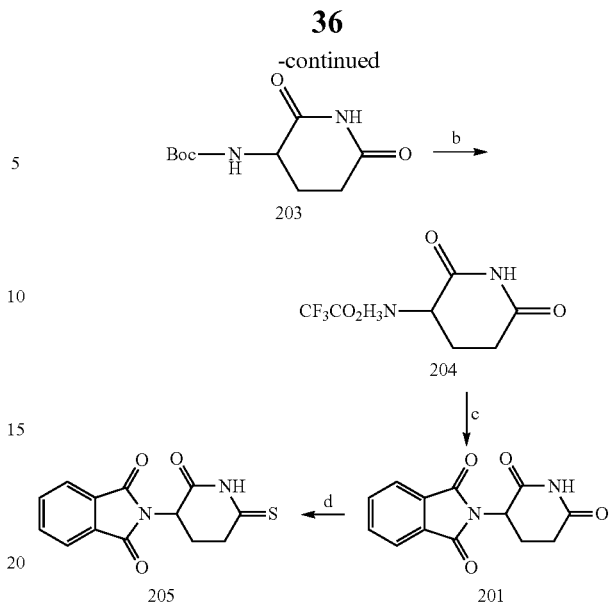

Reagents: (a) CDI/THF; (b) $CF_3COOH/CH_2Cl_2$; (c) phthalic anhydride, $Et_3N$/THF; (d) Lawesson's reagent/toluene.

The synthesis of 3-thiothalidomide 212 is shown in Scheme 12 below. N-Phthaloyl-L-glutamic acid 206 was esterified to afford diester 207. Compound 207 was thionated with LR at 110° C. to give compound 208 as a major product. Concurrently, compound 209 was separated as a minor product by chromatography.

3-thiothalidomide, 212, could not be prepared through the cyclization of compound 208 with ammonia or amine as ammonia reacts with the thioamide; reaction of compound 208 with benzylamine produced the unexpected compound 210. In an alternative approach, compound 208 was hydrolyzed under acidic conditions to give diacid 211. Compound 211 was then reacted with trifluoroacetamide to generate 3-thiothalidomide 212 in the presence of 1-hydroxybenzotriazole (HOBt) and 1-[3-(dimethylamino)propyl]-3-ethylcarbodiimide hydrochloride (EDCI, Flaih et al., "An expeditious synthesis of cyclic imides," *Tetrahedron Lett.* 40, 3697-3698, 1999).

Scheme 12

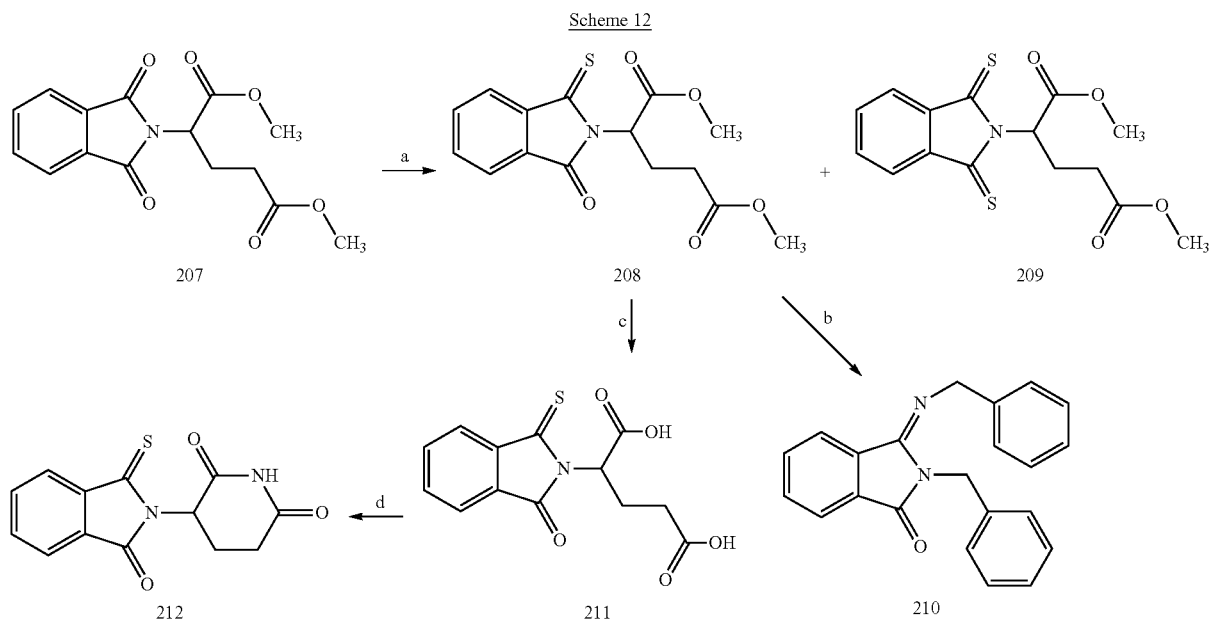

Reagents: (a) Lawesson's reagent/toluene; (b) Benzylamine; (c) HCl/HOAc; (d) $F_3CCONH_2$, HOBt, EDCI, $Et_3N/CH_2Cl_2$.

In the synthesis of dithiothalidomide, one method involved the reaction of monothiothalidomide with LR at reflux in toluene. Under such conditions, 2',6'-dithiothalidomide was obtained in a yield of less than 2% (Scheme 13a). The yield was so low that improvement was desirable, and was undertaken by modifying the reaction conditions. It is believed that the mechanism underlying the reaction between LR and a carbonyl moiety is that a highly reactive dithiophosphine ylide 214, rather than LR itself, likely is the active thionating agent (Scheme 4, Cava et al., "Thionation reaction of Lawesson's Reagents," *Tetrahedron*, 41, 5061-5087, 1985, the entirety of which is incorporated herein by reference). The Lewis base may be able to increase the reactivity or LR as the base may drive the unfavorable equilibrium and elevate the concentration of the ylide 214. When pyridine was used as a catalyst for thionation, monothiothalidomide 205 was thionated with LR to produce two dithiothalidomides, 213 (same as compound 16 in Example 7) and 215 (same as compound 17 in Example 7), in yields of 45% and 31%, respectively (Scheme 13 b,c). Dithiothalidomide 213 was further thionated with LR in the presence of the stronger base, morpholine, to give trithiothalidomide 216 (same as compound 18 in Example 7) in a yield of 65%.

Glutarimide 217 was thionated with LR in THF at room temperature to afford compound 218 as a major product. Glutarimide 217 also was refluxed with LR in toluene to produce dithioglutarimide 219 (Scheme 15). Reaction of potassium phthalimide with 3-bromocyclohexene in a Gabriel reaction gave compound 221. Thereafter, thionation of compound 221 with LR afforded compounds 222 and 223 (Scheme 16). Compounds 224 and 225 were prepared in a similar procedure to that used in the preparation of compounds 222 and 223.

Scheme 15.

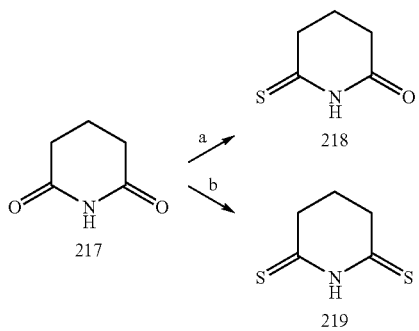

Reagents: (a) Lawesson's reagent/THF, room temperature; (b) Lawesson's reagent, reflux/toluene Scheme 13

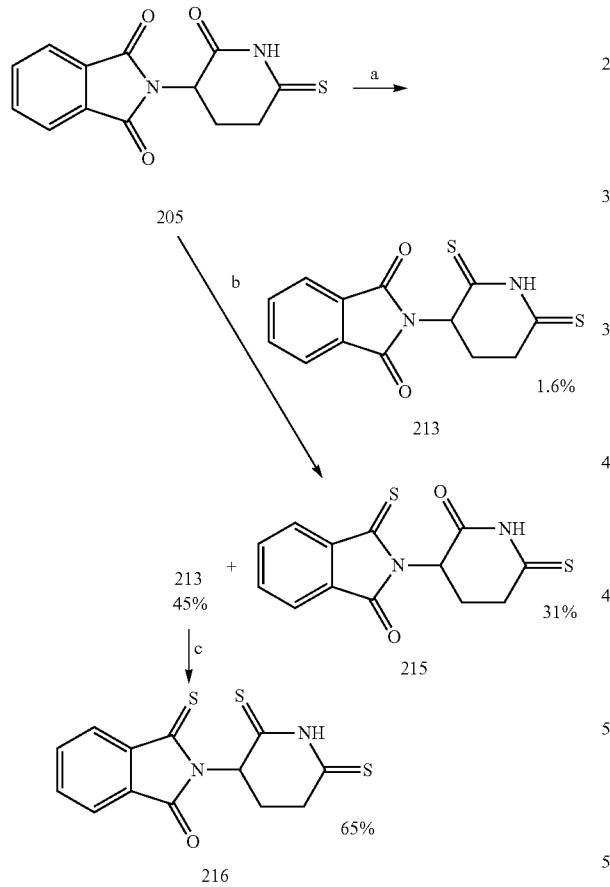

Reagents: (a) Lawesson's reagent/toluene; (b) Lawesson's reagent, pyridine/toluene; (c) Lawesson's reagent, morpholine/toluene.

Scheme 16.

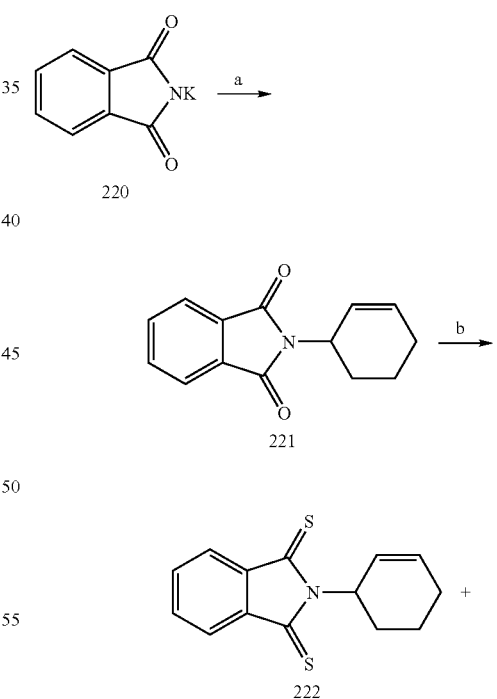

Scheme 14. The mechanism of catalysis for Lawesson's reagent.

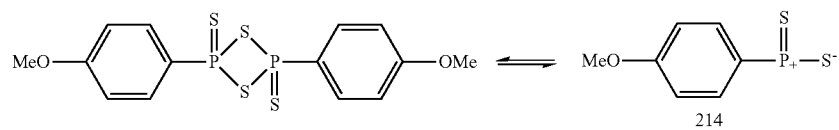

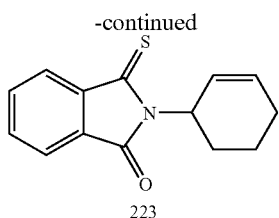

223

Reagents: (a) 3-bromocyclohexene/DMF; (b) Lawesson's reagent/toluene.

The structures of the thiothalidomide compounds of this Example are summarized below.

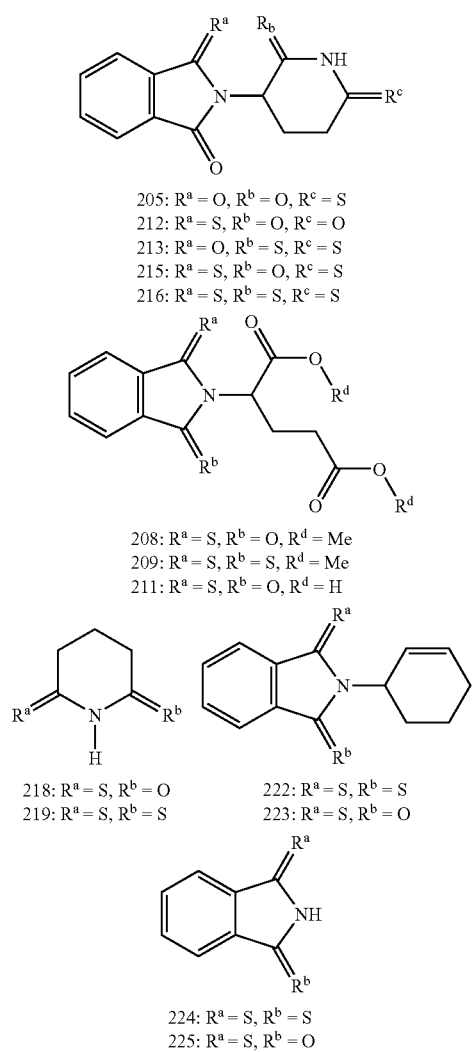

205: $R^a = O, R^b = O, R^c = S$
212: $R^a = S, R^b = O, R^c = O$
213: $R^a = O, R^b = S, R^c = S$
215: $R^a = S, R^b = O, R^c = S$
216: $R^a = S, R^b = S, R^c = S$

208: $R^a = S, R^b = O, R^d = Me$
209: $R^a = S, R^b = S, R^d = Me$
211: $R^a = S, R^b = O, R^d = H$

218: $R^a = S, R^b = O$
219: $R^a = S, R^b = S$

222: $R^a = S, R^b = S$
223: $R^a = S, R^b = O$

224: $R^a = S, R^b = S$
225: $R^a = S, R^b = O$

The action of the these thiothalidomide analogs in inhibiting TNF-α secretion was assessed in human peripheral blood mononuclear cells (PBMC) and the results are shown in Table 1. Freshly prepared PBMCs were utilized in all studies. Blood, 40 ml, was drawn from a volunteer, immediately mixed with 50 U/ml Na heparin and was diluted to 50 ml total volume with sterile PBS. Samples, 20 ml, of this preparation then were layered on 20 ml Ficoll-Paque and were centrifuged (800 g, 20 min). The Ficoll/serum interface, containing PBMCs, was collected, diluted to 200 ml with PBS, and then was centrifuged (800 g, 15 min) to pellet the cells. Thereafter, the recovered pellet was re-suspended in 37° C. tissue culture medium (RPMI/1 mM Sodium pyruvate/10% heat inactivated FBS/2 mM Glutamax) and placed on ice. Recovered cells were counted, pipetted (200 ul of 5×10⁵/ml) into 96 well plates, and incubated for an hour (37° C., 5% $CO_2$). Thereafter, appropriate concentrations of test compounds or vehicle (10 ul DMSO) were added to duplicate wells. Following a further hour of incubation, a 10 ul sample of lipopolysaccharide (LPS)(100 ng/ml in supplemented medium) or vehicle was added to induce stimulated and unstimulated cells, respectively, and the cells were incubated overnight. Sixteen hours later, supernatants were collected for quantification of TNF-α levels by ELISA assay (Pierce-Endogen human TNF-α mini kit, Rockford, Ill.) and the use of specific capture and detection monoclonal antibodies, M303E and M302 (Pierce-Endogen), respectively. ELISA plates were read at λ=450 nm and TNF-α levels were determined from a six-point calibration curve that was run concurrently with the test samples. The effect of test drug concentrations on the cellular viability of PBMCs was assessed by MTS assay (Promega, Madison, Wis.) of the cells that provided the supernatant samples assayed for TNF-α levels, described above. It should be understood that this method can be used to test any of the disclosed compounds as a screening assay for readily determining their TNF-α modulating activity, and for selecting them for use in the disclosed method of treating a subject.

TABLE 1

Inhibition of LPS-induced TNF-α production in PBMC and cell viability

| Compound | % Inhibition at 30 μM | $IC_{50}$ (μM) | Cell viability | | |
|---|---|---|---|---|---|
| | | | at 30 μM | at 3 μM | at 0.3 μM |
| 205 | 31 | >30 | >100 | 90 | 96 |
| 208 | 56 | 20 | 93 | 99 | 96 |
| 209 | 85 | 10 | 57 | 86 | 89 |
| 211 | 20 | >30 | 86 | 93 | 93 |
| 212 | 23 | >30 | 94 | 100 | 94 |
| 213 | 52 | 20 | 69 | 87 | 94 |
| 215 | 61 | 11 | >100 | 87 | 94 |
| 216 | 79 | 6 | 94 | 86 | 90 |
| 218 | 15 | >30 | >100 | 84 | 86 |
| 219 | 75 | 8 | >100 | 98 | 99 |
| 222 | 86 | 15 | 50 | 94 | 96 |
| 223 | 85 | 16 | 57 | 89 | 99 |
| 224 | 95 | 3 | 54 | 83 | 83 |
| 225 | 34 | >30 | >100 | 94 | 94 |

Thalidomide, 201, entirely lacked activity at 30 μM. A concentration of 100 μM was required for significant activity ($IC_{50}$ ~200 μM). The monothiothalidomides, 6'-thiothalidomide 205 and 3-thiothalidomide 212 showed only marginal activity at 30 μM with 31% and 23% inhibition of TNF-α secretion, respectively. In contrast, the dithiothalidomides, including 2',6'-dithiothalidomide 213 and 3,6'-dithiothalidomide 215, exhibited more potent inhibitory activities with $IC_{50}$ values of 20 μM and 11 μM, respectively. However, assessment of cell viability by MTS assay showed that 213 induced increasing cytotoxicity at higher concentrations. Trithiothalidomide 216 inhibited TNF-α production with an $IC_{50}$ of 6 μM, without accompanying toxicity. Compared with thalidomide, 201, with an $IC_{50}$ of ~200 μM for the inhibition of TNF-α synthesis, trithiothalidomide 216 is over 30-fold more active. Hence, successive replacement of a carbonyl with a thiocarbonyl group led to improved inhibitory activity compared to 201, unassociated with toxicity. In this regard, the synthesized thiothalidomides possessed TNF-α lowering potency in the following decreasing order: trithiothalidomide 216>dithiothalidomide 215 and 213>monothiothalidomides 205 and 212>thalidomide, 201.

A comparison of the physical properties of thalidomide, 201, and thiothalidomides shows that they have similar Van der Waals radii and bond angles, although the C=S bond is slightly longer than the C=O bond. Although not wishing to be bound by any particular theory, a possible explanation accounting for the elevated potency of the thiothalidomides is that their enhanced lipophilicity and loss of hydrogen bond acceptor capability potentially allows the attainment of higher intracellular drug levels. Interestingly, compounds 208, 209 and 211 are thio analogs of hydrolysis metabolites of thalidomide. Assessment of their TNF-α inhibitory action determined that the monothio analog, 208, has an $IC_{50}$ of 20 µM without toxicity; demethylation (211) lowered potency. The dithio analog, 209, proved 2-fold more potent still than 208, but induced cellular toxicity at lower concentrations. Intriguingly, thio analogs 222 and 223, with a simplified glutarimide ring, were found to be active TNF-α inhibitors, albeit with some toxicity at 30 µM, with $IC_{50}$ values (15 µM and 16 µM respectively) that were greater than 212 (>30 µM possessing a normal glutarimide ring.

In this regard, thalidomide is composed of two distinct moieties: the glutarimide and phthalimide rings. Thioglutarimides and thiophthalimides were thus synthesized and evaluated to assess the effect of thio-analogs of these two moieties on TNF-α levels. Monothioglutarimide 218 minimally inhibited TNF-α secretion at a concentration of 30 µM, however dithioglutarimide 219 exerted a potent inhibitory effect with an $IC_{50}$ of 8 µM and a lack of toxicity. Surprisingly, such a simple structure, dithioglutarimide 219, proved to be 25-fold more active than thalidomide 201. In contrast, 2',6'-dithiothalidomide 213, a phthalimido substituted dithioglutarimide, is less active than dithioglutarimide 219, and induces toxicity at high concentration. Monothiophthalimide 225 showed marginal TNF-α activity at a concentration of 30 µM without toxicity. Interestingly, however, dithiophthalimide 224 was found to possess potent activity with an $IC_{50}$ of 3 µM. Although it was associated with toxicity at 30 µM, its inhibition of TNF-α occurred at an order of magnitude lower concentration that was well tolerated.

As described, compounds 215, 216 and 219 potently inhibited TNF-α secretion without toxicity. As a consequence, additional studies were undertaken to elucidate the mechanism underpinning this action. Gene and protein expressions are controlled at the level of transcription, post-transcription, RNA stability, and translation under different physiological stimuli. Recently, post-transcriptional pathways have been recognized to provide a major means of regulating eukaryotic gene expression. In this regard, TNF-α and other cytokines and protooncogenes are known to be regulated at the post-transcriptional level. Multiple proteins, including the four cloned proteins AUF1, HuR, TTP and HuD have been shown to bind to a region of the mRNA that contains adenylate/uridylate (AU)-rich elements (AREs) in the 3'-untranslated region (UTR). These proteins mediate RNA turnover and decay, and hence translational efficiency. The stability of TNF-α mRNA is largely regulated at its 3'-UTR, which contains a well characterized ARE. Although AREs are found in a number of different cytokine and protooncogene RNAs, the pathways by which they induce degradation are highly specific for a given ARE indicating some cellular specificity. When the AREs from different cytokines are complexed with AUF1, different binding affinities are observed. Notably, however, the highest affinity for AUF1 is to human and then mouse TNF-α.

To determine the involvement of the 3'-UTR in the action of the thalidomide analogs, their ability to inhibit reporter gene activity in cells containing the TNF-α 3'-UTR versus a control vector was assessed. The results are shown in FIG. 1. This cell-based assay utilized two stably transfected cell lines derived from the mouse macrophage line, RAW264.7. One line, designated "luciferase only" expressed a luciferase reporter construct without any UTR sequences. The other line, designated "luciferase+TNF-α UTR" expressed a luciferase reporter construct with the entire 3'-UTR of human TNF-α inserted directly downstream of the luciferase coding region. Compounds were added in a concentration-dependent manner, and at the end of the incubation period (16 h, 37° C., 5% $CO_2$) the media was removed, cells were lysed and luciferase activity was assayed with Steady-glo luciferase assay reagent (Promega) according to the supplier's directions. Background was subtracted and data from this assay was expressed as a ratio of the +3'-UTR to −3'-UTR (control) values, and was expressed as a percent as shown in FIG. 1. In this manner, compounds that show a differential effect on the two cell lines, with and without a 3'-UTR, are highlighted. The action of compounds 215, 216 and 219 in cells (mouse macrophage cell line, RAW264.7) possessing a luciferase reporter element plus the 3'-UTR of human TNF -α compared to cells lacking the 3'-UTR are shown in FIG. 1. Compounds 215, 216 and 219 exerted differential effect on the two cell lines in a dose-dependent manner, consistent with their ability to inhibit TNF-α production via the 3'-UTR. All agents lowered luciferase reporter activity in cells stably expressing the 3'-UTR. Thalidomide lacked activity at 50 µM.

As TNF-α protein levels changed without significant alterations in mRNA levels (data not shown), protein expression is presumably regulated via translational control (at the post-transcriptional level). There is precedence for translational (protein) control through either the 3'- or 5'-UTR regions of a number of critical proteins that are current drug targets. For example, levels of the beta-amyloid precursor protein (APP) that is central to the development of AD can be regulated by either UTR. Turnover and translation of APP mRNA is regulated by a 29-nucleotide instability element within the 3'-UTR located 200 nucleotides downstream from the stop codon. This 3'-UTR element acts as an mRNA destabilizer whose function can be inhibited by the presence of growth factors. In contrast, different cytokines, including TNF-α, and iron can up regulate APP protein synthesis at the level of its 5'-UTR, where, interestingly, the anticholinesterase, phenserine, that is currently in clinical trials for AD, lowers APP protein levels with concurrent maintenance of mRNA steady-state levels through translational modification within the same 5'-UTR element. A further example is that of the human immunodeficiency virus 1 (HIV-1) Trans-activating transduction (tat) protein, which binds trans-activation-responsive region (TAR) RNA. Tat is brought into contact with the transcription machinery after binding the TAR element, which is a 59-residue stem-loop RNA found at the 5' end of all HIV-1 transcripts. Finally, thalidomide (201) has been reported to lower cyclooxygenase-2 (Cox-2) biosynthesis via its 3'-UTR that appears to likewise contain an ARE that can regulate Cox-2 mRNA stability. The studies of analogs 215, 216 and 219 confirm regulation of TNF-α protein levels by thalidomide (201) via its 3'-UTR, but whether or not the 5'-UTR contains a similar element that is accessible to pharmacological manipulation remains to be determined, as does action against Cox-2.

In summary, disclosed thiothalidomide analogs include analogs that are more potent inhibitors of TNF-α production in LPS-induced human PBMCs than thalidomide 201. The isosteric replacement of successive carbonyl groups by a thiocarbonyl leads to an increasing inhibition with the number of moieties replaced (trithiothalidomide 216>dithiothalidomide 215 and 213>monothiothalidomides 205 and 212>thalidomide 201).

TNF-α has been validated as a drug target for two drugs on the market; Remicade (Cetocor, Malvern, Pa.; Schering-Plough, Orange, N.J.) and Enbrel (Amgen, Thousand Oaks, Calif.; Wyeth-Ayerst, Princeton, N.J.). However, both of these drugs are large macromolecules and hence require injection. In contrast, the small molecule drugs disclosed herein offer a means to potently and safely inhibit TNF-α without injection, for example, by oral administration.

Synthesis and Characterization Details

General. Melting points were determined with a Fisher-Johns apparatus and are uncorrected. $^1$H NMR, $^{13}$C NMR and 2D NMR were recorded on a Bruker AC-300 spectrometer. Mass spectra and high resolution mass spectra (HRMS) were recorded on a VG 7070 mass spectrometer and a Agilent Technologies 5973N GC-MS (CI). All exact mass measurements show an error of less than 5 ppm. Elemental analyses were performed by Atlantic Microlab, Inc., Norcross, Ga.

3-(tert-Butoxycarbonylamino)-2,6-piperidinedione (203). A mixture of N -(tert-butoxycarbonyl)-L-glutamine (4.92 g, 20 mmol) and carbonyl diimidazole (3.24 g, 20 mmol) in THF (100 mL) was refluxed for 16 h. Thereafter, solvent was removed and the crude product was recrystallized from hot EtOAc to give compound 203 (2.04 g, 45%) as white crystals: mp 214-215° C.; $^1$H NMR (DMSO-d$_6$) δ 4.22 (dd, J=6.2 Hz, J=11.0 Hz, 1H), 2.77-2.65 (m, 1H), 2.45 (m, 1H), 1.96-1.87 (m, 2H), 1.40 (s, 9H); MS (CI/CH$_4$) m/z 227 [M−1]$^+$.

2-(2-Oxo-6-thioxo-3-piperidinyl)-1H-isoindole-1,3(2H)-dione (205). Compound 203 (1.14 g, 5 mmol) was suspended in CH$_2$Cl$_2$ (100 mL). To the mixture was added CF$_3$COOH (10 mL) and this then was stirred at room temperature for 4 h. The solvent was evaporated to give crude 204 (1.25 g): $^1$H NMR (DMSO-d$_6$) δ 11.42 (s, 1H), 8.70 (br, 2H), 4.31 (dd, J=5.4 Hz, J=13 Hz), 2.88-2.72 (m, 2H), 2.25-2.09 (m, 2H). A mixture of crude 204 (1.25 g) and phthalic anhydride (0.89 g, 6 mmol) and Et$_3$N (1.39 ml, 10 mmol) in THF (150 mL) was refluxed for two days. The reaction mixture was concentrated and the residue was crystallized from ethyl acetate to give thalidomide (201) (0.89 g, 69%) as white crystals; mp 276° C. (lit. 276-279° C.). A mixture of thalidomide 201 (258 mg, 1 mmol) and Lawesson's reagent (222 mg, 0.55 mmol) in toluene (50 ml) was stirred at reflux for 12 h; thereafter, solvent was removed under vacuum. The resulting residue was purified by column chromatography using CH$_2$Cl$_2$ as the eluent to afford compound 205 (200 mg, 73%) as a yellow solid: mp 225-226° C.; $^1$H NMR (DMSO-d$_6$) δ 12.83 (s, 1H, NH), 8.00-7.92 (m, 4H, Ph), 5.32 (dd, J=5.6 Hz, J=12.9 Hz, 1H, H-3'), 3.28-3.25 (m, 2H, H-5'), 2.60-2.54 (m, 1H, H-4'), 2.17-2.10 (m, 1H, H-4'); $^{13}$C NMR (DMSO-d$_6$) δ 208.7(C-6'), 165.3(C-2'), 165.2(C-1 & C-3), 133.1(C-5 & C-6), 129.3 (C-3a, C-7a), 121.7 (C -4 & C-7), 46.9 (C-3'), 38.9 (C-5'), 21.79 (C-4'); MS (CI/CH$_4$) m/z 274 (M$^+$); Anal. (C$_{13}$H$_{10}$N$_2$O$_3$S) C, H, N.

Dimethyl 2-(1,3-dihydro-1,3-dioxo-2H-isoindol-2-yl) -pentanedioate (207). To a solution of N-phthaloyl-1-glutamic acid (200 mg, 0.72 mmol) in methanol (10 mL) was added, dropwise, thionyl chloride (1 mL). The reaction mixture was refluxed for 6 h. The solvent was removed under reduced pressure, dissolved in ethyl acetate (100 mL), and then washed with saturated aqueous Na$_2$CO$_3$ solution (2×30 mL) and water (2×30 mL). The ethyl acetate layer was dried over Na$_2$SO$_4$ and then evaporated, leaving an oil, which upon purification by silica gel chromatography, using CH$_2$Cl$_2$: EtOAc (1:1) as the eluent, gave compound 7 (161 mg, 73%) as an oil; $^1$H NMR (CDCl$_3$) δ 7.87-7.84 (m, 2H), 7.75-7.72 (m 2H), 4.91 (dd, J=5 Hz, J=9 Hz, 1H), 3.73 (s, 3H), 3.62 (s, 3H), 2.67-2.56 (m, 1H), 2.51-2.44 (m, 1H), 2.41-2.35 (m, 2H).

Dimethyl 2-(1,3-dihydro-1-oxo-3-thioxo-2H-isoindol-2-yl) -pentanedioate (208) and Dimethyl 2-(1,3-dihydro-1,3-dithioxo-2H-isoindol-2-yl)-pentanedioate (209). A mixture of compound 207 (144 mg, 0.47 mmol) and LR (191 mg, 0.47 mmol) in toluene was stirred in a 110° C. oil bath for 10 h. The solvent was then evaporated and the residue was purified by column chromatography, (silica gel) using CH$_2$Cl$_2$ as the eluent, to obtain compound 209 (17 mg, 11%) as a dark red oil. Thereafter, using CH$_2$Cl$_2$:EtOAc (10:1) as the eluent the more polar component 208 (105 mg, 70%) was obtained as a red oil.

Compound 208: $^1$H NMR (CDCl$_3$) δ 7.98-7.96 (m, 1H), 7.81-7.70 (m, 3H), 5.53 (dd, J=5.1 Hz, J=10 Hz, 1H), 3.70 (s, 3H), 3.59 (s, 3H), 2.76-2.56 (m, 2H), 2.40-2.33 (m, 2H); MS (CI/CH$_4$) m/z 321 (M$^+$).

Compound 209: $^1$H NMR (CDCl$_3$) δ 7.87-7.84 (m, 2H), 7.73-7.68 (m, 2H), 6.09 (dd, J=5 Hz, J=10 Hz, 1H), 3.70 (s, 3H), 3.58 (s, 3H), 2.81-2.63 (m, 2H), 2.40-2.24 (m, 2H); MS (DEI) m/z 337 (M$^+$); HRMS (DEI) calcd for C$_{15}$H$_{15}$NO$_4$S$_2$ 337.0442 (M$^+$). found 337.0449.

2-(1,3-Dihydro-1-oxo-3-thioxo-2H-isoindol-2-yl) -pentanedioic acid (211). Compound 208 (350 mg, 1.09 mmol) was stirred with a 1:1 mixture of acetic acid glacial and conc. HCl in a 100° C. oil bath for 2.5 h. Ethyl acetate (100 mL) and ice water (30 mL) were added. The ethyl acetate layer was separated, washed with ice water, dried over Na$_2$SO$_4$ and concentrated. The resulting syrup was crystallized with ether to afford compound 211 as red crystals (253 mg, 79%); mp 157° C.; $^1$H NMR (DMSO-d$_6$) δ 8.04-7.96 (m, 1H), 7.91-7.74 (m, 3H), 5.43 (dd, J=5.1 Hz, J=9.6 Hz, 1H), 2.42-2.33 (m, 2H), 2.30-2.26 (m, 2H); MS (DEI) m/z 293 (M); HRMS (DEI) calcd. for C$_{13}$H$_{11}$NO$_5$S 293.0358 (M+). found 293.0363; Anal. (C$_{13}$H$_{11}$NO$_5$S) H, N; C: calcd, 53.24. found, 53.88.

2,3-Dihydro-3-thioxo-2-(2,6-dioxo-3-piperidiny)-1H -isoindol-1-one (212).

A mixture of compound 208 (81 mg, 0.276 mmol), trifluoroacetamide (57 mg, 0.50 mmol), 1-hydroxybenzotriazole (145 mg, 1.07 mmol), 1-[3-(dimethylamino)propyl]-3-ethyl-carbodiimide hydrochloride (200 mg, 1.04 mmol) and triethylamine (0.21 mL, 1.51 mmol) in CH$_2$Cl$_2$ (1.5 mL) was stirred at ambient temperature for 3 days. Water (10 mL) and CH$_2$Cl$_2$ (10 mL) were added. The dichloromethane layer was separated, washed with water, dried over Na$_2$SO$_4$ and evaporated under reduced pressure. Purification by chromatography, with EtOAc:CH$_2$Cl$_2$ (1:10) as the eluent, gave compound 212 (48 mg, 63%) as a red solid: mp 255° C.; $^1$H NMR (CDCl$_3$) δ 8.00-7.98 (m, 1H), 7.80-7.71 (m, 3H), 5.63 (br, 1H), 2.98-2.70 (m, 3H), 2.18-2.15 (m, 1H); MS (CI/CH$_4$) m/z 274 (M$^+$); Anal. (C$_{13}$H$_{10}$N$_2$O$_3$S) C, H, N.

2-(2,6-Dithioxo-3-piperidinyl)-1H-isoindole-1,3(2H)-dione (213) and 2,3-dihydro-3-thioxo-2-(2-oxo-6-thioxo-3-piperidinyl)-1H -isoindol-1-one (215). The mixture of 205 (146 mg, 0.533 mmol), LR (108 mg, 0.267 mmol) and pyridine (21 μl) in toluene was stirred at 110° C. under an atmosphere of N$_2$ for 12 h. Thereafter, additional LR (108 mg, 0.267 mmol) and pyridine (21 μl) were added, and the reaction mixture was stirred for a further 12 h. The solvent was removed under vacuum and the residue was purified by column chromatography with CH$_2$Cl$_2$:petroleum ether (2:1, 10:1) and then CH$_2$Cl$_2$:EtOAc (10:1) as eluents to afford 213 (30 mg, 45%), 215 (21 mg, 31.5%) and starting material 205 (83 mg).

Compound 213 (yellow solid): mp 263-265° C.; $^1$H NMR (CDCl$_3$) δ 7.78-7.74 (m, 2 H), 7.66-7.63 (m, 2 H), 5.00 (dd, J=4.9 Hz, 11.9 Hz, 1 H), 3.43-3.35 (m, 1 H), 2.95-2.84 (m, 2 H), 2.08-2.06 (m, 1 H); MS (DEI) m/z 290 (M); HRMS (DEI) calcd for C$_{13}$H$_{11}$N$_2$O$_2$S$_2$ 290.0184 (M). found 290.0185; Anal. (C$_{13}$H$_{10}$N$_2$O$_2$S$_2$) C, H, N.

Compound 215 (red solid): mp 240-242° C.; $^1$H NMR (CDCl$_3$) δ 9.44 (s, 1 H), 8.05-8.02 (m, 1 H), 7.86-7.76 (m, 3 H), 5.75-5.64 (m, 1 H), 3.57-3.52 (m, 1 H), 3.09-2.99 (m, 2 H), 2.19-2.12 (m, 1 H). $^{13}$C NMR DMSO): 208.16, 207.98, 166.10, 165.39, 134.32, 133.11, 132.42, 124.30, 122.15, 121.11, 49.64, 21.29; MS (DEI) m/z 291 (MH$^+$); HRMS (DEI) calcd for C$_{13}$H$_{11}$N$_2$O$_2$S$_2$ 291.0262 (M). found 291.0264; Anal. (C$_{13}$H$_{10}$N$_2$O$_2$S$_2$.0.5H$_2$O) C, H, N.

2,3-Dihydro-3-thioxo-2-(2,6-dithioxo-3-piperidinyl)-1H-isoindol-1-one (216). A mixture of compound 213 (29 mg, 0.1 mmol), LR (22 mg, 0.054 mmol) and morpholine (9 μl, 0.1 mmol) in toluene (10 mL) was stirred at reflux under an atmosphere of N$_2$ for 16 h. The solvent was removed under vacuum and the residue was purified by column chromatography using CH$_2$Cl$_2$:petroleum ether (1:1) as the eluent to afford compound 216 (20 mg, 65%) as a red solid: mp 244° C.; $^1$H NMR (CDCl$_3$) δ 10.81 (s, 1H), 8.05-8.01 (m, 1H), 7.91-7.75 (m, 3H), 5.92 (m, 1H), 3.57-3.52 (m, 1H), 3.13-2.97 (m, 2H), 2.18-2.15 (m, 1H); MS(DEI) m/z 306 (M$^+$); HRMS (DEI) calcd for C$_{13}$H$_{10}$N$_2$OS$_3$ 305.9955 (M$^+$). found 305.9951; Anal. (C$_{13}$H$_{10}$N$_2$OS$_3$.0.5H$_2$O) C, H, N.

6-Thioxo-2-piperidinone (218). The mixture of glutarimide (0.45 g, 4 mmol) and LR (0.809 g, 2 mmol) in THF (30 mL) was stirred at room temperature for 2 days. The solvent was evaporated under vacuum and the residue was purified by column chromatography using petroleum ether:EtOAc (1:1) as the eluent to give compound 218 as a yellow solid (0.361 g, 70%): mp 135° C.; $^1$H NMR (CDCl$_3$) δ 2.96 (t, J=5.7 Hz, 2 H), 2.58 (t, J=5.8 Hz, 2 H), 1.96 (m, 2 H); MS (CI/CH$_4$) m/z 129 (M$^+$); Anal. (C$_5$H$_7$NOS) C, H, N.

2,6-Piperidinedithione (219). A mixture of glutarimide (0.34 g, 3 mmol) and LR (1.22 g, 3 mmol) in toluene (30 mL) was stirred at reflux for 3 h. The solvent was evaporated under vacuum and the residue was purified by column chromatography using petroleum ether:EtOAc (20:1) as the eluent to give compound 219 as a yellow solid (0.286 g, 66%): mp 103° C.; $^1$H NMR (CDCl$_3$) δ 3.02 (t, J=6.3 Hz, 4H), 1.98 (t, J=6.3 Hz, 2H); MS (CI/CH$_4$) m/z 145 (M$^+$); Anal. (C$_5$H$_7$NS$_2$) C, H, N.

2-(3-Cyclohexenyl)-1H-isoindole-1,3(2H)-dione (221). A mixture of potassium phthalimide (1.85 g, 3 mmol) and 3-bromocyclohexene (1.79 g, 3 mmol) in DMF (15 mL) was stirred in a 100° C. oil bath for 12 h. The cooled reaction mixture was poured into ice water. The solid was collected by filtration and purified by flash chromatography with CH$_2$Cl$_2$ as the eluent to afford compound 221 (1.6 g, 72%) as pink crystals; mp 114° C.; $^1$H NMR (CDCl$_3$) δ 7.73-7.69 (m, 2H), 7.62-7.58 (m, 2H), 5.85-5.82 (m, 1H), 5.47-5.44 (m, 1H), 4.80-4.78 (m, 1H), 2.14-2.00 (m, 3H), 1.86-1.78 (m, 2H), 1.64-1.58 (m, 1H).

2-(3-Cyclohexenyl)-1H-isoindol-1,3(2H)-dithione (222) and 2,3-dihydro-3-thioxo-2-(3-cyclohexenyl)-1H-isoindol-1-one (223). A mixture of compound 221 (68 mg, 0.3 mmol) and LR (121 mg, 0.3 mmol) in toluene was refluxed under N$_2$ for 10 h. The solvent was removed under vacuum and the residue was purified by column chromatography using petroleum ether as the eluent to obtain compound 222 (37 mg, 48%) as a dark green solid. Then, using CH$_2$Cl$_2$:petroleum ether (1:1) as the eluent, the more polar component 223 (23 mg, 32%) was obtained as a red solid.

Compound 222: mp 93° C.; $^1$H NMR (CDCl$_3$) δ 7.65-7.60 (m, 2H), 7.49-7.42 (m, 2H), 5.92-5.88 (m, 1H), 5.66-5.63 (m, 1H), 5.47-5.43 (m, 1H), 2.40-2.35 (m, 1H), 1.99-1.95 (m, 2H), 1.75-1.59 (m, 3H); MS (CI/CH$_4$) m/z 259 (M$^+$); Anal. (C$_{14}$H$_{13}$NS$_2$) C, H, N.

Compound 223: mp 67-68° C.; $^1$H NMR (CDCl$_3$) δ 7.94-7.91 (m, 1H), 7.73-7.64 (m, 3H), 5.92-5.88 (m, 1H), 5.60-5.51 (m, 2H), 2.27-2.10 (m, 3H), 1.96-1.76 (m, 2H), 1.81-1.70 (m, 1H); MS (CI/CH$_4$) nz/z 243 (M$^+$); Anal. (C$_{14}$H$_{13}$NOS) C, H, N.

Dithiophthalimide (225). A mixture of phthalimide (436 mg, 3.40 mmol) and Lawesson's reagent (1.199 g, 3.40 mmol) in toluene (50 ml) was refluxed (oil bath 120° C.) under nitrogen for 5 hours. The solvent was removed under vacuum and the residue was directly chromatographed (silica gel, petroleum ether:methylenedichloride/2:3) to give dithiophthalimide as black red needle crystals (240 mg, 39.4%): $^1$HNMR(CDCl$_3$) δ 9.80 (br, 1H), 7.95 (d, 2H), 7.80 (d, 2H); MS (CI/CH$_4$) m/z 179 (M$^+$).

Example 12

Synthesis and TNF-α Inhibitory Activity of 3-[2',6'-piperidinedion-3'-yl]-7-amino-2H-1,3-benzoxazine-2,4(3H)-dione 3-[2',6'-piperidinedion-3'-yl]-7-amino-2H-1,3-benzoxazine-2,4(3H)-dione was prepared as shown below in Scheme 17.

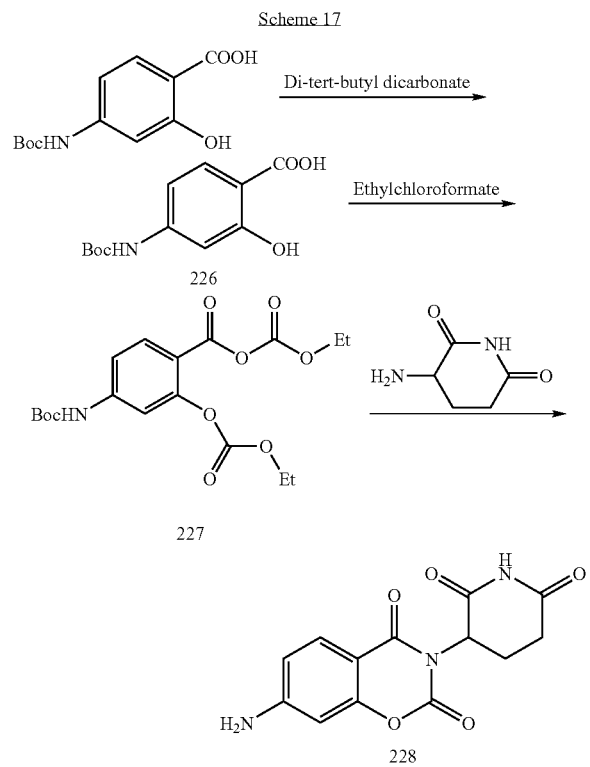

4-(t-Butoxycarbonyl amido)salicylic acid (226) was prepared as follows. To a mixture of 4-aminosalicylic acid (306 mg, 2 mmol) and di-t-butyl dicarbonate (655 mg, 3 mmol) in H$_2$O was added NaOH (2N in H$_2$O) at 0° C. This reaction mixture was allowed to warm to room temperature and then was stirred for 5 hours. 2N HCl was added dropwise until the mixture was neutralized. The reaction mixture was then extracted with EtOAc, dried and evaporated to give product (336 mg, 66%) as a dark gray solid: $^1$HNMR (DMSO-$d_6$) δ 11.50 (s, 1H), 7.65 (d, 1H), 6.23 (d, 1H), 6.07 (s, 1H), 1.70 (s, 9H).

2-[(Ethoxycarbonyl)oxy]-4-(t-butoxycarbonyl amido)-benzoic anhydride with ethyl hydrogencarbonate (227) was prepared as follows. 4-t-Butoxycarbonyl amidosalicylic acid (226) (101 mg, 0.399 mmol) in THF (10 ml) was cooled with dry ice in acetone. Et$_3$N (0.166 ml) was added, and then ethyl chloroformate (108 mg, 1.135 mmol) was added dropwise over a period of 30 min. The reaction mixture was stirred at the same temperature for 5 hours, and then was allowed to warm to room temperature. Thereafter, the reaction mixture was stirred continuously overnight. After evaporation of solvent, the residue was partitioned between water and ethyl ether. The ether solution was washed with brine, dried over Na$_2$SO$_4$ and evaporation of solvent gave product (111 mg, 70%) as a yellow gum: $^1$HNMR (CDCl$_3$) δ 7.75 (d, 1H), 6.48 (d, 1H), 6.38 (s, 1H), 4.38 (m, 4H), 1.35 (m, 6H).

3-[2',6'-piperidinedion-3'-yl]-7-amino-2H-1,3-benzoxazine-2,4(3H)-dione (228) was prepared as follows. A mixture of 227 (32.8 mg, 0,0826 mmol), aminoglutarimide (20 mg, 0.0826 mmol) and Et$_3$N (25.0 mg, 0.248 mmol in 2 ml THF) was stirred at room temperature overnight. Evaporation of solvent gave a residue which was stirred with a mixture of EtOAc and a saturated aqueous solution of NaHCO$_3$. The precipitated white solid was collected by filtration as the product: $^1$HNMR (DMSO-$d_6$) δ 11.3 (br, 1H), 7.85 (d, 1H), 6.80 (d, 1H), 6.60 (s, 1H), 3.15 (t, 2H), 2.15 (t, 2H).

Evaluation of compound 228 in the TNF-α assay described above in Example 11 showed that it possessed potent inhibitory action on TNF-α, having an EC$_{50}$ of 0.4 μM.

Example 13

Angiogenesis Modulating Activity

Angiogenesis is the formation of new blood vessels from pre-existing vessels. Angiogenesis is prominent in solid tumor formation and metastasis, and is part of the wound healing process. Pathological angiogenesis sometimes occurs in inappropriate anatomic locations, such as the retina or cornea, in response to disease and injury. Inhibition of angiogenesis could avoid the progression of conditions of inappropriate angiogenesis.

Tumor formation, for example, requires a network of blood vessels to sustain the nutrient and oxygen supply for continued growth. Tumors in which angiogenesis is important include most solid tumors and benign tumors, such as acoustic neuroma, neurofibroma, trachoma, and pyogenic granulomas. Inhibition of angiogenesis could halt the growth of these tumors and the resultant damage due to the presence of the tumor.

There is a direct correlation between tumor microvessel density and the incidence of metastasis. Tumor cells themselves can produce factors that stimulate the proliferation of endothelial cells and new capillary growth. Angiogenesis is important in two stages of tumor metastasis. The first stage where angiogenesis stimulation is important is in the vascularization of the primary tumor, which allows tumor cells to enter the blood stream and to circulate throughout the body. After the tumor cells have left the primary site, and have settled into the secondary, metastatic site, angiogenesis must occur before the metastasis can grow and expand. Therefore, inhibiting angiogenesis could lead to the reduction or elimination of metastasis of tumors and possibly contain the neoplastic growth at the primary site. These observations have led to the investigation of anti-angiogenic agents as possible therapeutic options for various cancers.

The angiogenesis modulating activity of representative compounds was assessed in a rat aortic ring microvessel growth assay. Briefly, twelve-well tissue culture plates were coated with 250 μl of Matrigel (Becton-Dickinson, Bedford, Mass.) and allowed to gel for 30 min at 37° C. and 5% CO$_2$. Thoracic aortas were excised from 8- to 10-week-old male Sprague Dawley rats. After careful removal of fibroadipose tissues, the aortas were cut into 1-mm-long cross-sections, placed on Matrigel-coated wells, and covered with an additional 250 μl of Matrigel. After the second layer of Matrigel had set, the rings were covered with EGM-II and incubated overnight at 37° C. and 5% CO2. EGM-II consists of endothelial cell basal medium (EBM-II; Clonetics, San Diego, Calif.) plus endothelial cell growth factors provided as the EGM-II Bulletkit (Clonetics). The culture medium was subsequently changed to EBM-II supplemented with 2% fetal bovine serum, 0.25 μg/ml amphotericin B, and 10 μg/ml gentamicin. Aortic rings were treated daily with either the vehicle (0.5% DMSO), carboxyamidotriazole (CA, 12 μg/ml), thalidomide or thalidomide analogs (0.1-20 μg/ml) for 4 days and photographed on the 5th day using a ×2.5 objective. CAI, a known antiangiogenic agent, was used at higher than clinically achievable concentration as a positive control. Experiments were repeated four times using aortas from four different rats. The area of angiogenic sprouting, reported in square pixels, was quantified using Adobe PhotoShop. Further details of the method are provided in Luzzio et al., *J Med Chem.*; 46:3793-9, 2003, which is incorporated by reference herein. It should be understood that this method can be used as an assay to rapidly select compounds having a desired angiogenic or anti-angiogenic effect, for example, for use in the disclosed methods of treating a subject.

Bar graphs showing the results of the angiogenesis assay for several compounds are shown in FIGS. 2-11. For convenience, the structures of the assayed compounds also are presented in these figures.

Figure 2:
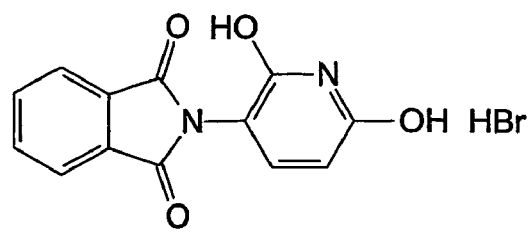
FIG. 2 is a bar graph showing the relative angiogenic modulating activity of 1,3-Dioxo-2-(2-hydroxy-6-methoxy-pyridin-3-yl)-isoindoline hydrobromide at several concentrations.
Figure 2:
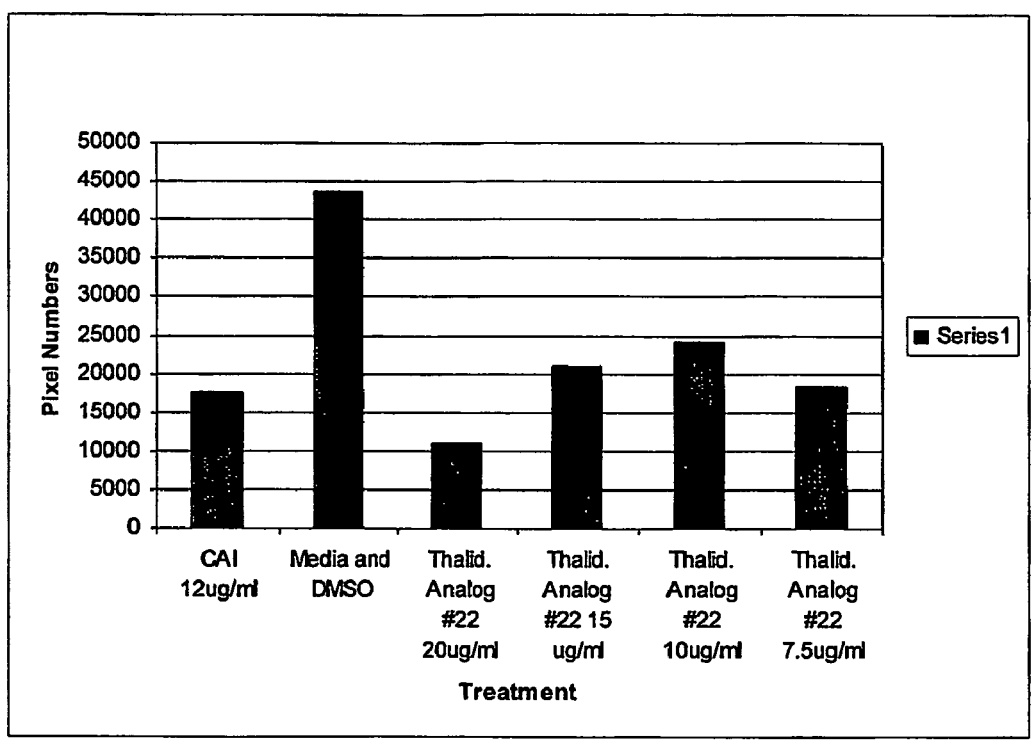

FIG. 2 shows the angiogenic modulating activity of 1,3-Dioxo-2-(2-hydroxy-6-methoxypyridin-3-yl)-isoindoline hydrobromide at several concentrations. This compound exhibited anti-angiogenic activity in the rat aortic ring assay at all concentrations tested.

Figure 3:
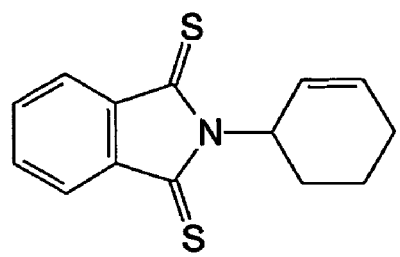
FIG. 3 is a bar graph showing the relative angiogenic modulating activity of 2-(3-cyclohexenyl)-H-isoindol-1,3 (2H)-dithione at several concentrations.
Figure 3:
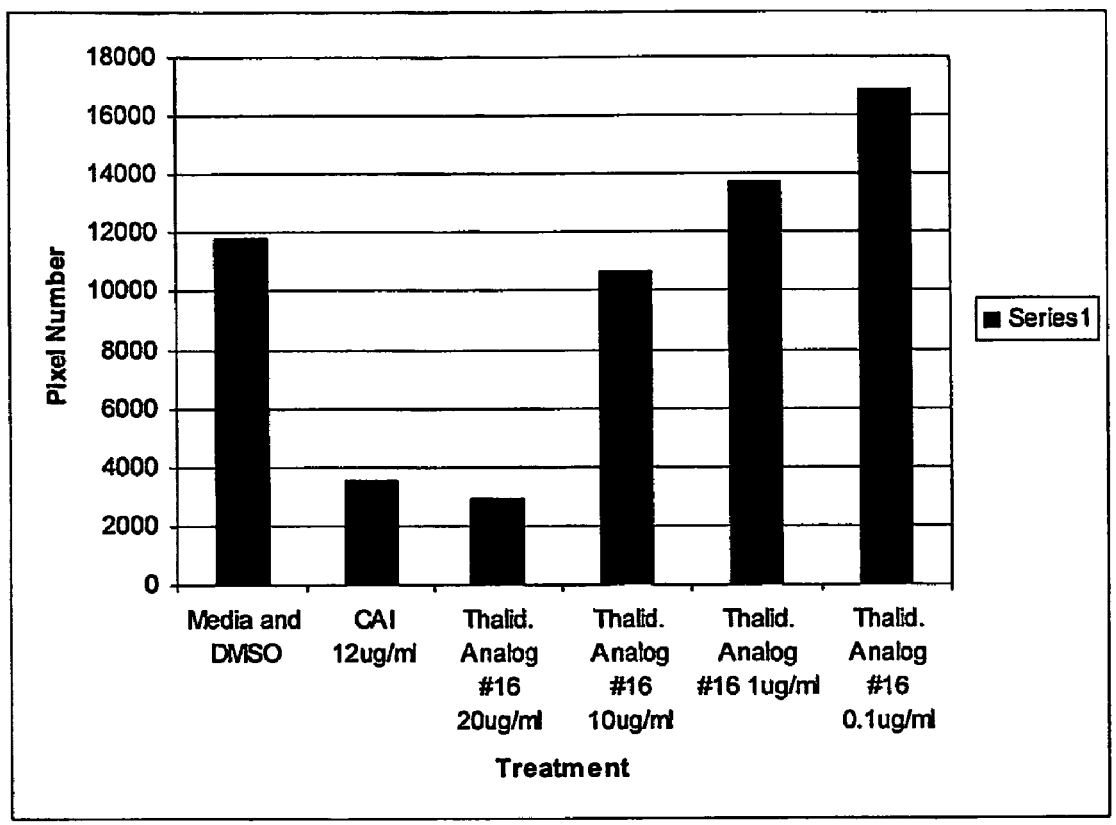

FIG. 3 shows the angiogenic modulating activity of 2-(3-cyclohexenyl)-H-isoindol -1,3(2H)-dithione at several concentrations. This compounds exhibited anti-angiogenic activity at higher concentrations and angiogenic activity at lower concentrations.

Figure 4:
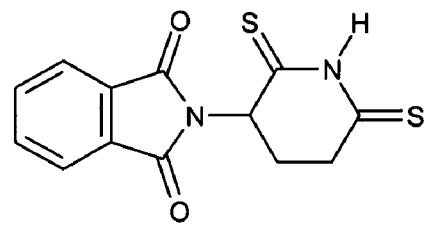
FIG. 4 is a bar graph showing the relative angiogenic modulating activity of 1-(2,6-Dithioxo-3-piperidinyl)-1H-isoindole-1,3(2H)-dione at several concentrations.
Figure 4:
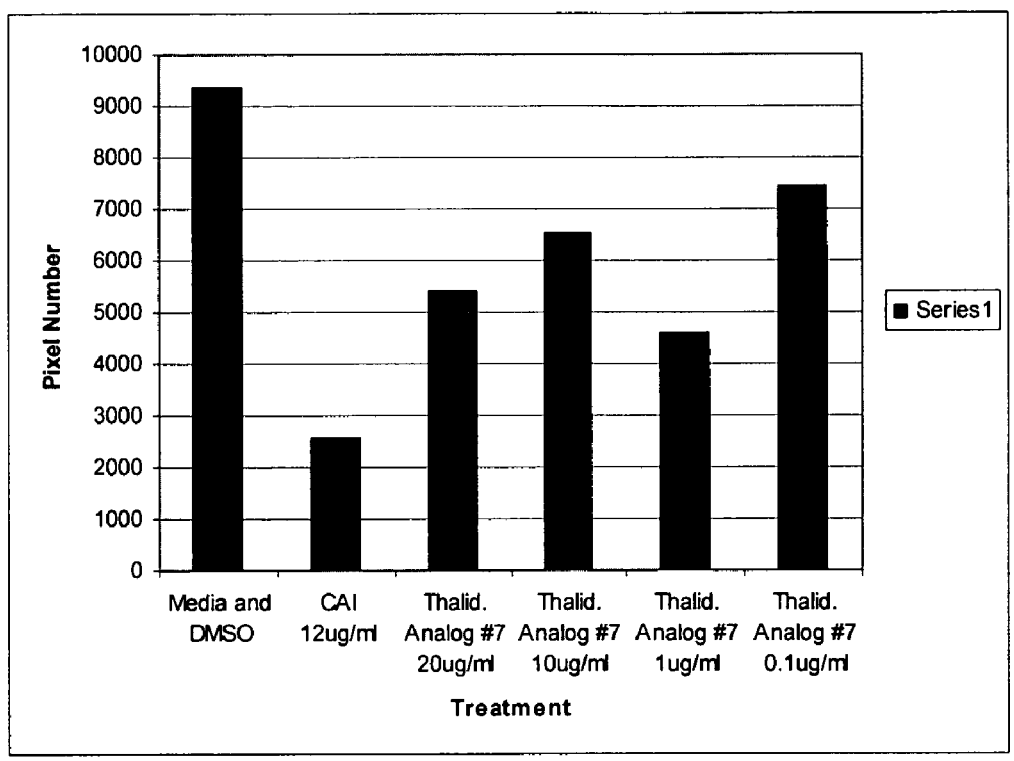

FIG. 4 shows the angiogenic modulating activity of 1-(2, 6-Dithioxo-3-piperidinyl)-1H-isoindole-1,3(2H)-dione at several concentrations. This compound exhibited anti-angiogenic activity at all concentrations tested.

Figure 5:
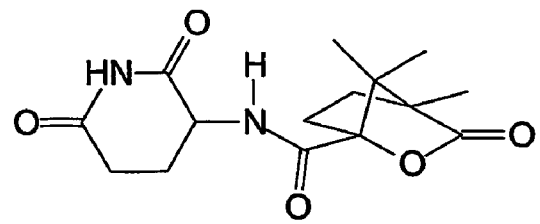
FIG. 5 is a bar graph showing the relative angiogenic modulating activity of 3-Camphanic amino-2,6-piperidinedione at several concentrations.
Figure 5:
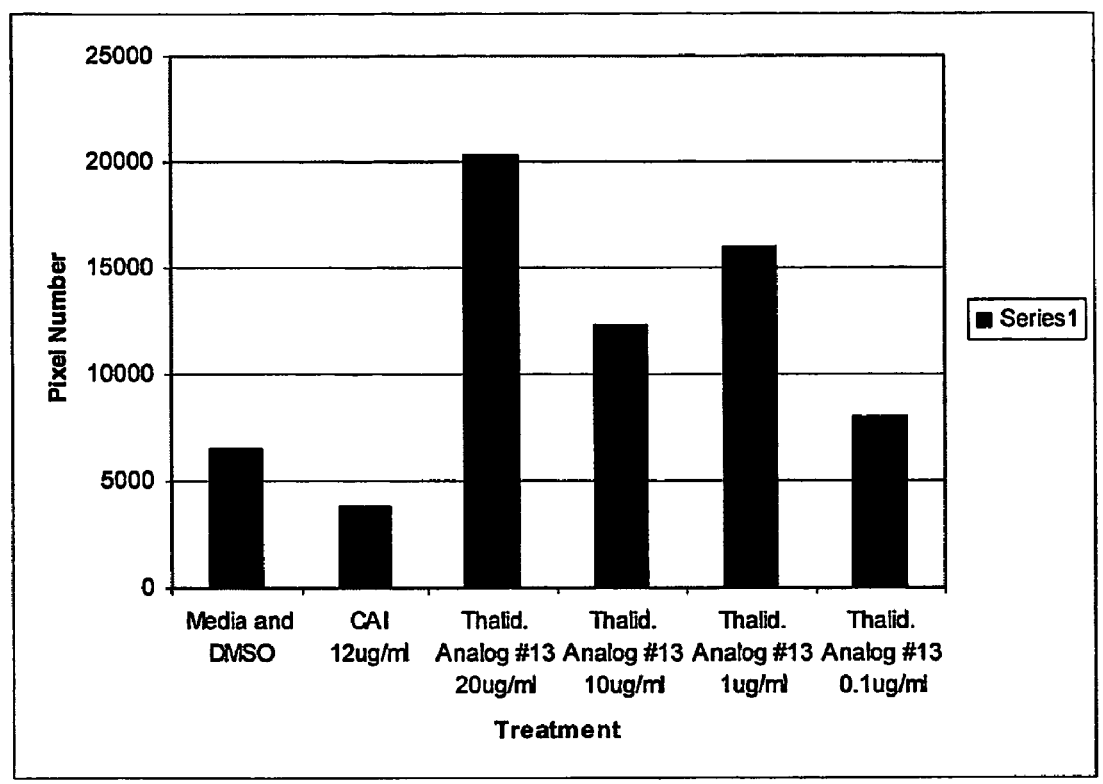

FIG. 5 shows the angiogenic modulating activity of 3-Camphanic amino-2,6-piperidinedione at several concentrations. This compound exhibited potent angiogenic activity at all concentrations tested, making this compound promising for treating conditions where increased angiogenesis is desired, for example, as an aid to wound healing.

Figure 6:
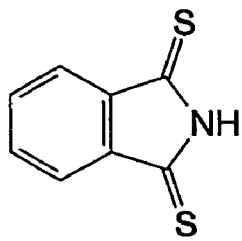
FIG. 6 is a bar graph showing the relative angiogenic modulating activity of Dithiophthalimide at several concentrations.
Figure 6:
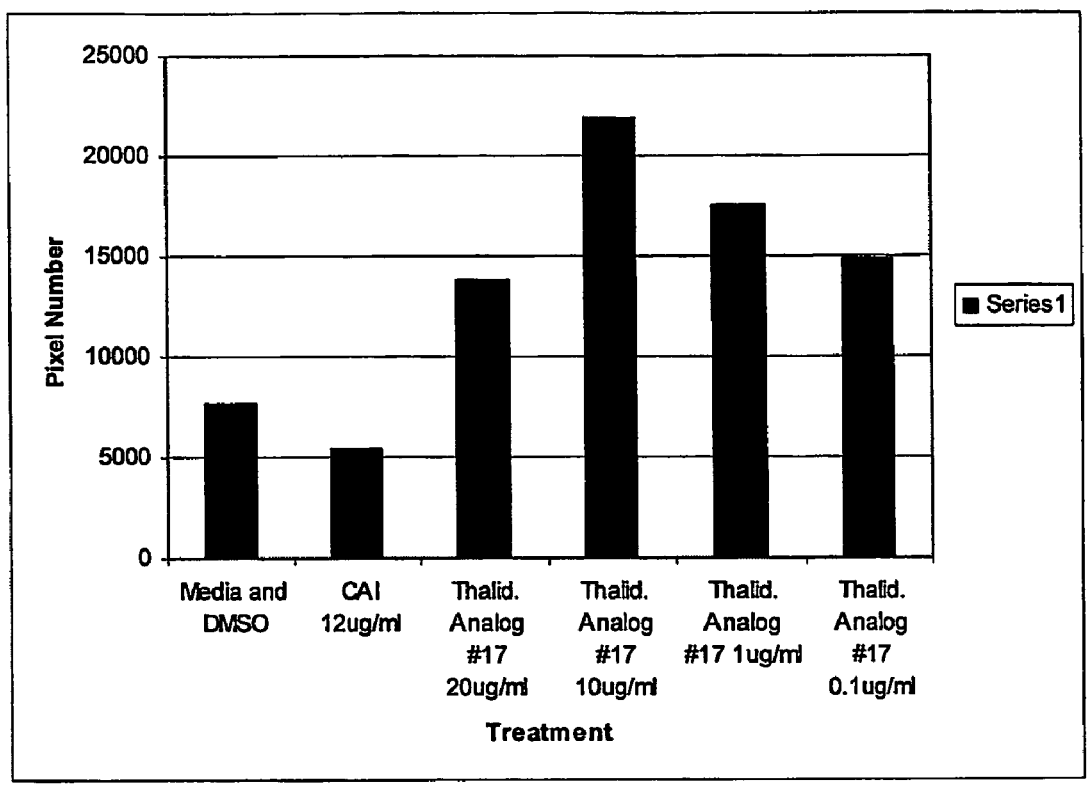

FIG. 6 shows the angiogenic modulating activity of Dithiophthalimide at several concentrations. This compound exhibited angiogenic activity at all concentrations tested.

Figure 7:
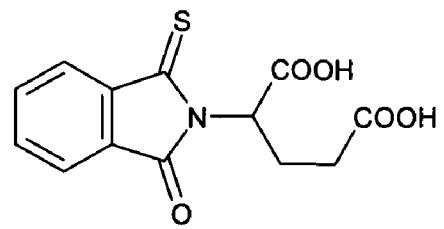
FIG. 7 is a bar graph showing the relative angiogenic modulating activity of 2-(1,3-Dihydro-1-oxo-3-thioxo-2H-isoindol-2-yl)-pentanedioic acid at several concentrations.
Figure 7:
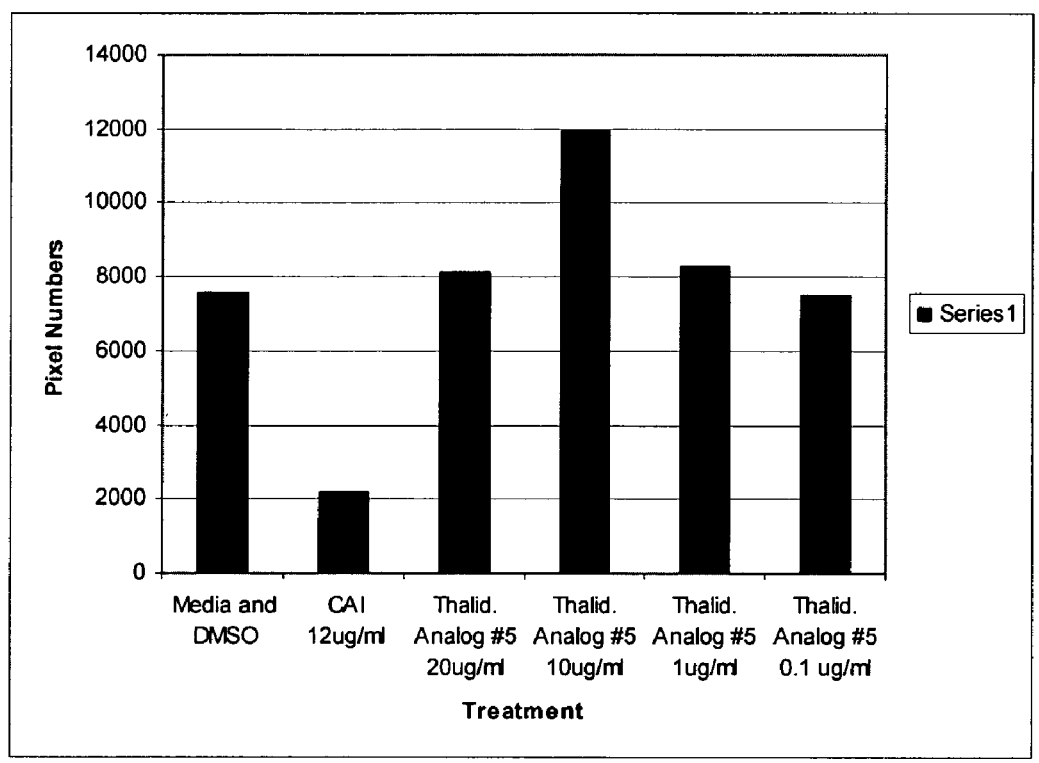

FIG. 7 shows the angiogenic modulating activity of 2-(1, 3-Dihydro-1-oxo-3-thioxo-2H-isoindol-2-yl)-pentanedioic acid at several concentrations. This compound exhibited angiogenic activity at all concentrations tested.

Figure 8:
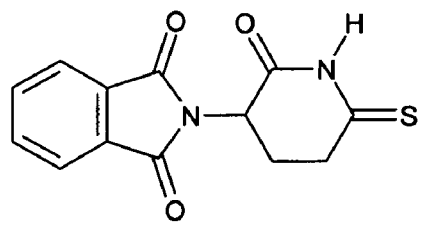
FIG. 8 is a bar graph showing the relative angiogenic modulating activity of 2-(2-Oxo-6-thioxo-3-piperidinyl)-1H-isoindole-1,3(2H)-dione at several concentrations.
Figure 8:
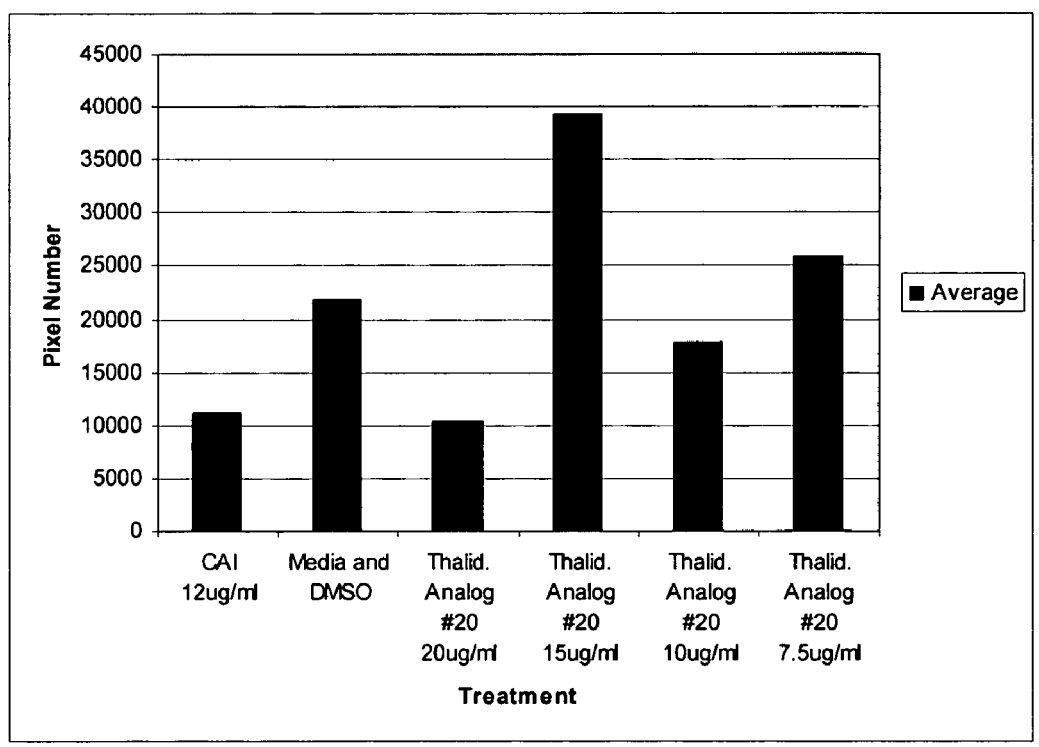

FIG. 8 shows the angiogenic modulating activity of 2-(2-Oxo-6-thioxo-3-piperidinyl)-1H-isoindole-1,3(2H)-dione at several concentrations. This compound showed anti-angiogenic activity at higher concentration, and some angiogenic activity at lower concentrations.

Figure 9:
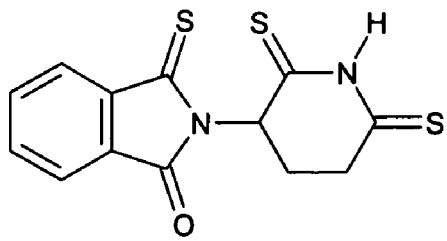
FIG. 9 is a bar graph showing the relative angiogenic modulating activity of 2,3-Dihydro-3-thioxo-2-(2,6-dithioxo-3-piperidinyl)-1H-isoindol-1-one at several concentrations.
Figure 9:
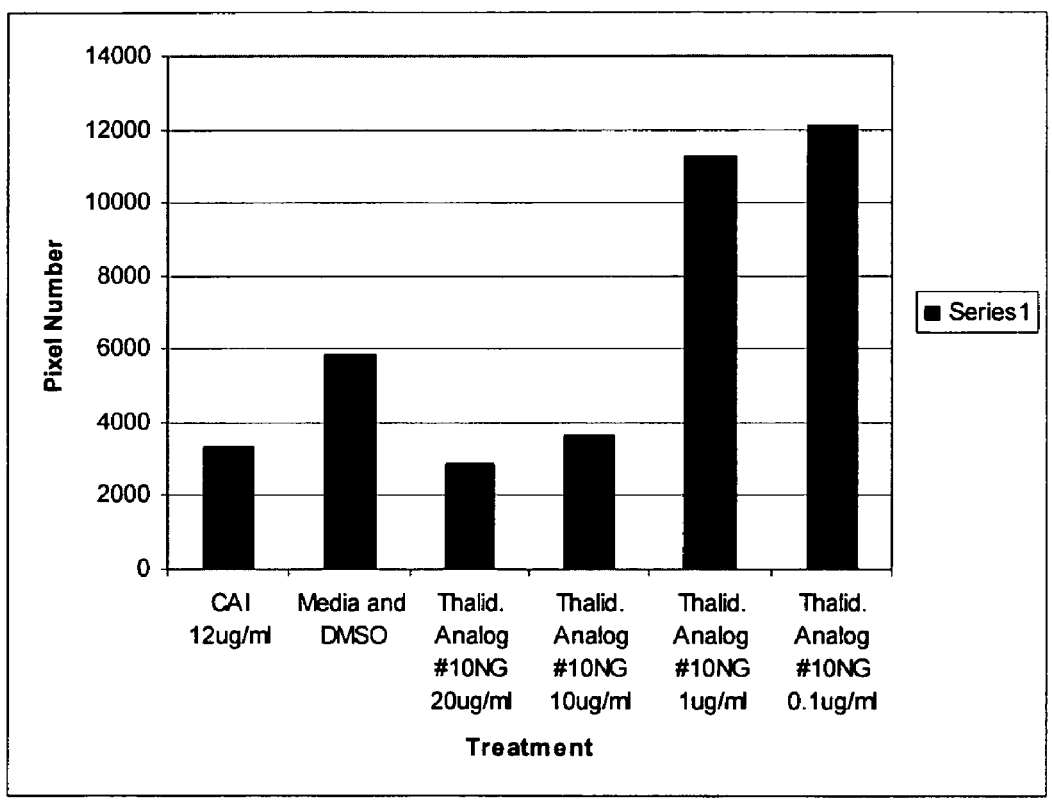

FIG. 9 shows the angiogenic modulating activity of 2,3-Dihydro-3-thioxo-2-(2,6-dithioxo-3-piperidinyl)-1H-isoindol-1-one at several concentrations. This compound exhibited potent anti-antigiogenic activity at higher concentrations and angiogenic activity at lower concentrations.

Figure 10:
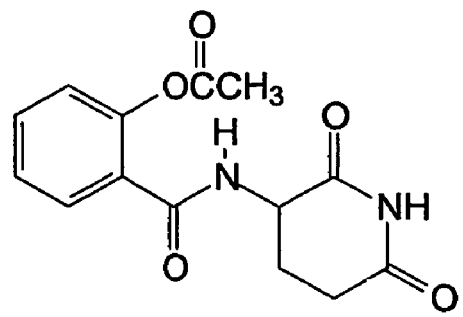
FIG. 10 is a bar graph showing the relative angiogenic modulating activity of 2-Acetoxy-N-(2,6-dioxopiperidin-3-yl)benzamide at several concentrations.
Figure 10:
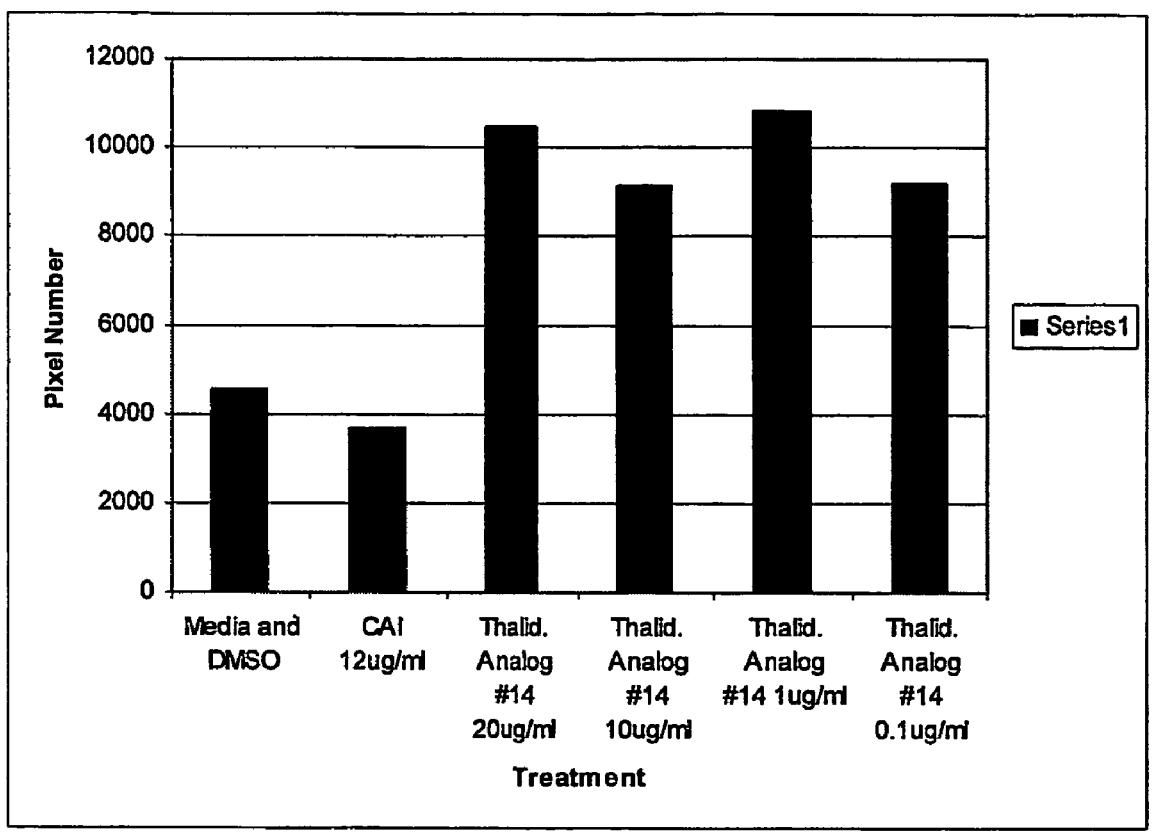

FIG. 10 shows the angiogenic modulating activity of 2-Acetoxy-N-(2,6-dioxopiperidin-3-yl)benzamide at several concentrations. At all concentrations tested, this compound exhibited potent angiogenic activity.

Figure 11:
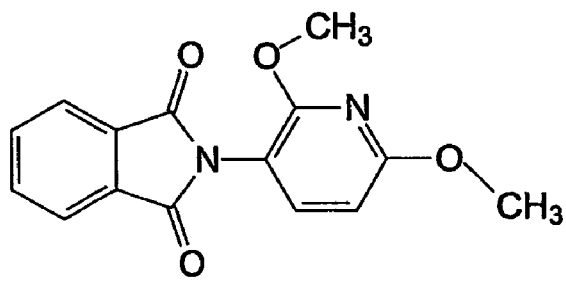
FIG. 11 is a bar graph showing the relative angiogenic modulating activity of 1,3-Dioxo-2-(2,6-dimethoxypyridin-3-yl)-isoindoline at several concentrations.
Figure 11:
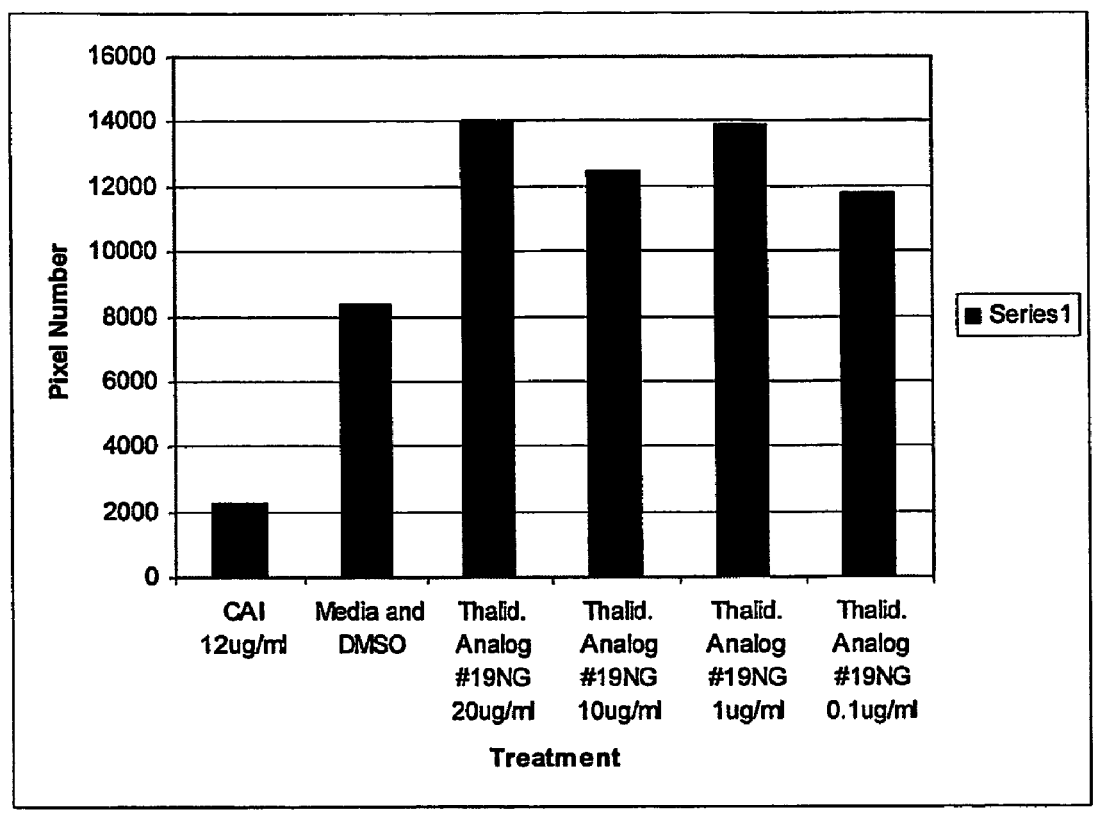

FIG. 11 shows the angiogenic modulating activity of 1,3-Dioxo-2-(2,6-dimethoxypyridin-3-yl)-isoindoline at several concentrations. This compound exhibited angiogenic activity at all concentrations tested.

In summary, the disclosed compounds exhibit a range of angiogenic modulating activities ranging from potent inhibition of angiogenesis (anti-angiogenic activity) to potent stimulation of angiogenesis (angiogenic activity). Some compounds exhibit both angiogenic and anti-angiogenic activity in a dose-dependent manner. Those compounds (or particular concentrations thereof) having angiogenic activity are useful for treating conditions or diseases where increasing angiogenesis is desirable (for example, wound healing) and those compounds (or particular concentrations thereof) having anti-angiogenic activity are useful for treating conditions or diseases where decreasing angiongenesis is desirable (for example, cancers, diabetic retinopathy or corneal neovascularization). Persons of ordinary skill in the art can use the assay described above (or other known angiogenic/anti-angiogenic activity assays) to readily determine amounts of the disclosed compounds that therapeutically effective for stimulating or inhibiting angiogenesis as appropriate for a given subject's condition.

Example 14

Synthesis of 3-Camphanic amino-2,6-piperidinedione

A mixture of (+)-camphanic chloride (19 mg, 00868 mmol), aminoglutarimide (21 mg, 0.0868 mmol) and $Et_3N$ (24 µl) in $CHCl_3$ (1 ml) was stirred at room temperature for 16 hours. The solution was diluted with $CHCl_3$, washed with saturated aqueous solution of $NaHCO_3$, dried over $Na_2SO_4$, concentrated and purified by chromatography (silica gel, CH2Cl2; EtOAc=10:1) to give product (16 mg, 60.0% yield) as a colorless gel: $^{13}CNMR$ ($CDCl_3$) δ 172.6, 169.4, 168.6, 165.5, 90.3, 58.3, 53.3, 48.2, 47.6, 29.2, 28.2, 26.9, 22.7, 14.6, 7.6; MS ($CI/CH_4$) m/z 308 ($M^+$). This compound exhibited angiogenic activity in the assay of Example 13.

Example 15

Synthesis of 3-Benzylimino-2-benzyl-2,3-dihydroisoindol-1-one

A solution of Dimethyl 2-(1,3-dihydro-1-oxo-3-thioxo-2H-isoindol-2-yl)-pentanedioate (compound 208 of Example 11, 100 mg, 0.311 mmol) and benzylamine was stirred in a 50° C. oil bath for 5 hours. The reaction mixture was partitioned between water and ethyl acetate. The organic layer was washed with water, dried, and concentrated. The residue was purified by chromatography (silica gel, $CH_2Cl_2$) to give product as white crystals (60 mg, 59.0%): $^1HNMR$ ($CDCl_3$) δ 7.10-7.90 (m, 10H), 5.18 (s, 2H), 4.95 (s, 2H); $^{13}C$ NMR ($CDCl_3$) δ 167.8, 151.3, 140.6, 138.2, 133.5, 133.3, 132.1, 130.4, 130.1, 129.1, 128.8, 128.7, 128.5, 128.4, 127.9, 127.6, 127.5, 127.2, 126.0, 124.1, 53.9, 42.5; FAB-MS m/z 327 ($MH^+$). This compound exhibited angiogenic activity in the assay of Example 13.

Example 16

Thionation

Although many of the disclosed compounds are illustrated without thionyl groups in their structures, it is to be understood that any of the carbonyl groups shown in the structures of the disclosed compounds may be converted into thiocarbonyl groups, and that such thio-derivatives are part of this disclosure. Thionation may be accomplished by any known method. Particular methods of thionation include use of phosphorus pentasulfide, hydrogen sulfide, O,O-diethyldithiophosphonic acid, boron sulfide, silicon disulfide and elemental sulfur in HMPA. However, a particularly convenient method of thionation is the use of 2,4-bis(p-methoxyphenyl)-1,3-dithiadiphosphetane-2,4-disulfide and its derivatives (generically "Lawesson's Reagents"). These reagents are described in Cava and Levinson, "Thionation Reactions of Lawesson's Reagents," *Tetrahedron*, 41: 5061-5087, 1985, which is incorporated by reference herein.

Example 17

Pharmaceutical Compositions

The disclosed pharmaceutical compositions can be in the form of tablets, capsules, powders, granules, lozenges, liquid or gel preparations, such as oral, topical, or sterile parenteral solutions or suspensions (e.g., eye or ear drops, throat or nasal sprays, etc.), transdermal patches, and other forms known in the art.

Pharmaceutical compositions can be administered systemically or locally in any manner appropriate to the treatment of a given condition, including orally, parenterally, rectally, nasally, buccally, vaginally, topically, optically, by inhalation spray, or via an implanted reservoir. The term "parenterally" as used herein includes, but is not limited to subcutaneous, intravenous, intramuscular, intrasternal, intrasynovial, intrathecal, intrahepatic, intralesional, and intracranial administration, for example, by injection or infusion. For treatment of the central nervous system, the pharmaceutical compositions may readily penetrate the blood-brain barrier when peripherally or intraventricularly administered.

Pharmaceutically acceptable carriers include, but are not limited to, ion exchangers, alumina, aluminum stearate, lecithin, serum proteins (such as human serum albumin), buffers (such as phosphates), glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Tablets and capsules for oral administration can be in a form suitable for unit dose presentation and can contain conventional pharmaceutically acceptable excipients. Examples of these include binding agents such as syrup, acacia, gelatin, sorbitol, tragacanth, and polyvinylpyrrolidone; fillers such as lactose, sugar, corn starch, calcium phosphate, sorbitol, or glycine; tableting lubricants, such as magnesium stearate, talc, polyethylene glycol, or silica; disintegrants, such as potato starch; and dispersing or wetting agents, such as sodium lauryl sulfate. Oral liquid preparations can be in the form of; for example, aqueous or oily suspensions, solutions, emulsions, syrups or elixirs, or can be presented as a dry product for reconstitution with water or other suitable vehicle before use.

The pharmaceutical compositions can also be administered parenterally in a sterile aqueous or oleaginous medium. The composition can be dissolved or suspended in a non-toxic parenterally-acceptable diluent or solvent, e.g., as a solution in 1,3-butanediol. Commonly used vehicles and solvents include water, physiological saline, Hank's solution, Ringer's solution, and sterile, fixed oils, including synthetic mono- or di-glycerides, etc. For topical application, the drug may be made up into a solution, suspension, cream, lotion, or ointment in a suitable aqueous or non-aqueous vehicle. Additives may also be included, for example, buffers such as sodium metabisulphite or disodium edeate; preservatives such as bactericidal and fungicidal agents, including phenyl mercuric acetate or nitrate, benzalkonium chloride or chlorhexidine, and thickening agents, such as hypromellose.

The dosage unit involved depends, for example, on the condition treated, nature of the formulation, nature of the condition, embodiment of the claimed pharmaceutical compositions, mode of administration, and condition and weight of the patient. Dosage levels are typically sufficient to achieve a tissue concentration at the site of action that is at least the same as a concentration that has been shown to be active in vitro, in vivo, or in tissue culture. For example, a dosage of about 0.1 µg/kg body weight/day to about 1000 mg/kg body weight/day, for example, a dosage of about 1 µg/kg body weight/day to about 1000 µg/kg body weight/day, such as a dosage of about 5 µg/kg body weight/day to about 500 µg/kg body weight/day can be useful for treatment of a particular condition.

The compounds can be used in the form of pharmaceutically acceptable salts derived from inorganic or organic acids and bases, including, but not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include, but are not limited to, ammonium salts, alkali metal salts (such as sodium and potassium salts), alkaline earth metal salts (such as calcium and magnesium salts), salts with organic bases (such as dicyclohexylamine salts), N-methyl-D -glucamine, and salts with amino acids (such as arginine, lysine, etc.). Basic nitrogen-containing groups can be quaternized, for example, with such agents as C1-8 alkyl halides (such as methyl, ethyl, propyl, and butyl chlorides, bromides, and iodides), dialkyl sulfates (such as dimethyl, diethyl, dibutyl, an diamyl sulfates), long-chain halides (such as decyl, lauryl, myristyl, and stearyl chlorides, bromides, and iodides), aralkyl halides (such as benzyl and phenethyl bromides), etc. Water or oil-soluble or dispersible products are produced thereby.

Pharmaceutical compositions can be included in a kit accompanied by instructions for intended use, for example instructions required by a pharmaceutical regulatory agency, such as the Food and Drug Administration in the United States.

In view of the many possible embodiments of the invention that exist, it should be recognized that the illustrated embodiments are only examples of the invention and should not be taken as a limitation on the scope of the invention. Rather, the scope of the invention is defined by the following claims. We therefore claim as our invention, all that comes within the scope and spirit of these claims.

We claim:

1. A compound, the compound having the formula:

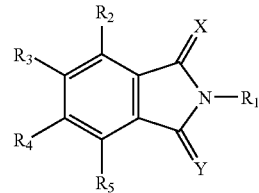

wherein Y is oxygen; X is oxygen or sulfur; each of $R_2$-$R_5$ are independently hydrogen, and $R_1$ is

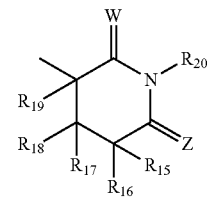

wherein W and Z are each independently oxygen or sulfur; $R_{20}$ is hydrogen; and $R_{15}$-$R_{19}$ are each independently hydrogen; and further wherein at least two of X, W and Z are sulfur; or a stereoisomer or pharmaceutically acceptable salt thereof.

2. The compound of claim 1, wherein the compound is 2,3-dihydro-3-thioxo-2-(2-oxo-6-thioxo-3-piperidinyl)-1H-isoindol-1-one or 2,3-Dihydro-3-thioxo-2-(2,6-dithioxo-3-piperidinyl)-1H-isoindol-1-one.

3. The compound of claim 1, wherein X, W and Z are each S.

4. The compound of claim 1, wherein X is S.

5. The compound of claim 1, wherein the compound has the structure:

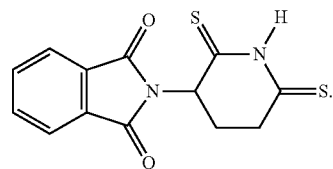

6. A pharmaceutical composition comprising at least one compound according to claim 1, and a pharmaceutically acceptable carrier.

7. The composition of claim 6, wherein the compound has the formula:

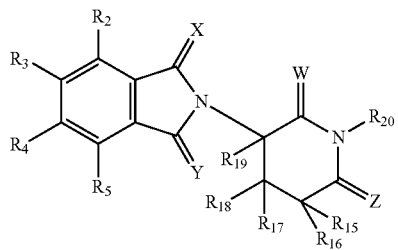

wherein X is sulfur or oxygen; or a stereoisomer or pharmaceutically acceptable salt thereof.

8. The compound of claim 1, wherein W and Z are each S, and X is O.

9. A pharmaceutical composition comprising a compound according to claim 5, and a pharmaceutically acceptable carrier.

10. The compound of claim 1, wherein X and Z are each S, and W is O.

11. A pharmaceutical composition comprising a compound according to claim 10, and a pharmaceutically acceptable carrier.

* * * * *